(12) United States Patent
Stephen et al.

(10) Patent No.: US 8,735,383 B2
(45) Date of Patent: May 27, 2014

(54) GLYCINE TRANSPORTER-1 INHIBITORS

(75) Inventors: Hitchcock Stephen, Jupiter, FL (US);
Albert Amegadzie, Moorpark, CA (US);
Wenyuan Qian, Camarillo, CA (US);
Xiaoyang Xia, Thousand Oaks, CA (US); Scott S. Harried, Woodland Hills, CA (US)

(73) Assignee: Amgen Inc., Thousand Oaks, CA (US)

( * ) Notice: Subject to any disclaimer, the term of this patent is extended or adjusted under 35 U.S.C. 154(b) by 24 days.

(21) Appl. No.: 13/426,539

(22) Filed: Mar. 21, 2012

(65) Prior Publication Data

US 2012/0195985 A1    Aug. 2, 2012

Related U.S. Application Data

(63) Continuation of application No. 12/464,697, filed on May 12, 2009, now Pat. No. 8,183,244, which is a continuation of application No. 11/823,027, filed on Jun. 26, 2007, now Pat. No. 7,538,114.

(60) Provisional application No. 60/816,936, filed on Jun. 28, 2006, provisional application No. 60/850,027, filed on Jan. 8, 2006.

(51) Int. Cl.
| | |
|---|---|
| *A01N 43/00* | (2006.01) |
| *A01N 43/62* | (2006.01) |
| *A61K 31/33* | (2006.01) |
| *A61K 31/55* | (2006.01) |
| *A61K 31/4965* | (2006.01) |
| *A61K 31/495* | (2006.01) |
| *A61K 31/551* | (2006.01) |
| *A61K 33/00* | (2006.01) |

(52) U.S. Cl.
CPC .............. *A61K 31/495* (2013.01); *A61K 31/551* (2013.01); *A61K 33/00* (2013.01)
USPC ......................... 514/183; 514/218; 514/255.04

(58) Field of Classification Search
CPC .... A61K 31/495; A61K 31/551; A61K 33/00
USPC ..................................... 514/183, 218, 255.04
See application file for complete search history.

(56) References Cited

U.S. PATENT DOCUMENTS

| | | | |
|---|---|---|---|
| 3,032,556 A | 5/1962 | Jucker et al. | |
| 3,928,356 A | 12/1975 | Umio et al. | |
| 4,082,755 A | 4/1978 | Van Wijngaarden et al. | |
| 4,525,358 A | 6/1985 | Baltes et al. | |
| 4,929,618 A | 5/1990 | Koda et al. | |
| 5,538,973 A | 7/1996 | Matsui et al. | |
| 5,658,908 A | 8/1997 | Chang et al. | |
| 5,700,801 A | 12/1997 | Pieper et al. | |
| 5,753,671 A | 5/1998 | Miller et al. | |
| 5,922,717 A | 7/1999 | Pieper et al. | |
| 6,001,854 A | 12/1999 | Ognyanov et al. | |
| 6,017,228 A * | 1/2000 | Verbeek et al. | 439/142 |
| 6,172,228 B1 * | 1/2001 | Kashima et al. | 544/360 |
| 6,200,978 B1 | 3/2001 | Maw et al. | |
| 6,248,766 B1 | 6/2001 | Ohkawa et al. | |
| 6,489,329 B2 | 12/2002 | Van de Venne | |
| 6,514,975 B1 | 2/2003 | Maw | |
| 6,569,849 B1 | 5/2003 | Jorgensen et al. | |
| 6,638,925 B2 | 10/2003 | Czollner et al. | |
| 6,693,099 B2 | 2/2004 | Degenhardt et al. | |
| 6,894,059 B1 | 5/2005 | Scannell et al. | |
| 7,538,114 B2 | 5/2009 | Hitchcock et al. | |
| 2004/0002503 A1 | 1/2004 | Chang et al. | |
| 2004/0259912 A1 | 12/2004 | Matsumoto et al. | |
| 2005/0032817 A1 | 2/2005 | Fraley et al. | |
| 2005/0080261 A1 | 4/2005 | Edgar et al. | |
| 2005/0107404 A1 | 5/2005 | Fraley et al. | |
| 2005/0171122 A1 | 8/2005 | Fraley et al. | |
| 2005/0176737 A1 | 8/2005 | Fraley et al. | |
| 2005/0228003 A1 | 10/2005 | Fraley et al. | |

FOREIGN PATENT DOCUMENTS

| | | |
|---|---|---|
| CN | 1415617 | 7/2003 |
| CN | 1415618 | 7/2003 |
| CN | 1415619 | 7/2003 |
| EP | 0335586 | 4/1989 |
| EP | 0399414 | 11/1990 |
| EP | 0598123 | 5/1994 |
| EP | 0949260 | 10/1999 |
| EP | 0820451 | 1/2003 |
| EP | 0649414 | 4/2003 |
| EP | 0938317 | 3/2004 |
| GB | 817 231 | 7/1959 |
| GB | 1280290 | 7/1972 |
| JP | 03-184963 | 8/1991 |
| JP | 05-148234 | 6/1993 |
| JP | 05148234 A2 | 6/1993 |
| JP | 07-138230 A2 | 5/1995 |
| JP | 03-246287 A2 | 1/2002 |
| JP | 03-352184 B2 | 3/2002 |

(Continued)

OTHER PUBLICATIONS

Singer, et al., Altered Mnemonic Functions and Resistance to N-methyl-D-Aspartate Receptor Antagonism by Forebrain Conditional Knockout of Glycine Transporter 1, Neuroscience, vol. 161, Issue 2, 635-654 (2009).*

(Continued)

*Primary Examiner* — Erich Leeser

(74) *Attorney, Agent, or Firm* — Elsa D. Lemoine

(57) ABSTRACT

The present invention provides compounds that are glycine transporter 1 (hereinafter referred to as GlyT-1) inhibitors and are therefore useful for the treatment of diseases treatable by inhibition of GlyT-1 such as cognitive disorders associated with Schizophrenia, ADHD (attention deficit hyperactivity disorder), MCI (mild cognitive impairment), and the like. Also provided are pharmaceutical compositions containing such compounds and processes for preparing such compounds.

25 Claims, No Drawings

(56) References Cited

FOREIGN PATENT DOCUMENTS

| | | |
|---|---|---|
| WO | WO 93/15062 | 8/1993 |
| WO | WO 95/23137 | 8/1995 |
| WO | WO 96/20173 | 7/1996 |
| WO | WO 96/31478 | 10/1996 |
| WO | WO 97/45115 | 12/1997 |
| WO | WO 97/45423 | 12/1997 |
| WO | WO 99/00376 | 1/1999 |
| WO | WO 98/52929 | 11/1999 |
| WO | WO 02/32874 | 4/2002 |
| WO | WO 02/066446 | 8/2002 |
| WO | WO 03/017939 | 3/2003 |
| WO | WO 03/022835 A1 | 3/2003 |
| WO | WO 03/032912 | 4/2003 |
| WO | WO 03/039255 | 5/2003 |
| WO | WO 03/043980 A1 | 5/2003 |
| WO | WO 03/053942 | 7/2003 |
| WO | WO 03/079970 | 10/2003 |
| WO | WO 2004/004728 | 1/2004 |
| WO | WO 2004/041802 | 5/2004 |
| WO | WO 2005/014563 | 2/2005 |
| WO | WO 2005/066148 | 7/2005 |
| WO | WO 2005/077373 | 8/2005 |
| WO | WO 2006/043691 | 4/2006 |
| WO | WO 2007/137417 A1 | 12/2007 |
| WO | WO 2007/137417 A1 | 12/2007 |

OTHER PUBLICATIONS

Sasa, M. et al. "Pharmacokinetics of Single and Multiple Doses of a New Antiallergic Drug, Cetirizine, and Examination and Its Safety," Jpn J Clin Pharmacol Ther. 26(2): 509-522 Jun. 1995.

Iwasaki, N. et al. "Amphoteric Drugs, I. Synthesis and Antiallergic Activity of [4-(Diphenylmethoxy)piperidino]-, [4-(Diphenylmethylene)piperidino]alkanoic Acid Derivatives," Chem. Pharm. Bull. 42(11) 2276-2284 (1994).

Wood, Stuart G., et al., "The metabolism and pharmacokinetics of 14C-cetirizine in humans," Database accession No. 1988:143030 abstract and Annals of Allergy, vol. 59(6. Pt. 2), 31-4, 1987.

Wang, Lisheng et al., "Method for preparation of chiral dibenzylpyrazine derivatives for preventing and treating allergic diseases," Database accession No. 2007:590996 abstract & CN 1970549A (Guangxi University, Peop. Re. China) May 30, 2007.

Database Chemcats and Otava Building Blocks; Database accession No. XP002455003; Publication Date Jun. 14, 2007.

Kline, R.H., et al., "3'Chloro-3α-(diphenylmethoxy)tropane But Not 4'Chloro-3α-(diphenylmethoxy)tropane Produces a Cocaine-like Behavioral Profile," J. Med. Chem., 1997, 40(6):851-857.

Morren, H.G., et al., "Nouveaux derives de la piperazine 1,4-disubstituee," Belgische Chemsiche Industrie, 1957, 22:409-420.

Chern, et al., "Design, synthesis, and structure-activity relationships of pyrazolo[3,4-d]pyrimidines: a novel class of potent enterovirus inhibitors," Bioorganic & Medicinal Chemistry Letters, 2004, 14(10):2519-2525.

Wu, et al., "Catalyzed asymmetric aryl transfer reactions to aldehydes with boroxines as aryl source," Tetrahedron: Asymmetry, 2005, 16:2299-2305.

\* cited by examiner

GLYCINE TRANSPORTER-1 INHIBITORS

CROSS-REFERENCE TO RELATED APPLICATIONS

This application is a continuation of U.S. application Ser. No. 12/464,697, filed on May 12, 2009, which is a continuation of U.S. application Ser. No. 11/823,027, now issued as U.S. Pat. No. 7,538,114, filed on Jun. 26, 2007, which claims priority under 35 U.S.C. 119(e) to U.S. provisional applications No. 60/816,936 filed on Jun. 28, 2006 and 60/850,027, filed on Oct. 6, 2006, the disclosures of which are incorporated herein by reference in their entirety.

FIELD OF THE INVENTION

The present invention provides compounds that are glycine transporter 1 (hereinafter referred to as GlyT-1) inhibitors and are therefore useful for the treatment of diseases treatable by inhibition of GlyT1 such as cognitive disorders associated with Schizophrenia, ADHD (attention deficit hyperactivity disorder), MCI (mild cognitive impairment), and the like. Also provided are pharmaceutical compositions containing such compounds and processes for preparing such compounds.

BACKGROUND

Glycine is a principal inhibitory neurotransmitter in the mammalian CNS, but also serves as endogenous obligatory co-agonist with glutamate for activating N-methyl-D-aspartate (NMDA) receptors. The synaptic actions of glycine end through the activity of high affinity transportes located in neuronal and glial membranes. The glycine transporter type 1 (GlyT1) is involved in glycine re-uptake processes at the level of excitatory synapses. Blockade of GlyT1 increases glycine concentration at excitatory synapses, thus potentiating NMDA neurotransmission. Since schizophrenia has been associated with hypofunction of NMDA receptors in such brain regions as prefrontal cortex and hippocampus, an inhibitor of GlyT1 would restore normal NMDA transmission and thereby reduce schizophrenia symptoms. In addition to schizophrenia, GlyT1 inhibitors can be used in other conditions characterized by impaired NMDA transmission, such as broad cognitive deficits (including MCI) and Alzheimer's disease.

Existing therapeutics for schizophrenia are efficacious only at treating positive symptoms of the disease. Negative symptoms, including flattened affect, social withdrawal as well as cognitive deficits are not ameliorated by current medications, which primarily target the mesolimbic dopamine system. Therefore, novel treatments for schizophrenia are needed to specifically improve negative symptoms and cognitive deficits associated with the disease. The present invention fulfills this need and related needs.

SUMMARY OF THE INVENTION

In one aspect, this invention is directed to a compound of Formula (I):

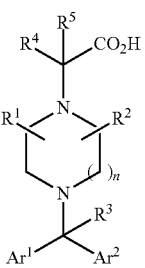

(I)

wherein:

n is an integer from 1 to 3;

$R^1$ and $R^2$ are independently selected from hydrogen, alkyl, haloalkyl, alkoxy, haloalkoxy, aryl, heteroaryl, cycloalkyl, or heterocyclyl wherein the aforementioned rings are optionally substituted with $R^a$, $R^b$, or $R^c$ independently selected from alkyl, halo, haloalkyl, alkoxy, haloalkoxy, hydroxy, cyano, monosubstituted amino, or disubstituted amino; or $R^1$ and $R^2$ when attached to same carbon can together from an oxo group; or $R^1$ and $R^2$, when attached to the same carbon atom, can combine to form cycloalkyl or monocyclic saturated heterocyclyl to give a spiro ring wherein the cycloalkyl or monocyclic saturated heterocyclyl can be optionally substituted with $R^d$, $R^e$, or $R^f$ independently selected from alkyl, alkoxy, fluoro, fluoroalkyl, fluoroalkoxy, hydroxy, monosubstituted amino, or disubstituted amino; or $R^1$ and $R^2$, when attached to carbon atoms 2 and 5 or 3 and 6 positions of the piperazine ring, can combine to form —$C_1$-$C_3$— alkylene chain wherein one of the carbon atoms in the alkylene chain is optionally replaced by a —NR—, —O—, —S(O)n1- (where R is hydrogen or alkyl and n1 is 0-2) and further wherein one or two hydrogen atoms in the alkylene chain can be optionally substituted with one or two alkyl;

$R^3$, $R^4$ and $R^5$ are independently hydrogen, alkyl, fluoro, or fluoroalkyl; and $Ar^1$ and $Ar^2$ are independently aryl, heteroaryl, cycloalkyl, or heterocyclyl where each of the aforementioned ring is optionally substituted with $R^g$, $R^h$ or $R^i$ where $R^g$ is alkyl, —C≡C—$R^6$ (where $R^6$ is aryl or heteroaryl), halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, or acylamino and $R^h$ and $R^i$ are independently selected from alkyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, acylamino, aryl, heteroaryl, cycloalkyl, or heterocyclyl where the aromatic or alicyclic ring in $R^g$, $R^h$ and $R^i$ is optionally substituted with $R^j$, $R^k$ or $R^l$ which are independently selected from alkyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, or acylamino; or a pharmaceutically acceptable salt thereof provided that: the compound of Formula (I) is not 2-(4-benzhydrylpiperazin-1-yl)acetic acid, 2-(4-((4-chlorophenyl)(phenyl)methyl)piperazin-1-yl)acetic acid.

In some embodiments, the compound of Formula (I) has the structure shown below:

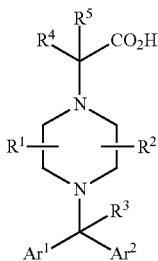

wherein:

$R^1$ and $R^2$ are independently selected from hydrogen, alkyl, haloalkyl, alkoxy, haloalkoxy, aryl, heteroaryl, cycloalkyl, or heterocyclyl wherein the aforementioned rings are optionally substituted with $R^a$, $R^b$, or $R^c$ independently selected from alkyl, halo, haloalkyl, alkoxy, haloalkoxy, hydroxy, cyano, monosubstituted amino, or disubstituted amino; or $R^1$ and $R^2$ when attached to same carbon can together from an oxo group; or $R^1$ and $R^2$, when attached to the same carbon atom, can combine to form cycloalkyl or monocyclic saturated heterocyclyl to give a spiro ring wherein the cycloalkyl or monocyclic saturated heterocyclyl can be optionally substituted with $R^d$, $R^e$, or $R^f$ independently selected from alkyl, alkoxy, fluoro, fluoroalkyl, fluoroalkoxy, hydroxy, monosubstituted amino, or disubstituted amino; or $R^1$ and $R^2$, when attached to carbon atoms 2 and 5 or 3 and 6 positions of the piperazine ring, can combine to form —$C_1$-$C_3$— alkylene chain wherein one of the carbon atoms in the alkylene chain is optionally replaced by a —NR—, —O—, —S(O)n1- (where R is hydrogen or alkyl and n1 is 0-2) and further wherein one or two hydrogen atoms in the alkylene chain can be optionally substituted with one or two alkyl;

$R^3$, $R^4$ and $R^5$ are independently hydrogen, alkyl, fluoro, or fluoroalkyl; and $Ar^1$ and $Ar^2$ are independently aryl, heteroaryl, cycloalkyl, or heterocyclyl where each of the aforementioned ring is optionally substituted with $R^g$, $R^h$ or $R^i$ where $R^g$ is alkyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, acylamino, aryl, heteroaryl, cycloalkyl, or heterocyclyl where the aromatic or alicyclic ring in $R^g$, $R^h$ and $R^i$ is optionally substituted with $R^j$, $R^k$ or $R^l$ which are independently selected from alkyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, aminoalkyl, hydroxyalkoxy, alkoxyalkoxy, aminoalkoxy, aminosulfonyl, aminocarbonyl, or acylamino; or a pharmaceutically acceptable salt thereof provided that: the compound of Formula (I) is not 2-(4-benzhydrylpiperazin-1-yl)acetic acid or 2-(4-((4-chlorophenyl)(phenyl)methyl)piperazin-1-yl)acetic acid.

In some embodiments, in the compound of Formula (I), $R^1$ and $R^2$ are independently selected from hydrogen, alkyl, haloalkyl, alkoxy, haloalkoxy, aryl, heteroaryl, cycloalkyl, or heterocyclyl wherein the aforementioned rings are optionally substituted with $R^a$, $R^b$, or $R^c$ independently selected from alkyl, halo, haloalkyl, alkoxy, haloalkoxy, hydroxy, cyano, monosubstituted amino, or disubstituted amino; or $R^1$ and $R^2$, when attached to the same carbon atom, can combine to form cycloalkyl or monocyclic saturated heterocyclyl to give a spiro ring wherein the cycloalkyl or monocyclic saturated heterocyclyl can be optionally substituted with $R^d$, $R^e$, or $R^f$ independently selected from alkyl, alkoxy, fluoro, fluoroalkyl, fluoroalkoxy, hydroxy, monosubstituted amino, or disubstituted amino; or $R^1$ and $R^2$, when attached to carbon atoms 2 and 5 or 3 and 6 positions of the piperazine ring, can combine to form —$C_1$-$C_3$— alkylene chain wherein one of the carbon atoms in the alkylene chain is optionally replaced by a —NR—, —O—, —S(O)n1- (where R is hydrogen or alkyl and n1 is 0-2) and further wherein one or two hydrogen atoms in the alkylene chain can be optionally substituted with one or two alkyl;

$R^3$, $R^4$ and $R^5$ are independently hydrogen, alkyl, fluoro, or fluoroalkyl; and $Ar^1$ and $Ar^2$ are independently aryl, heteroaryl, cycloalkyl, or heterocyclyl where each of the aforementioned ring is optionally substituted with $R^g$, $R^h$ or $R^i$ where $R^g$ is alkyl, —C≡C—$R^6$ (where $R^6$ is aryl or heteroaryl), halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, or acylamino and $R^h$ and $R^i$ are independently selected from alkyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, acylamino, aryl, heteroaryl, cycloalkyl, or heterocyclyl where the aromatic or alicyclic ring in $R^g$, $R^h$ and $R^i$ is optionally substituted with $R^j$, $R^k$ or $R^l$ which are independently selected from alkyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, or acylamino In some embodiments, in the compound of Formula (I), $R^1$ and $R^2$ are independently selected from hydrogen, alkyl, haloalkyl, alkoxy, haloalkoxy, aryl, heteroaryl, cycloalkyl, or heterocyclyl wherein the aforementioned rings are optionally substituted with $R^a$, $R^b$, or $R^c$ independently selected from alkyl, halo, haloalkyl, alkoxy, haloalkoxy, hydroxy, cyano, monosubstituted amino, or disubstituted amino; or $R^1$ and $R^2$, when attached to the same carbon atom, can combine to form cycloalkyl or monocyclic saturated heterocyclyl to give a spiro ring wherein the cycloalkyl or monocyclic saturated heterocyclyl can be optionally substituted with $R^d$, $R^e$, or $R^f$ independently selected from alkyl, alkoxy, fluoro, fluoroalkyl, fluoroalkoxy, hydroxy, monosubstituted amino, or disubstituted amino; or $R^1$ and $R^2$, when attached to carbon atoms 2 and 5 or 3 and 6 positions of the piperazine ring, can combine to form —$C_1$-$C_3$— alkylene chain wherein one of the carbon atoms in the alkylene chain is optionally replaced by a —NR—, —O—, —S(O)n1- (where R is hydrogen or alkyl and n1 is 0-2) and further wherein one or two hydrogen atoms in the alkylene chain can be optionally substituted with one or two alkyl;

$R^3$, $R^4$ and $R^5$ are independently hydrogen, alkyl, fluoro, or fluoroalkyl; and $Ar^1$ and $Ar^2$ are independently aryl, heteroaryl, cycloalkyl, or heterocyclyl where each of the aforementioned ring is optionally substituted with $R^g$, $R^h$ or $R^i$ where $R^g$ is alkyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, or acylamino and $R^h$ and $R^i$ are independently selected from alkyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, acylamino, aryl, heteroaryl, cycloalkyl, or heterocyclyl where the aromatic or alicyclic ring in $R^g$, $R^h$ and $R^i$ is optionally substituted with $R^j$, $R^k$ or $R^l$ which are independently selected from alkyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, or acylamino; provided that when (i) $R^1$ and $R^2$ are methyl, $R^3$, $R^4$ and $R^5$ are hydrogen, and $Ar^1$ is 3-hydroxyphenyl, then $Ar^2$ is not 4-cyanophenyl or 4-1H-tetrazol-5-ylphenyl and (ii) $R^1$, $R^2$, $R^3$, $R^4$ and $R^5$ are hydrogen and $Ar^1$ is phenyl then $Ar^2$ is not phenyl or 4-chlorophenyl.

In a second aspect, this invention is directed to a pharmaceutical composition comprising a compound of Formula (I), a pharmaceutically acceptable salt thereof or a mixture a compound of Formula (I) and a pharmaceutically acceptable salt thereof; and a pharmaceutically acceptable excipient. In one embodiment, n is 1.

In a third aspect, this invention is directed to a method of treating a disease treatable by inhibition of GlyT1 receptor in a patient which method comprises administering to the patient a pharmaceutical composition comprising a compound of Formula (I):

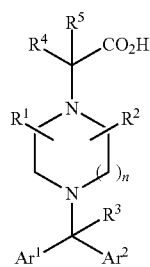

(I)

wherein:

n is an integer from one to three;

$R^1$ and $R^2$ are independently selected from hydrogen, alkyl, haloalkyl, alkoxy, haloalkoxy, aryl, heteroaryl, cycloalkyl, or heterocyclyl wherein the aforementioned rings are optionally substituted with $R^a$, $R^b$, or $R^c$ independently selected from alkyl, halo, haloalkyl, alkoxy, haloalkoxy, hydroxy, cyano, monosubstituted amino, or disubstituted amino; or $R^1$ and $R^2$ when attached to same carbon can together from an oxo group; or $R^1$ and $R^2$, when attached to the same carbon atom, can combine to form cycloalkyl or monocyclic saturated heterocyclyl to give a spiro ring wherein the cycloalkyl or monocyclic saturated heterocyclyl can be optionally substituted with $R^d$, $R^e$, or $R^f$ independently selected from alkyl, alkoxy, fluoro, fluoroalkyl, fluoroalkoxy, hydroxy, monosubstituted amino, or disubstituted amino; or $R^1$ and $R^2$, when attached to carbon atoms 2 and 5 or 3 and 6 positions of the piperazine ring, can combine to form —$C_1$-$C_3$— alkylene chain wherein one of the carbon atoms in the alkylene chain is optionally replaced by a —NR—, —O—, —S(O)n1- (where R is hydrogen or alkyl and n1 is 0-2) and further wherein one or two hydrogen atoms in the alkylene chain can be optionally substituted with one or two alkyl;

$R^3$, $R^4$ and $R^5$ are independently hydrogen, alkyl, fluoro, or fluoroalkyl; and $Ar^1$ and $Ar^2$ are independently aryl, heteroaryl, cycloalkyl, or heterocyclyl where each of the aforementioned ring is optionally substituted with $R^g$, $R^h$ or $R^i$ where $R^g$ is alkyl, —C≡C—$R^6$ (where $R^6$ is aryl or heteroaryl), halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, or acylamino and $R^h$ and $R^i$ are independently selected from alkyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, acylamino, aryl, heteroaryl, cycloalkyl, or heterocyclyl where the aromatic or alicyclic ring in $R^g$, $R^h$ and $R^i$ is optionally substituted with $R^j$, $R^k$ or $R^l$ which are independently selected from alkyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, or acylamino; or a pharmaceutically acceptable salt thereof, or a mixture a compound of Formula (I) and a pharmaceutically acceptable salt thereof and a pharmaceutically acceptable excipient.

In some embodiments, in the method above, the compound of Formula (I) is where $R^1$ and $R^2$ are independently selected from hydrogen, alkyl, haloalkyl, alkoxy, haloalkoxy, aryl, heteroaryl, cycloalkyl, or heterocyclyl wherein the aforementioned rings are optionally substituted with $R^a$, $R^b$, or $R^c$ independently selected from alkyl, halo, haloalkyl, alkoxy, haloalkoxy, hydroxy, cyano, monosubstituted amino, or disubstituted amino; or $R^1$ and $R^2$, when attached to the same carbon atom, can combine to form cycloalkyl or monocyclic saturated heterocyclyl to give a spiro ring wherein the cycloalkyl or monocyclic saturated heterocyclyl can be optionally substituted with $R^d$, $R^e$, or $R^f$ independently selected from alkyl, alkoxy, fluoro, fluoroalkyl, fluoroalkoxy, hydroxy, monosubstituted amino, or disubstituted amino; or $R^1$ and $R^2$, when attached to carbon atoms 2 and 5 or 3 and 6 positions of the piperazine ring, can combine to form —$C_1$-$C_3$— alkylene chain wherein one of the carbon atoms in the alkylene chain is optionally replaced by a —NR—, —O—, —S(O)n1- (where R is hydrogen or alkyl and n1 is 0-2) and further wherein one or two hydrogen atoms in the alkylene chain can be optionally substituted with one or two alkyl;

$R^3$, $R^4$ and $R^5$ are independently hydrogen, alkyl, fluoro, or fluoroalkyl; and $Ar^1$ and $Ar^2$ are independently aryl, heteroaryl, cycloalkyl, or heterocyclyl where each of the aforementioned ring is optionally substituted with $R^g$, $R^h$ or $R^i$ where $R^g$ is alkyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, or acylamino and $R^h$ and $R^i$ are independently selected from alkyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, acylamino, aryl, heteroaryl, cycloalkyl, or heterocyclyl where the aromatic or alicyclic ring in $R^g$, $R^h$ and $R^i$ is optionally substituted with $R^j$, $R^k$ or $R^l$ which are independently selected from alkyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, or acylamino.

In some embodiments, in the method above, the compound of Formula (I) is where n is 1. In one embodiment the disease is ADHD (attention deficit hyperactivity disorder), MCI (mild cognitive impairment), or cognitive disorders associated with Schizophrenia.

In a fourth aspect, this invention is directed to a method of making a compound Formula (I):

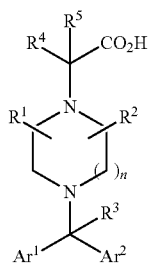

(I)

wherein:

n is an integer from 1 to 3;

$R^1$ and $R^2$ are independently selected from hydrogen, alkyl, haloalkyl, alkoxy, haloalkoxy, aryl, heteroaryl, cycloalkyl, or heterocyclyl wherein the aforementioned rings are optionally substituted with $R^a$, $R^b$, or $R^c$ independently selected from alkyl, halo, haloalkyl, alkoxy, haloalkoxy, hydroxy, cyano, monosubstituted amino, or disubstituted amino; or $R^1$ and $R^2$, when attached to the same carbon atom, can combine to form cycloalkyl or monocyclic saturated heterocyclyl to give a spiro ring wherein the cycloalkyl or monocyclic saturated heterocyclyl can be optionally substituted with $R^d$, $R^e$, or $R^f$ independently selected from alkyl, alkoxy, fluoro, fluoroalkyl, fluoroalkoxy, hydroxy, monosubstituted amino, or disubstituted amino; or $R^1$ and $R^2$, when attached to carbon atoms 2 and 5 or 3 and 6 positions of the piperazine ring, can combine to form —$C_1$-$C_3$— alkylene chain wherein one of the carbon atoms in the alkylene chain is optionally replaced by a —NR—, —O—, —S(O)n1- (where R is hydrogen or alkyl and n1 is 0-2) and further wherein one or two hydrogen atoms in the alkylene chain can be optionally substituted with one or two alkyl;

$R^3$, $R^4$ and $R^5$ are independently hydrogen, alkyl, fluoro, or fluoroalkyl; and $Ar^1$ and $Ar^2$ are independently aryl, heteroaryl, cycloalkyl, or heterocyclyl where each of the aforementioned ring is optionally substituted with $R^g$, $R^h$ or $R^i$ where $R^g$ is alkyl, —C≡C—$R^6$ (where $R^6$ is aryl or heteroaryl), halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, or acylamino and $R^h$ and $R^i$ are independently selected from alkyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, acylamino, aryl, heteroaryl, cycloalkyl, or heterocyclyl where the aromatic or alicyclic ring in $R^g$, $R^h$ and $R^i$ is optionally substituted with $R^j$, $R^k$ or $R^l$ which are independently selected from alkyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, or acylamino;

comprising:

(a) hydrolyzing the ester group in a compound of formula:

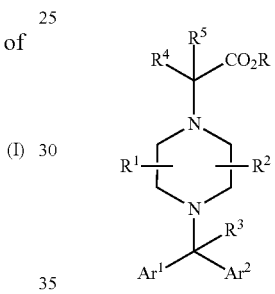

where R is alkyl and $R^1$, $R^2$, $R^3$, $R^4$, $R^5$, $Ar^1$ and $Ar^2$ groups are as defined above; under acidic or basic hydrolysis reaction conditions;

(b) optionally modifying any of the $R^1$, $R^2$, $R^3$, $R^4$, $R^5$, $Ar^1$ and $Ar^2$ groups to provide a compound of Formula (I);

(c) optionally forming an acid addition salt of the compound of Formula (I) obtained from Step (a) and/or (b) above;

(d) optionally separating stereoisomers of the compound of Formula (I) obtained from Step (a), (b), and/or (c) above;

provided that when (i) $R^1$ and $R^2$ are methyl, $R^3$, $R^4$ and $R^5$ are hydrogen, and $Ar^1$ is 3-hydroxyphenyl, then $Ar^2$ is not 4-cyanophenyl or 4-1H-tetrazol-5-ylphenyl and (ii) $R^1$, $R^2$, $R^3$, $R^4$ and $R^5$ are hydrogen and $Ar^1$ is phenyl then $Ar^2$ is not phenyl or 4-chlorophenyl;

In some embodiments in the process above, the compound of Formula (I) is where:

$R^1$ and $R^2$ are independently hydrogen or alkyl;

$R^3$, $R^4$, and $R^5$ are hydrogen; and $Ar^1$ and $Ar^2$ are independently phenyl, each ring optionally substituted with $R^g$ or $R^h$ where $R^g$ and $R^h$ are independently alkyl, halo, haloalkyl, haloalkoxy, alkylthio, alkoxy, alkylcarbonyl, or alkoxycarbonyl.

In some embodiments in the process above, the compound of Formula (I) is where:

$R^1$ and $R^2$ are independently hydrogen or alkyl;

$R^3$, $R^4$, and $R^5$ are hydrogen; and $Ar^1$ and $Ar^2$ are independently phenyl, each ring optionally substituted with $R^g$ or $R^h$ where $R^g$ and $R^h$ are independently alkyl, halo, haloalkyl, haloalkoxy, alkylthio, alkoxy, alkylcarbonyl, or alkoxycarbonyl and the stereochemistry at the carbon carrying the $R^3$, $Ar^1$ and $Ar^2$ group is (R).

DETAILED DESCRIPTION

Definitions

Unless otherwise stated, the following terms used in the specification and claims are defined for the purposes of this Application and have the following meaning:

"Alkyl" means a linear saturated monovalent hydrocarbon radical of one to six carbon atoms or a branched saturated monovalent hydrocarbon radical of three to six carbon atoms, e.g., methyl, ethyl, propyl, 2-propyl, butyl (including all isomeric forms), pentyl (including all isomeric forms), and the like.

"Alicyclic" means a non-aromatic ring e.g., cycloalkyl or heterocyclyl ring.

"Alkylene" means a linear saturated divalent hydrocarbon radical of one to six carbon atoms or a branched saturated divalent hydrocarbon radical of three to six carbon atoms unless otherwise stated e.g., methylene, ethylene, propylene, 1-methylpropylene, 2-methylpropylene, butylene, pentylene, and the like.

"Alkylthio" means a —SR radical where R is alkyl as defined above, e.g., methylthio, ethylthio, and the like.

"Alkylsulfonyl" means a —SO$_2$R radical where R is alkyl as defined above, e.g., methylsulfonyl, ethylsulfonyl, and the like.

"Amino" means a —NH$_2$.

"Alkylamino" means a —NHR radical where R is alkyl as defined above, e.g., methylamino, ethylamino, propylamino, or 2-propylamino, and the like.

"Alkoxy" means a —OR radical where R is alkyl as defined above, e.g., methoxy, ethoxy, propoxy, or 2-propoxy, n-, iso-, or tert-butoxy, and the like.

"Alkoxycarbonyl" means a —C(O)OR radical where R is alkyl as defined above, e.g., methoxycarbonyl, ethoxycarbonyl, and the like.

"Alkoxyalkyl" means a linear monovalent hydrocarbon radical of one to six carbon atoms or a branched monovalent hydrocarbon radical of three to six carbons substituted with at least one alkoxy group, preferably one or two alkoxy groups, as defined above, e.g., 2-methoxyethyl, 1-, 2-, or 3-methoxypropyl, 2-ethoxyethyl, and the like.

"Alkoxyalkyloxy" or "alkoxyalkoxy" means a —OR radical where R is alkoxyalkyl as defined above, e.g., methoxyethoxy, 2-ethoxyethoxy, and the like.

"Aminoalkyl" means a linear monovalent hydrocarbon radical of one to six carbon atoms or a branched monovalent hydrocarbon radical of three to six carbons substituted with at least one, preferably one or two, —NRR' where R is hydrogen, alkyl, or —COR$^a$ where R$^a$ is alkyl, each as defined above, and R' is selected from hydrogen, alkyl, hydroxyalkyl, alkoxyalkyl, aryl, aralkyl, heteroaryl, heteroaralkyl, or haloalkyl, each as defined herein, e.g., aminomethyl, methylaminoethyl, 2-ethylamino-2-methylethyl, 1,3-diaminopropyl, dimethylaminomethyl, diethylaminoethyl, acetylaminopropyl, and the like.

"Aminoalkoxy" means a —OR radical where R is aminoalkyl as defined above, e.g., 2-aminoethoxy, 2-dimethylaminopropoxy, and the like.

"Aminocarbonyl" means a —CONRR' radical where R is independently hydrogen, alkyl, hydroxyalkyl, alkoxyalkyl, or aminoalkyl, each as defined herein and R' is hydrogen, alkyl, cycloalkyl, cycloalkylalkyl, aryl, aralkyl, heteroaryl, heteroaralkyl, heterocyclyl, heterocyclylalkyl, hydroxyalkyl, alkoxyalkyl, or aminoalkyl, each as defined herein, e.g., —CONH$_2$, methylaminocarbonyl, 2-dimethylaminocarbonyl, and the like.

"Aminosulfonyl" means a —SO$_2$NRR' radical where R is independently hydrogen, alkyl, hydroxyalkyl, alkoxyalkyl, or aminoalkyl, each as defined herein and R' is hydrogen, alkyl, cycloalkyl, cycloalkylalkyl, aryl, aralkyl, heteroaryl, heteroaralkyl, heterocyclyl, heterocyclylalkyl, hydroxyalkyl, alkoxyalkyl, or aminoalkyl, each as defined herein, e.g., —SO$_2$NH$_2$, methylaminosulfonyl, 2-dimethylaminosulfonyl, and the like.

"Acyl" means a —COR radical where R is alkyl, haloalkyl, cycloalkyl, cycloalkylalkyl, aryl, aralkyl, heteroaryl, heteroaralkyl, heterocyclyl, or heterocyclylalkyl, each as defined herein, e.g., acetyl, propionyl, benzoyl, pyridinylcarbonyl, and the like. When R is alkyl, the radical is also referred to herein as alkylcarbonyl.

"Acylamino" means a —NHCOR radical where R is alkyl, haloalkyl, cycloalkyl, cycloalkylalkyl, aryl, aralkyl, heteroaryl, heteroaralkyl, heterocyclyl, or heterocyclylalkyl, each as defined herein, e.g., acetylamino, propionylamino, and the like.

"Aryl" means a monovalent monocyclic or bicyclic aromatic hydrocarbon radical of 6 to 10 ring atoms e.g., phenyl or naphthyl.

"Aralkyl" means a -(alkylene)-R radical where R is aryl as defined above.

"Cycloalkyl" means a cyclic saturated monovalent hydrocarbon radical of three to ten carbon atoms wherein one or two carbon atoms may be replaced by an oxo group, e.g., cyclopropyl, cyclobutyl, cyclopentyl, or cyclohexyl, and the like.

"Cycloalkylalkyl" means a -(alkylene)-R radical where R is cycloalkyl as defined above; e.g., cyclopropylmethyl, cyclobutylmethyl, cyclopentylethyl, or cyclohexylmethyl, and the like.

"Carboxy" means —COOH.

"Central piperazinyl ring" refers to

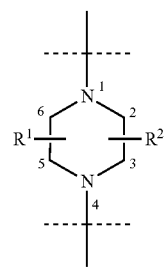

ring in Formula (I) and is numbered as shown above.

"Disubstituted amino" means a —NRR' radical where R and R' are independently alkyl, cycloalkyl, cycloalkylalkyl, acyl, sulfonyl, aryl, aralkyl, heteroaryl, heteroaralkyl, heterocyclyl, heterocyclylalkyl, hydroxyalkyl, alkoxyalkyl, or aminoalkyl, each as defined herein, e.g., dimethylamino, phenylmethylamino, and the like.

"Halo" means fluoro, chloro, bromo, or iodo, preferably fluoro or chloro.

"Haloalkyl" means alkyl radical as defined above, which is substituted with one or more halogen atoms, preferably one to five halogen atoms, preferably fluorine or chlorine, including those substituted with different halogens, e.g., —CH$_2$Cl, —CF$_3$, —CHF$_2$, —CH$_2$CF$_3$, —CF$_2$CF$_3$, —CF(CH$_3$)$_3$, and the like. When the alkyl is substituted with only fluoro, it is referred to in this Application as fluoroalkyl.

"Haloalkoxy" means a —OR radical where R is haloalkyl as defined above e.g., —OCF$_3$, —OCHF₂, and the like. When R is haloalkyl where the alkyl is substituted with only fluoro, it is referred to in this Application as fluoroalkoxy.

"Hydroxyalkyl" means a linear monovalent hydrocarbon radical of one to six carbon atoms or a branched monovalent hydrocarbon radical of three to six carbons substituted with one or two hydroxy groups, provided that if two hydroxy groups are present they are not both on the same carbon atom. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl, preferably 2-hydroxyethyl, 2,3-dihydroxypropyl, and 1-(hydroxymethyl)-2-hydroxyethyl.

"Hydroxyalkoxy" or "hydroxyalkyloxy" means a —OR radical where R is hydroxyalkyl as defined above.

"Heterocyclyl" means a saturated or unsaturated monovalent monocyclic group of 5 to 8 ring atoms in which one or two ring atoms are heteroatom selected from N, O, or S(O)$_n$, where n is an integer from 0 to 2, the remaining ring atoms being C. The heterocyclyl ring is optionally fused to a (one) aryl or heteroaryl ring as defined herein provided the aryl and heteroaryl rings are monocyclic. The heterocyclyl ring fused to monocyclic aryl or heteroaryl ring is also referred to in this Application as "bicyclic heterocyclyl" ring. Additionally, one or two ring carbon atoms in the heterocyclyl ring can optionally be replaced by a —CO— group. More specifically the term heterocyclyl includes, but is not limited to, pyrrolidino, piperidino, homopiperidino, 2-oxopyrrolidinyl, 2-oxopiperidinyl, morpholino, piperazino, tetrahydropyranyl, thiomorpholino, and the like. When the heterocyclyl ring is unsaturated it can contain one or two ring double bonds provided that the ring is not aromatic. When the heterocyclyl group contains at least one nitrogen atom, it is also referred to herein as heterocycloamino and is a subset of the heterocyclyl group. When the heterocyclyl group is a saturated ring and is not fused to aryl or heteroaryl ring as stated above, it is also referred to herein as saturated monocyclic heterocyclyl.

"Heterocyclylalkyl" means a -(alkylene)-R radical where R is heterocyclyl ring as defined above e.g., tetraydrofuranylmethyl, piperazinylmethyl, morpholinylethyl, and the like.

"Heteroaryl" means a monovalent monocyclic or bicyclic aromatic radical of 5 to 10 ring atoms where one or more, preferably one, two, or three, ring atoms are heteroatom selected from N, O, or S, the remaining ring atoms being carbon. Representative examples include, but are not limited to, pyrrolyl, thienyl, thiazolyl, imidazolyl, furanyl, indolyl, isoindolyl, oxazolyl, isoxazolyl, benzothiazolyl, benzoxazolyl, quinolinyl, isoquinolinyl, pyridinyl, pyrimidinyl, pyrazinyl, pyridazinyl, triazolyl, tetrazolyl, and the like.

"Heteroaralkyl" means a -(alkylene)-R radical where R is heteroaryl as defined above.

"Monosubstituted amino" means a —NHR radical where R is alkyl, cycloalkyl, cycloalkylalkyl, acyl, sulfonyl, aryl, aralkyl, heteroaryl, heteroaralkyl, heterocyclyl, heterocyclylalkyl, hydroxyalkyl, alkoxyalkyl, or aminoalkyl, each as defined herein, e.g., methylamino, 2-phenylamino, hydroxyethylamino, and the like.

"Spiro" compound is a bicyclic compound with rings connected through just one atom, the connecting atom is also called the spiroatom, most often a quaternary carbon ("spiro carbon"). Representative examples include, but are not limited to,

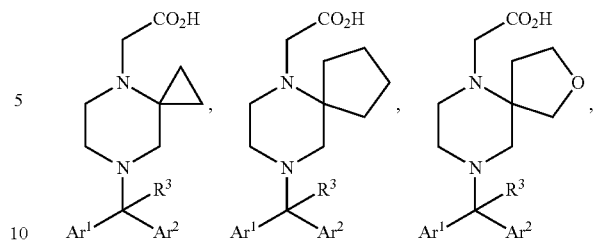

and the like.

The present invention also includes the prodrugs of compounds of Formula (I). The term prodrug is intended to represent covalently bonded carriers, which are capable of releasing the active ingredient of Formula (I) when the prodrug is administered to a mammalian subject. Release of the active ingredient occurs in vivo. Prodrugs can be prepared by techniques known to one skilled in the art. These techniques generally modify appropriate functional groups in a given compound. These modified functional groups however regenerate original functional groups in vivo or by routine manipulation. Prodrugs of compounds of Formula (I) include compounds wherein a hydroxy, amino, carboxylic, or a similar group is modified. Examples of prodrugs include, but are not limited to esters (e.g., acetate, formate, and benzoate derivatives), carbamates (e.g., N,N-dimethylaminocarbonyl) of hydroxy or amino functional groups in compounds of Formula (I)), amides (e.g., trifluoroacetylamino, acetylamino, and the like), and the like. Prodrugs of compounds of Formula (I) are also within the scope of this invention.

The present invention also includes protected derivatives of compounds of Formula (I). For example, when compounds of Formula (I) contain groups such as hydroxy, carboxy, thiol or any group containing a nitrogen atom(s), these groups can be protected with a suitable protecting groups. A comprehensive list of suitable protective groups can be found in T. W. Greene, *Protective Groups in Organic Synthesis*, John Wiley & Sons, Inc. (1999), the disclosure of which is incorporated herein by reference in its entirety. The protected derivatives of compounds of Formula (I) can be prepared by methods well known in the art.

A "pharmaceutically acceptable salt" of a compound means a salt that is pharmaceutically acceptable and that possesses the desired pharmacological activity of the parent compound. Such salts include:

acid addition salts, formed with inorganic acids such as hydrochloric acid, hydrobromic acid, sulfuric acid, nitric acid, phosphoric acid, and the like; or formed with organic acids such as formic acid, acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. It is understood that the pharmaceutically acceptable salts are non-toxic. Additional information on suitable pharmaceutically acceptable salts can be found in *Remington's Pharmaceutical Sciences,* 17th ed., Mack Publishing Company, Easton, Pa., 1985, which is incorporated herein by reference.

The compounds of the present invention may have asymmetric centers. Compounds of the present invention containing an asymmetrically substituted atom may be isolated in optically active or racemic forms. It is well known in the art how to prepare optically active forms, such as by resolution of materials. All chiral, diastereomeric, racemic forms are within the scope of this invention, unless the specific stereochemistry or isomeric form is specifically indicated.

Certain compounds of Formula (I) can exist as tautomers and/or geometric isomers. All possible tautomers and cis and trans isomers, as individual forms and mixtures thereof are within the scope of this invention. Additionally, as used herein the term alkyl includes all the possible isomeric forms of said alkyl group albeit only a few examples are set forth. Furthermore, when the cyclic groups such as aryl, heteroaryl, heterocyclyl are substituted, they include all the positional isomers albeit only a few examples are set forth. Furthermore, all polymorphic forms and hydrates of a compound of Formula (I) are within the scope of this invention.

"Oxo" or "carbonyl" means =(O) group.

"Optional" or "optionally" means that the subsequently described event or circumstance may but need not occur, and that the description includes instances where the event or circumstance occurs and instances in which it does not. For example, "heterocyclyl group optionally substituted with an alkyl group" means that the alkyl may but need not be present, and the description includes situations where the heterocyclyl group is substituted with an alkyl group and situations where the heterocyclyl group is not substituted with alkyl.

A "pharmaceutically acceptable carrier or excipient" means a carrier or an excipient that is useful in preparing a pharmaceutical composition that is generally safe, non-toxic and neither biologically nor otherwise undesirable, and includes a carrier or an excipient that is acceptable for veterinary use as well as human pharmaceutical use. "A pharmaceutically acceptable carrier/excipient" as used in the specification and claims includes both one and more than one such excipient.

"Sulfonyl" means a —SO$_2$R radical where R is alkyl, haloalkyl, aryl, aralkyl, heteroaryl, heteroaralkyl, heterocyclyl, heterocyclylalkyl, each as defined herein, e.g., methylsulfonyl, phenylsulfonyl, benzylsulfonyl, pyridinylsulfonyl, and the like.

The phrase in the definition of groups $R^1$ and $R^2$ in the claims and in the specification of this Application " . . . wherein the aforementioned rings are optionally substituted with $R^a$, $R^b$, or $R^c$ independently selected from . . . " and similar phrases used for others groups [e.g., $Ar^1$ and $Ar^2$ groups] in the claims and in the specification with respect to the compound of Formula (I) and (IA)-(IF), means that the rings can be mono-, di-, or trisubstituted unless indicated otherwise.

"Treating" or "treatment" of a disease includes:
inhibiting the disease, i.e., arresting or reducing the development of the disease or its clinical symptoms; or
relieving the disease, i.e., causing regression of the disease or its clinical symptoms.

A "therapeutically effective amount" means the amount of a compound of Formula (I) that, when administered to a mammal for treating a disease, is sufficient to effect such treatment for the disease. The "therapeutically effective amount" will vary depending on the compound, the disease and its severity and the age, weight, etc., of the mammal to be treated.

Representative compounds of the Invention are shown in Tables 1-8 below:

Table 1 shows representative compounds of Formula (I) where $R^1$, $R^2$, $R^3$, $R^4$ and $R^5$ are hydrogen, $Ar^1$ and $Ar^2$ are phenyl where $Ar^2$ is substituted with $R^g$ and $R^h$ as shown below.

TABLE 1

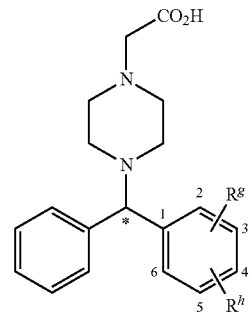

| Cpd # | $R^g$ | $R^h$ | Stereochem at *C | |
|---|---|---|---|---|
| 1 | 3-CF$_3$ | Absent | R | |
| 2 | 3-Br | Absent | RS | |
| 3 | 3-CF$_3$ | Absent | RS | |
| 4 | 3-Cl | 5-Cl | RS | |
| 5 | 3-CF$_3$ | Absent | S | |
| 6 | 4-Br | Absent | RS | |
| 7 | Absent | Absent | — | |
| 8 | 4-Cl | Absent | RS | 2 HCl |
| 9 | 4-CF$_3$ | Absent | RS | 2 HCl |
| 10 | 2-Br | Absent | RS | 2 HCl |
| 11 | 3-phenyl | Absent | RS | 2 HCl |
| 12 | 4-Br | Absent | S | 2 HCl |
| 13 | 4-Br | Absent | R | 2 HCl |
| 14 | 3-Br | Absent | S | 2 HCl |
| 15 | 3-Br | Absent | R | 2 HCl | and are named as:
(R)-2-(4-(phenyl(3-(trifluoromethyl)phenyl)methyl)piperazin-1-yl)acetic acid;
2-(4-((3-bromophenyl)(phenyl)methyl)piperazin-1-yl)acetic acid;
2-(4-(phenyl(3-(trifluoromethyl)phenyl)methyl)piperazin-1-yl)acetic acid;
2-(4-((3,5-dichlorophenyl)(phenyl)methyl)piperazin-1-yl)acetic acid;
(S)-2-(4-(phenyl(3-(trifluoromethyl)phenyl)methyl)piperazin-1-yl)acetic acid;
2-(4-((4-bromophenyl)(phenyl)methyl)piperazin-1-yl)acetic acid;
2-(4-benzhydrylpiperazin-1-yl)acetic acid;
2-(4-((4-chlorophenyl)(phenyl)methyl)piperazin-1-yl)acetic acid dihydrochloride salt;
2-(4-(phenyl(4-(trifluoromethyl)phenyl)methyl)piperazin-1-yl)acetic acid dihydrochloride salt;
2-(4-((2-bromophenyl)(phenyl)methyl)piperazin-1-yl)acetic acid dihydrochloride salt;
2-(4-((3-biphenyl)(phenyl)methyl)piperazin-1-yl)acetic acid dihydrochloride salt;
(S)-2-(4-((4-bromophenyl)(phenyl)methyl)piperazin-1-yl)acetic acid dihydrochloride salt;

(R)-2-(4-((4-bromophenyl)(phenyl)methyl)piperazin-1-yl) acetic acid dihydrochloride salt;

(S)-2-(4-((3-bromophenyl)(phenyl)methyl)piperazin-1-yl) acetic acid dihydrochloride salt; and (R)-2-(4-((3-bromophenyl)(phenyl)methyl)piperazin-1-yl) acetic acid dihydrochloride salt.

Table 2 shows representative compounds of Formula (I) where $R^1$ is (R)-methyl, $R^2$, $R^3$, $R^4$ and $R^5$ are hydrogen, $Ar^1$ and $Ar^2$ are phenyl where $Ar^2$ is substituted with $R^g$ and $R^h$ as shown below.

TABLE 2

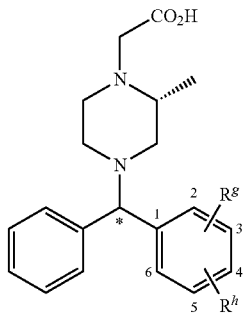

| Cpd. # | $R^g$ | $R^h$ | Stereochem at *C | |
|---|---|---|---|---|
| 16 | 3-CF$_3$ | Absent | RS | |
| 17 | 3-Br | Absent | RS | |
| 18 | Absent | Absent | (no stereo) | 2 HCl |
| 19 | 3-I | Absent | R | 2 HCl |
| 20 | 3-Br | Absent | R | 2 HCl |
| 21 | 3-Br | Absent | S | 2 HCl |
| 22 | 3-phenyl | Absent | RS | 2 HCl |
| 23 | 3-CF$_3$ | Absent | S | 2 HCl |
| 24 | 3-CF$_3$ | Absent | R | 2 HCl |
| 25 | 4-Cl | Absent | RS | 2 HCl |
| 26 | 4-phenyl | Absent | RS | 2 HCl |
| 27 | 4-Br | Absent | RS | 2 HCl |
| 28 | 4-CN | Absent | RS | |
| 29 | 3-Cl | Absent | RS | 2 HCl |
| 30 | 3-phenyl | Absent | R | |
| 31 | 3-SCH$_3$ | Absent | RS | |
| 32 | 2-Br | Absent | S | |
| 33 | 2-Br | Absent | R | |
| 34 | 3-CH$_3$ | Absent | R | |
| 35 | 3-CH(CH$_3$)$_2$ | Absent | R | |
| 36 | 4-F | Absent | RS | |
| 37 | 3-F | Absent | RS | |
| 38 | 3-thien-2yl | Absent | R | |
| 39 | 3-SCH$_3$ | Absent | R | |
| 40 | 3-SCH$_3$ | Absent | S | |
| 41 | 4-SCH$_3$ | Absent | R | |
| 42 | 2-F | Absent | S | |
| 43 | 2-F | Absent | R | |
| 44 | 3-OCF$_3$ | Absent | S | |
| 45 | 3-OCF$_3$ | Absent | R | |
| 46 | 4-phenyl | Absent | R | |
| 47 | 4-(2-CH$_3$phenyl) | Absent | R | |
| 48 | 4-(3-CH$_3$phenyl) | Absent | R | |
| 49 | 4-(4-CH$_3$phenyl) | Absent | R | |
| 50 | 2-F | 4-F | S | |
| 51 | 2-F | 4-F | R | |
| 52 | 4-F | Absent | S | |
| 53 | 4-F | Absent | R | |
| 54 | 3-F | Absent | S | |
| 55 | 3-F | Absent | R | |
| 55A | 4-(2-phenylethynyl) | Absent | R | |
| 55B | 4-(2-pyridin-3-ylethynyl) | Absent | R | |
| 55C | 4-(2-pyridin-4-ylethynyl) | Absent | R | | and are named as:

2-((R)-2-methyl-4-(phenyl(3-(trifluoromethyl)phenyl)methyl)piperazin-1-yl)acetic acid;

2-((R)-4-((3-bromophenyl)(phenyl)methyl)-2-methylpiperazin-1-yl)acetic acid;

(R)-2-(4-benzhydryl-2-methylpiperazin-1-yl)acetic acid dihydrochloride salt;

2-((R)-4-((R)-(3-iodophenyl)(phenyl)methyl)-2-methylpiperazin-1-yl)acetic acid dihydrochloride salt;

2-((R)-4-((R)-(3-bromophenyl)(phenyl)methyl)-2-methylpiperazin-1-yl)acetic acid dihydrochloride salt;

2-((R)-4-((S)-(3-bromophenyl)(phenyl)methyl)-2-methylpiperazin-1-yl)acetic acid dihydrochloride salt;

2-((R)-4-((R)-[1,1'-biphenyl]-3-yl(phenyl)methyl)-2-methylpiperazin-1-yl)acetic acid;

2-((R)-2-methyl-4-((S)-phenyl(3-(trifluoromethyl)phenyl)methyl)piperazin-1-yl)acetic acid dihydrochloride salt;

2-((R)-2-methyl-4-((R)-phenyl(3-(trifluoromethyl)phenyl)methyl)piperazin-1-yl)acetic acid dihydrochloride salt;

2-((R)-4-((4-chlorophenyl)(phenyl)methyl)-2-methylpiperazin-1-yl)acetic acid dihydrochloride salt;

2-((R)-2-methyl-4-(biphenyl-4-yl-phenyl-methyl)-piperazin-1-yl)-acetic acid dihydrochloride salt;

2-((R)-4-((4-bromophenyl)(phenyl)methyl)-2-methylpiperazin-1-yl)acetic acid dihydrochloride salt;

2-((R)-4-((4-cyanophenyl)(phenyl)methyl)-2-methylpiperazin-1-yl)acetic acid;

2-((R)-4-((3-chlorophenyl)(phenyl)methyl)-2-methylpiperazin-1-yl)acetic acid dihydrochloride salt;

[(R)-4-((R)-biphenyl-3-yl-phenyl-methyl)-2-methyl-piperazin-1-yl]-acetic acid;

2-((R)-2-methyl-4-((3-(methylthio)phenyl)(phenyl)methyl)piperazin-1-yl)acetic acid;

2-((R)-4-((S)-(2-bromophenyl)(phenyl)methyl)-2-methylpiperazin-1-yl)acetic acid;

2-((R)-4-((R)-(2-bromophenyl)(phenyl)methyl)-2-methylpiperazin-1-yl)acetic acid;

2-((R)-2-methyl-4-((R)-phenyl(m-tolyl)methyl)piperazin-1-yl)acetic acid;

2-((R)-4-((R)-(3-isopropylphenyl)(phenyl)methyl)-2-methylpiperazin-1-yl)acetic acid;

2-((R)-4-((4-fluorophenyl)(phenyl)methyl)-2-methylpiperazin-1-yl)acetic acid;

2-((R)-4-((3-fluorophenyl)(phenyl)methyl)-2-methylpiperazin-1-yl)acetic acid;

2-((R)-2-methyl-4-((R)-phenyl(3-(thiophen-2-yl)phenyl)methyl)piperazin-1-yl)acetic acid;

2-((R)-2-methyl-4-((R)-(3-(methylthio)phenyl)(phenyl)methyl)piperazin-1-yl)acetic acid;

2-((R)-2-methyl-4-((S)-(3-(methylthio)phenyl)(phenyl)methyl)piperazin-1-yl)acetic acid;

2-((R)-2-methyl-4-((R)-(4-(methylthio)phenyl)(phenyl)methyl)piperazin-1-yl)acetic acid;

2-((R)-4-((S)-(2-fluorophenyl)(phenyl)methyl)-2-methylpiperazin-1-yl)acetic acid;

2-((R)-4-((R)-(2-fluorophenyl)(phenyl)methyl)-2-methylpiperazin-1-yl)acetic acid;

2-((R)-2-methyl-4-((S)-phenyl(3-(trifluoromethoxy)phenyl)methyl)piperazin-1-yl)acetic acid;

2-((R)-2-methyl-4-((R)-phenyl(3-(trifluoromethoxy)phenyl)methyl)piperazin-1-yl)acetic acid;

[(R)-4-((R)-biphenyl-4-yl-phenyl-methyl)-2-methyl-piperazin-1-yl]-acetic acid;

[(R)-2-methyl-4-[(R)-(2'-methyl-biphenyl-4-yl)-phenyl-methyl]-piperazin-1-yl]-acetic acid;

[(R)-2-methyl-4-[(R)-(3'-methyl-biphenyl-4-yl)-phenyl-methyl]-piperazin-1-yl]-acetic acid;

[(R)-2-methyl-4-[(R)-(4'-methyl-biphenyl-4-yl)-phenyl-methyl]-piperazin-1-yl]-acetic acid;

2-((R)-4-((S)-(2,4-difluorophenyl)(phenyl)methyl)-2-methylpiperazin-1-yl)acetic acid;

2-((R)-4-((R)-(2,4-difluorophenyl)(phenyl)methyl)-2-methylpiperazin-1-yl)acetic acid;

2-((R)-4-((S)-(4-fluorophenyl)(phenyl)methyl)-2-methylpiperazin-1-yl)acetic acid;

2-((R)-4-((R)-(4-fluorophenyl)(phenyl)methyl)-2-methylpiperazin-1-yl)acetic acid;

2-((R)-4-((S)-(3-fluorophenyl)(phenyl)methyl)-2-methylpiperazin-1-yl)acetic acid;

2-((R)-4-((R)-(3-fluorophenyl)(phenyl)methyl)-2-methylpiperazin-1-yl)acetic acid;

2-((R)-2-methyl-4-((R)-phenyl(4-(2-phenylethynyl)phenyl)methyl)piperazin-1-yl)acetic acid;

2-((R)-2-methyl-4-((R)-phenyl(3-(2-pyridin-3-ylethynyl)phenyl)methyl)-piperazin-1-yl)acetic acid; and 2-((R)-2-methyl-4-((R)-phenyl(3-(2-pyridin-4-ylethynyl)phenyl)methyl)-piperazin-1-yl)acetic acid.

Table 3 shows representative compounds of Formula (I) where $R^1$ is (S)-methyl, $R^2$, $R^3$, $R^4$ and $R^5$ are hydrogen, $Ar^1$ and $Ar^2$ are phenyl where $Ar^2$ is substituted with $R^g$ and $R^h$ as shown below.

TABLE 3

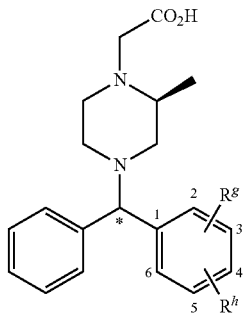

| Cpd # | $R^g$ | $R^h$ | Stereochem at *C | |
|---|---|---|---|---|
| 56 | Absent | Absent | (no stereo) | 2 HCl |
| 57 | 3-CF₃ | Absent | RS | 2 HCl | and are named as:

(S)-2-(4-benzhydryl-2-methylpiperazin-1-yl)acetic acid dihydrochloride salt; and 2-((S)-2-methyl-4-(phenyl(3-(trifluoromethyl)phenyl)methyl)piperazin-1-yl)acetic acid dihydrochloride salt.

Table 4 shows representative compounds of Formula (I) where $R^3$, $R^4$ and $R^5$ are hydrogen, $Ar^1$ and $Ar^2$ are phenyl where $Ar^2$ is substituted with $R^g$ and $R^h$ as shown below and $R^1$ and $R^2$ are as shown below.

TABLE 4

| Cpd # | $R^1$ | $R^2$ | $R^g$ | $R^h$ | Stereochem at *C | |
|---|---|---|---|---|---|---|
| 58 | H | 3S—CH₃ | Absent | Absent | (no stereo) | 2 HCl |
| 59 | H | 3R—CH₃ | Absent | Absent | (no stereo) | 2 HCl |
| 60 and 62 as a mixture of two enantiomers (both are trans-dimethyl) | 2R—CH₃ | 5S—CH₃ | Absent | Absent | (no stereo) | 2 HCl |
| 62 | 2S—CH₃ | 5R—CH₃ | Absent | Absent | (no stereo) | 2 HCl |
| 63 | H | 3R—CH₃ | 4-phenyl | Absent | RS | | and are named as:

(S)-2-(4-benzhydryl-3-methylpiperazin-1-yl)acetic acid dihydrochloride salt;

(R)-2-(4-benzhydryl-3-methylpiperazin-1-yl)acetic acid dihydrochloride salt;

2-((2,5-trans)-4-benzhydryl-2,5-dimethylpiperazin-1-yl) acetic acid dihydrochloride salt;

2-((2,5-cis)-4-benzhydryl-2,5-dimethylpiperazin-1-yl)acetic acid dihydrochloride salt; and 2-(4-([1,1'-biphenyl]-4-yl(phenyl)methyl)-3-methylpiperazin-1-yl)acetic acid Table 5 shows representative compounds of Formula (I) where $R^1$ is shown below, $R^2$, $R^3$, $R^4$ and $R^5$ are hydrogen, $Ar^1$ and $Ar^2$ are phenyl where $Ar^1$ is substituted with $R^g$ and $Ar^2$ is substituted with $R^h$ as shown below.

TABLE 5

| Cpd # | $R^g$ | $R^h$ | $R^1$ | Stereochem at *C |
|---|---|---|---|---|
| 64 | 3-Cl | 3-Cl | 2R—CH₃ | (no stereo) |
| 65 | 3-F | 3-F | 2R—CH₃ | (no stereo) |

TABLE 5-continued

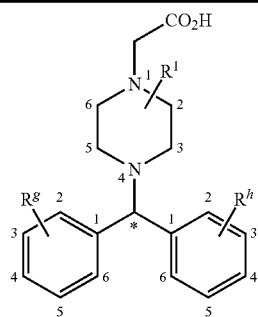

| Cpd # | $R^g$ | $R^h$ | $R^1$ | Stereochem at *C | |
|---|---|---|---|---|---|
| 66 | 4-CF$_3$ | 3-CF$_3$ | H | RS | |
| 67 | 4-F | 3-phenyl | 2R—CH$_3$ | RS | 2 HCl |
| 68 | 4-Cl | 4-Cl | 2R—CH$_3$ | (no stereo) | 2 HCl |
| 69 | 4-F | 3-Br | 2R—CH$_3$ | RS | 2 HCl |
| 70 | 4-F | 4-F | 3R—CH$_3$ | (no stereo) | 2 HCl |
| 71 | 4-F | 4-F | 2-R—CH$_3$ | (no stereo) | |
| 72 | 3-CF$_3$ | 3-CF$_3$ | 2-R—CH$_3$ | (no stereo) | |
| 73 | 3-CF$_3$ | 3-CF$_3$ | H | (no stereo) | | and are named as:

(R)-2-(4-(bis(3-chlorophenyl)methyl)-2-methylpiperazin-1-yl)acetic acid;

(R)-2-(4-(bis(3-fluorophenyl)methyl)-2-methylpiperazin-1-yl)acetic acid;

2-(4-((3-(trifluoromethyl)phenyl)(4-(trifluoromethyl)phenyl)methyl)piperazin-1-yl)acetic acid;

2-(4-((4-fluorophenyl)(3-(diphenyl)methyl))-(R)-2-methylpiperazin-1-yl)acetic acid dihydrochloride salt;

(R)-2-(4-(bis(4-chlorophenyl)methyl)-2-methylpiperazin-1-yl)acetic acid dihydrochloride salt;

2-((R)-4-((3-bromophenyl)(4-fluorophenyl)methyl)-2-methylpiperazin-1-yl)acetic acid dihydrochloride salt;

(R)-2-(4-(bis(4-fluorophenyl)methyl)-3-methylpiperazin-1-yl)acetic acid dihydrochloride salt;

(R)-2-(4-(bis(4-fluorophenyl)methyl)-2-methylpiperazin-1-yl)acetic acid;

(R)-2-(4-(bis(3-(trifluoromethyl)phenyl)methyl)-2-methylpiperazin-1-yl)acetic acid; and 2-(4-(bis(3-(trifluoromethyl)phenyl)methyl)piperazin-1-yl) acetic acid.

Table 6 shows representative compounds of Formula (I) where $R^1$ is (R)-methyl, $R^2$, $R^3$, $R^4$ and $R^5$ are hydrogen, Ar$^1$ and Ar$^2$ are as shown below.

TABLE 6

| Cpd. # | Ar$^1$ | Ar$^2$ | Stereochem. at *C | |
|---|---|---|---|---|
| 74 | thien-2-yl | 3-CF$_3$phenyl | RS | |
| 75 | thien-2-yl | 3-CF$_3$phenyl | R | |
| 76 | thien-2-yl | 3-CF$_3$phenyl | S | |
| 77 | cyclopropyl | 3-CF$_3$phenyl | RS | 2 HCl | and are named as:

2-((R)-2-methyl-4-(thiophen-2-yl(3-(trifluoromethyl)phenyl)methyl)-piperazin-1-yl)acetic acid;

2-((R)-2-methyl-4-((R)-thiophen-2-yl(3-(trifluoromethyl)phenyl)methyl)-piperazin-1-yl)acetic acid;

2-((R)-2-methyl-4-((S)-thiophen-2-yl(3-(trifluoromethyl)phenyl)methyl)-piperazin-1-yl)acetic acid; and 2-((R)-4-(cyclopropyl(3-(trifluoromethyl)phenyl)methyl)-2-methylpiperazin-1-yl)acetic acid dihydrochloride salt.

Table 7 shows representative compounds of Formula (I) where $R^5$ and $R^3$ are hydrogen, Ar$^1$ and Ar$^2$ are each 4-Clphenyl and $R^1$, $R^2$, and $R^4$ are as shown below.

TABLE 7

| Cpd # | $R^4$ | $R^1$ | $R^2$ | $R^1 + R^2$ | |
|---|---|---|---|---|---|
| 78 | H | H | 2(R)—CH$_3$ | | |
| 79 | (S)—CH$_3$ | H | 3(R)—CH$_3$ | | |
| 80 | H | | | 3- =(O) | |
| 81 | (S)—CH$_3$ | H | 2(R)—CH$_3$ | | |
| 82 | (R)—CH$_3$ | H | 2(R)—CH$_3$ | | |
| 83 | H | H | | 2- =(O) | |
| 84 | H | 6(S)—CH$_3$ | 2(R)—CH$_3$ | | 2 HCl |
| 85 | H | 2-CH$_3$ | 2-CH$_3$ | | 2 HCl |
| 86 | —CH$_3$ | H | H | | 2 HCl |
| 87 | H | H | 2(R)—CH(CH$_3$)$_2$ | | 2 HCl |
| 88 | H | H | H | | 2 HCl | and are named as:

(R)-2-(4-(bis(4-chlorophenyl)methyl)-2-methylpiperazin-1-yl)acetic acid;

(S)-2-((R)-4-(bis(4-chlorophenyl)methyl)-3-methylpiperazin-1-yl)propanoic acid;

2-(4-(bis(4-chlorophenyl)methyl)-3-oxopiperazin-1-yl)acetic acid;

(S)-2-((R)-4-(bis(4-chlorophenyl)methyl)-2-methylpiperazin-1-yl)propanoic acid;

(R)-2-((R)-4-(bis(4-chlorophenyl)methyl)-2-methylpiperazin-1-yl)propanoic acid;

2-(4-(bis(4-chlorophenyl)methyl)-2-oxopiperazin-1-yl)acetic acid;

2-((2R,6S)-4-(bis(4-chlorophenyl)methyl)-2,6-dimethylpiperazin-1-yl)acetic acid dihydrochloride salt;

2-(4-(bis(4-chlorophenyl)methyl)-2,2-dimethylpiperazin-1-yl)acetic acid dihydrochloride salt;

2-(4-(bis(4-chlorophenyl)methyl)piperazin-1-yl)propanoic acid dihydrochloride salt;

(R)-2-(4-(bis(4-chlorophenyl)methyl)-2-isopropylpiperazin-1-yl)acetic acid dihydrochloride salt; and 2-(4-(bis(4-chlorophenyl)methyl)piperazin-1-yl)acetic acid dihydrochloride salt.

TABLE 8

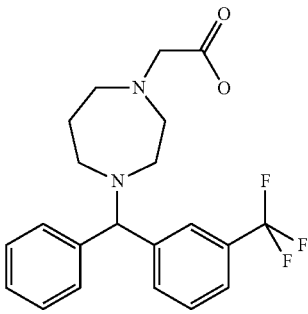 [SMILES: O=C(O)CN1CCCN(C(c2ccccc2)c2cccc(C(F)(F)F)c2)CC1]

and is named as:
2-(4-(phenyl(3-(trifluoromethyl)phenyl)methyl)-1,4-diazepan-1-yl)-acetic acid.

Embodiments (A) In one embodiment, the compound of Formula (I) has the structure represented by Formula (IA):

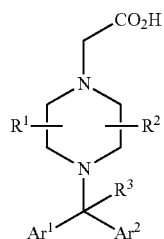

(IA)

where:
R$^1$ and R$^2$ are independently selected from hydrogen, alkyl, haloalkyl, alkoxy, haloalkoxy, aryl, heteroaryl, cycloalkyl, or heterocyclyl wherein the aforementioned rings are optionally substituted with R$^a$, R$^b$, or R$^c$ independently selected from alkyl, halo, haloalkyl, alkoxy, haloalkoxy, hydroxy, cyano, monosubstituted amino, or disubstituted amino;

Ar$^1$ and Ar$^2$ are independently aryl, heteroaryl, cycloalkyl, or heterocyclyl where each of the aforementioned ring is optionally substituted with R$^g$, R$^h$ or R$^i$ where R$^g$ is alkyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, or acylamino and R$^h$ and R$^i$ are independently selected from alkyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, acylamino, aryl, heteroaryl, cycloalkyl, or heterocyclyl where the aromatic or alicyclic ring in R$^g$, R$^h$ and R$^i$ is optionally substituted with R$^j$, R$^k$ or R$^l$ which are independently selected from alkyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, or acylamino; and
other groups are as defined in the Summary of the Invention.

Within this group (A), one group of compounds is that wherein R$^1$ and R$^2$ are independently selected from hydrogen, alkyl, haloalkyl, alkoxy, or haloalkoxy provided that at least one of R$^1$ and R$^2$ is other than hydrogen.

Within this group (A), another group of compounds is that wherein R$^1$ and R$^2$ are independently selected from hydrogen, alkyl, haloalkyl, alkoxy, or haloalkoxy.

Within this group (A), another group of compounds is that wherein R$^1$ and R$^2$ are independently selected from hydrogen, methyl, ethyl, propyl, trifluoromethyl, 2,2,2-trifluoroethyl, methoxy, ethoxy, propoxy, trifluoromethoxy, difluoromethoxy, or 2,2,2-trifluoroethoxy.

Within this group (A), another group of compounds is that wherein R$^1$ and R$^2$ are hydrogen.

Within this group (A), another group of compounds is that wherein R$^1$ is hydrogen and R$^2$ are alkyl.

Within this group (A), another group of compounds is that wherein R$^1$ is hydrogen and R$^2$ are methyl.

Within this group (A), yet another group of compounds is that wherein R$^1$ is hydrogen and R$^2$ is methyl, ethyl, propyl, trifluoromethyl, 2,2,2-trifluoroethyl, methoxy, ethoxy, propoxy, trifluoromethoxy, difluoromethoxy, or 2,2,2-trifluoroethoxy and is located at the carbon atom that is ortho to the piperazine nitrogen atom that is substituted with the carboxymethyl group.

Within this group (A), yet another group of compounds is that wherein R$^1$ is hydrogen and R$^2$ is methyl, ethyl, propyl, trifluoromethyl, 2,2,2-trifluoroethyl, methoxy, ethoxy, propoxy, trifluoromethoxy, difluoromethoxy, or 2,2,2-trifluoroethoxy and is located at the carbon atom that is ortho to the piperazine nitrogen atom that is substituted with the carboxymethyl group and the stereochemistry at the carbon atom carrying the R$^2$ group is (R).

Within this group (A), yet another group of compounds is that wherein R$^1$ is hydrogen and R$^2$ is methyl and is located at the carbon atom that is ortho to the piperazine nitrogen atom that is substituted with the carboxymethyl group and the stereochemistry at the carbon atom carrying the R$^2$ group is (R).

Within this group (A), yet another group of compounds is that wherein R$^1$ is hydrogen and R$^2$ is methyl, ethyl, propyl, trifluoromethyl, 2,2,2-trifluoroethyl, methoxy, ethoxy, propoxy, trifluoromethoxy, difluoromethoxy, or 2,2,2-trifluoroethoxy and is located at the carbon atom that is ortho to the piperazine nitrogen atom that is substituted with the carboxymethyl group and the stereochemistry at the carbon atom carrying the R$^2$ group is (S).

Within this group (A), another group of compounds is that wherein R$^1$ and R$^2$ are independently selected from methyl, ethyl, propyl, trifluoromethyl, 2,2,2-trifluoroethyl, methoxy, ethoxy, propoxy, trifluoromethoxy, difluoromethoxy, or 2,2,2-trifluoroethoxy.

Within this group (A), another group of compounds is that wherein R$^1$ and R$^2$ are independently selected from methyl, ethyl, propyl, trifluoromethyl, 2,2,2-trifluoroethyl, methoxy, ethoxy, propoxy, trifluoromethoxy, difluoromethoxy, or 2,2,2-trifluoroethoxy where R$^1$ is located at the carbon atom that is ortho to the piperazine nitrogen atom that is substituted with the carboxymethyl group and R$^2$ is located at carbon that is para to the carbon atom carrying the R$^1$ group.

Within this group (A), another group of compounds is that wherein R$^1$ and R$^2$ are independently selected from methyl, ethyl, propyl, trifluoromethyl, 2,2,2-trifluoroethyl, methoxy, ethoxy, propoxy, trifluoromethoxy, difluoromethoxy, or 2,2,2-trifluoroethoxy where R$^1$ is located at the carbon atom that is ortho to the piperazine nitrogen atom that is substituted with the carboxymethyl group and R$^2$ is located at carbon that is para to the carbon atom carrying the $R^1$ group and the stereochemistry at the carbon atoms carrying the $R^1$ and $R^2$ groups are (R,S), (R,R), (S,R) or (S,S).

Within this group (A), yet another group of compounds is that wherein $R^1$ is hydrogen and $R^2$ is aryl, heteroaryl, cycloalkyl, or heterocyclyl wherein the aforementioned rings are optionally substituted with $R^a$, $R^b$, or $R^c$ independently selected from alkyl, halo, haloalkyl, alkoxy, haloalkoxy, hydroxy, cyano, monosubstituted amino, or disubstituted amino (B) In another embodiment, the compound of Formula (I) has the structure represented by Formula (IB):

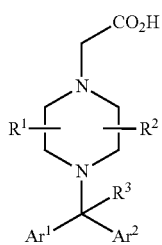

(IB)

wherein:

$R^1$ and $R^2$ together from an oxo group;

$Ar^1$ and $Ar^2$ are independently aryl, heteroaryl, cycloalkyl, or heterocyclyl where each of the aforementioned ring is optionally substituted with $R^g$, $R^h$ or $R^i$ where $R^g$ is alkyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, or acylamino and $R^h$ and $R^i$ are independently selected from alkyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, acylamino, aryl, heteroaryl, cycloalkyl, or heterocyclyl where the aromatic or alicyclic ring in $R^g$, $R^h$ and $R^i$ is optionally substituted with $R^j$, $R^k$ or $R^l$ which are independently selected from alkyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, or acylamino; and other groups are as defined in the Summary of the Invention.

Within this group (B), one group of compounds is that wherein the oxo group is located at the carbon atom that is ortho to the piperazine nitrogen atom that is substituted with the carboxymethyl group.

(C) In another embodiment, the compound of Formula (I) has the structure represented by Formula (IC):

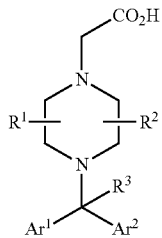

(IC)

wherein:

$R^1$ and $R^2$ are attached to the same carbon atom and are combined to form cycloalkyl optionally substituted with $R^d$, $R^e$ or $R^f$ independently selected from alkyl, alkoxy, fluoro, fluoroalkyl, fluoroalkoxy, hydroxy, monosubstituted amino, or disubstituted amino;

$Ar^1$ and $Ar^2$ are independently aryl, heteroaryl, cycloalkyl, or heterocyclyl where each of the aforementioned ring is optionally substituted with $R^g$, $R^h$ or $R^i$ where $R^g$ is alkyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, or acylamino and $R^h$ and $R^i$ are independently selected from alkyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, acylamino, aryl, heteroaryl, cycloalkyl, or heterocyclyl where the aromatic or alicyclic ring in $R^g$, $R^h$ and $R^i$ is optionally substituted with $R^j$, $R^k$ or $R^l$ which are independently selected from alkyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, or acylamino; and other groups are as defined in the Summary of the Invention.

Within this group (C), one group of compounds is that wherein $R^1$ and $R^2$ combine to form cyclopropyl, cyclobutyl, cyclopentyl, or cyclohexyl ring optionally substituted with $R^d$ or $R^e$ independently selected from alkyl, hydroxy, or fluoro.

(D) In another embodiment, the compound of Formula (I) has the structure represented by Formula (ID):

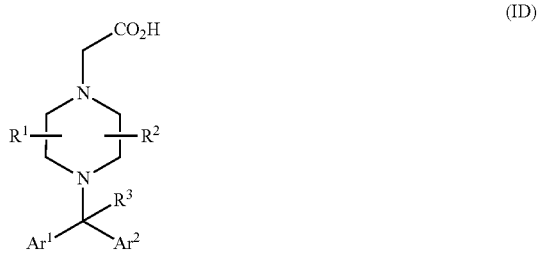

(ID)

wherein:

$R^1$ and $R^2$ are attached to the same carbon atom and are combined to form monocyclic saturated heterocyclyl which are optionally substituted with $R^d$, $R^e$ or $R^f$ independently selected from alkyl, alkoxy, fluoro, fluoroalkyl, fluoroalkoxy, hydroxy, monosubstituted amino, or disubstituted amino;

$Ar^1$ and $Ar^2$ are independently aryl, heteroaryl, cycloalkyl, or heterocyclyl where each of the aforementioned ring is optionally substituted with $R^g$, $R^h$ or $R^i$ where $R^g$ is alkyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, or acylamino and $R^h$ and $R^i$ are independently selected from alkyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, acylamino, aryl, heteroaryl, cycloalkyl, or heterocyclyl where the aromatic or alicyclic ring in $R^g$, $R^h$ and $R^i$ is optionally substituted with $R^j$, $R^k$ or $R^l$ which are independently selected from alkyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, or acylamino; and other groups are as defined in the Summary of the Invention.

Within this group (D), one group of compounds is that wherein $R^1$ and $R^2$ combine to form tetrahydrofuranyl, tetrahydropyranyl, piperidinyl, or pyrrolidinyl where each ring is optionally substituted with $R^d$ or $R^e$ independently selected from one or two alkyl, hydroxy, or fluoro.

(E) In another embodiment, the compound of Formula (I) has the structure represented by Formula (IE):

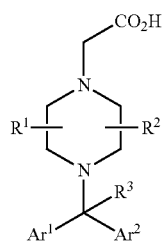

(IE)

wherein:

$R^1$ and $R^2$ are attached to carbon atoms 2 and 5 or 3 and 6 positions of the piperazine ring, and are combined to form —$C_1$-$C_2$— alkylene chain wherein one or two hydrogen atoms in the alkylene chain can be optionally substituted with one or two alkyl;

$Ar^1$ and $Ar^2$ are independently aryl, heteroaryl, cycloalkyl, or heterocyclyl where each of the aforementioned ring is optionally substituted with $R^g$, $R^h$ or $R^i$ where $R^g$ is alkyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, or acylamino and $R^h$ and $R^i$ are independently selected from alkyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, acylamino, aryl, heteroaryl, cycloalkyl, or heterocyclyl where the aromatic or alicyclic ring in $R^g$, $R^h$ and $R^i$ is optionally substituted with $R^j$, $R^k$ or $R^l$ which are independently selected from alkyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, or acyl; and other groups are as defined in the Summary of the Invention.

(F) In another embodiment, the compound of Formula (I) has the structure represented by Formula (IF):

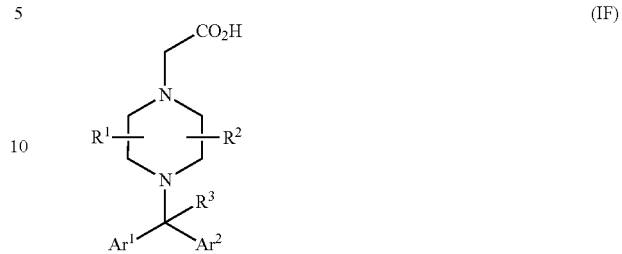

wherein:

$R^1$ and $R^2$ are attached to carbon atoms 2 and 5 or 3 and 6 positions of the piperazine ring and are combined to form —$C_1$-$C_3$— alkylene chain wherein one of the carbon atoms in the alkylene chain is replaced by a —NR—, —O—, —S(O)n1- (where R is hydrogen or alkyl and n1 is 0-2) and further wherein one or two hydrogen atoms in the alkylene chain can be optionally substituted with one or two alkyl;

$Ar^1$ and $Ar^2$ are independently aryl, heteroaryl, cycloalkyl, or heterocyclyl where each of the aforementioned ring is optionally substituted with $R^g$, $R^h$ or $R^i$ where $R^g$ is alkyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, or acylamino and $R^h$ and $R^i$ are independently selected from alkyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, acylamino, aryl, heteroaryl, cycloalkyl, or heterocyclyl where the aromatic or alicyclic ring in $R^g$, $R^h$ and $R^i$ is optionally substituted with $R^j$, $R^k$ or $R^l$ which are independently selected from alkyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, or acylamino; and other groups are as defined in the Summary of the Invention.

Within this group (F), one group of compounds is that wherein $R^1$ and $R^2$ are attached to carbon atoms 2 and 5 or 3 and 6 positions of the piperazine ring, and are combined to form —$C_1$-$C_2$— alkylene wherein one of the carbon is replace by represented by —NR— (where R is hydrogen or alkyl).

(a) Within the embodiments (A)-(F) above and groups contained therein, one group of compounds is that wherein $R^3$ is hydrogen. Within this group, one group of compounds is that wherein the stereochemistry at the carbon atom carrying the $R^3$ group is (S). Within this group, one group of compounds is that wherein the stereochemistry at the carbon atom carrying the $R^3$ group is (R).

(b) Within the embodiments (A)-(F) above and groups contained therein, another group of compounds is that wherein $R^3$ is alkyl, preferably methyl or ethyl. Within this group, one group of compounds is that wherein the stereochemistry at the carbon atom carrying the $R^3$ group is (5). Within this group, one group of compounds is that wherein the stereochemistry at the carbon atom carrying the $R^3$ group is (R).

(c) Within the embodiments (A)-(F) above and groups contained therein, yet another group of compounds is that wherein $R^3$ is fluoro. Within this group, one group of compounds is that wherein the stereochemistry at the carbon atom carrying the $R^3$ group is (5). Within this group, one group of compounds is that wherein the stereochemistry at the carbon atom carrying the $R^3$ group is (R).

(d) Within the embodiments (A)-(F) above and groups contained therein, yet another group of compounds is that wherein $R^3$ is fluoroalkyl, preferably difluoromethyl or trifluoromethyl. Within this group, one group of compounds is that wherein the stereochemistry at the carbon atom carrying the $R^3$ group is (5). Within this group, one group of compounds is that wherein the stereochemistry at the carbon atom carrying the $R^3$ group is (R).

(i) Within the embodiments (A)-(F), (a)-(d) and groups contained therein, and groups formed as a result of combination of groups (A)-(F) with (a)-(d), one group of compounds is that wherein $Ar^1$ and $Ar^2$ are phenyl, each phenyl optionally substituted as defined above.

Within this embodiment (i), one group of compounds is that wherein $Ar^1$ and $Ar^2$ are phenyl. Within this embodiment, another group of compounds is that wherein $Ar^1$ is phenyl and $Ar^2$ is phenyl substituted with $R^g$ selected from alkyl, halo, haloalkyl, haloalkoxy, preferably methyl, fluoro, chloro, trifluoromethyl, trifluoromethoxy or 2,2,2-trifluoroethoxy.

Within this embodiment (i), another group of compounds is that wherein $Ar^1$ is phenyl and $Ar^2$ is phenyl substituted with $R^g$ selected from alkyl, halo, haloalkyl, haloalkoxy, preferably methyl, fluoro, chloro, trifluoromethyl, trifluoromethoxy or 2,2,2-trifluoroethoxy and $R^g$ is located at the 3-position of the phenyl ring, the carbon atom attached to the —$CR^3Ar^1$ group being the 1-position.

Within this embodiment (i), another group of compounds is that wherein $Ar^1$ is phenyl substituted with $R^g$ selected from alkyl, halo, haloalkyl, haloalkoxy, preferably methyl, fluoro, chloro, trifluoromethyl, trifluoromethoxy or 2,2,2-trifluoroethoxy, preferably $R^g$ is located at the 3-position of the phenyl ring and $Ar^2$ is phenyl substituted with $R^h$ selected from alkyl, halo, haloalkyl, haloalkoxy, preferably methyl, fluoro, chloro, trifluoromethyl, trifluoromethoxy or 2,2,2-trifluoroethoxy, preferably $R^h$ is located at the 3-position of the phenyl ring.

(ii) Within the embodiments (A)-(F), (a)-(d) and groups contained therein, and groups formed as a result of combination of groups (A)-(F) with (a)-(d), another group of compounds is that wherein $Ar^1$ is phenyl and $Ar^2$ is heteroaryl, each ring optionally substituted as defined above.

Within this embodiment (ii), one group of compounds is that wherein $Ar^1$ is phenyl and $Ar^2$ is pyridinyl, pyrimidinyl, pyridazinyl, pyrazinyl, or thienyl, each $Ar^1$ and $Ar^2$ optionally substituted as defined above.

Within this embodiment (ii), another group of compounds is that wherein $Ar^1$ is phenyl and $Ar^2$ is pyridinyl, pyrimidinyl, pyridazinyl, pyrazinyl, or thienyl optionally substituted with $R^g$ or $R^h$ independently selected from alkyl, halo, haloalkyl, haloalkoxy, preferably methyl, fluoro, chloro, trifluoromethyl, trifluoromethoxy or 2,2,2-trifluoroethoxy.

Within this embodiment (ii), another group of compounds is that wherein $Ar^1$ is phenyl optionally substituted with $R^g$ or $R^h$ independently selected from alkyl, halo, haloalkyl, haloalkoxy, preferably methyl, fluoro, chloro, trifluoromethyl, trifluoromethoxy or 2,2,2-trifluoroethoxy and $Ar^2$ is pyridinyl, pyrimidinyl, pyridazinyl, pyrazinyl, or thienyl, preferably thienyl.

(iii) Within the embodiments (A)-(F), (a)-(d) above and groups contained therein, and groups formed as a result of combination of groups (A)-(F) with (a)-(d), another group of compounds is that wherein $Ar^1$ is phenyl and $Ar^2$ is heterocyclyl, each $Ar^1$ and $Ar^2$ optionally substituted as defined above provided that $Ar^2$ is not pyrimidin-4(3H)-one that is fused to a five membered heteroaryl ring and is optionally substituted as defined above.

Within this embodiment (iii), one group of compounds is that wherein $Ar^1$ is phenyl and $Ar^2$ is tetrahydropyranyl, piperidinyl, or tetrahydrofuranyl, each $Ar^1$ and $Ar^2$ optionally substituted as defined above.

Within this embodiment (iii), one group of compounds is that wherein $Ar^1$ is phenyl and $Ar^2$ is tetrahydropyranyl, piperidinyl, or tetrahydrofuranyl optionally substituted with $R^g$ or $R^h$ independently selected from alkyl, halo, haloalkyl, haloalkoxy, preferably methyl, fluoro, chloro, trifluoromethyl, trifluoromethoxy or 2,2,2-trifluoroethoxy. Within this group, another group of compounds is that wherein $Ar^1$ is phenyl optionally substituted with $R^g$ or $R^h$ independently selected from alkyl, halo, haloalkyl, haloalkoxy, preferably methyl, fluoro, chloro, trifluoromethyl, trifluoromethoxy or 2,2,2-trifluoroethoxy and $Ar^2$ is tetrahydropyranyl, piperidinyl, or furanyl.

(iv) Within the embodiments (A)-(F), (a)-(d) and groups contained therein, and groups formed as a result of combination of groups (A)-(F) with (a)-(d), another group of compounds is that wherein $Ar^1$ is phenyl and $Ar^2$ is cycloalkyl, each $Ar^1$ and $Ar^2$ optionally substituted as defined above.

Within this embodiment (iv), one group of compounds is that wherein $Ar^1$ is phenyl and $Ar^2$ is cyclopentyl or cyclohexyl, each $Ar^1$ and $Ar^2$ optionally substituted as defined above.

Within this embodiment (iv), one group of compounds is that wherein $Ar^1$ is phenyl and $Ar^2$ is cyclopentyl or cyclohexyl, each $Ar^1$ and $Ar^2$ optionally substituted with $R^g$ or $R^h$ independently selected from alkyl, halo, haloalkyl, haloalkoxy, preferably methyl, fluoro, chloro, trifluoromethyl, trifluoromethoxy or 2,2,2-trifluoroethoxy.

Within this embodiment (iv), one group of compounds is that wherein $Ar^1$ is phenyl and $Ar^2$ is cyclopropyl, $Ar^1$ optionally substituted as defined above.

Within this embodiment (iv), one group of compounds is that wherein $Ar^1$ is phenyl and $Ar^2$ is cyclopropyl, $Ar^1$ optionally substituted with $R^g$ or $R^h$ independently selected from alkyl, halo, haloalkyl, haloalkoxy, preferably methyl, fluoro, chloro, trifluoromethyl, trifluoromethoxy or 2,2,2-trifluoroethoxy.

(v) Within the embodiments (A)-(F), (a)-(d) and groups contained therein, and groups formed as a result of combination of groups (A)-(F) with (a)-(d), another group of compounds is that wherein $Ar^1$ and $Ar^2$ are heteroaryl optionally substituted as defined above.

Within this embodiment (v), one group of compounds is that wherein $Ar^1$ and $Ar^2$ are heteroaryl each optionally substituted with $R^g$ or $R^h$ independently selected from alkyl, halo, haloalkyl, haloalkoxy, preferably methyl, fluoro, chloro, trifluoromethyl, trifluoromethoxy or 2,2,2-trifluoroethoxy.

(vi) Within the embodiments (A)-(F), (a)-(d) and groups contained therein, and groups formed as a result of combination of groups (A)-(F) with (a)-(d), another group of compounds is that wherein $Ar^1$ is heteroaryl and $Ar^2$ is cycloalkyl each $Ar^1$ and $Ar^2$ optionally substituted as defined above.

(vii) Within the embodiments (A)-(F), (a)-(d) and groups contained therein, one group of compounds is that wherein $Ar^1$ is heterocyclyl and $Ar^2$ is heteroaryl each $Ar^1$ and $Ar^2$ optionally substituted as defined above.

(viii) Within the embodiments (A)-(F), (a)-(d) and groups contained therein, one group of compounds is that wherein Ar$^1$ is cycloalkyl and Ar$^2$ is heterocyclyl each Ar$^1$ and Ar$^2$ optionally substituted as defined above.

(ix) Within the embodiments (A)-(F), (a)-(d) and groups contained therein, one group of compounds is that wherein Ar$^1$ is cycloalkyl and Ar$^2$ is cycloalkyl each Ar$^1$ and Ar$^2$ optionally substituted as defined above.

The above embodiments, include all combinations of individual groups and subs-groups contained therein e.g., each group and subgroups contained within groups (A) to (F), can be combined independently with each group and sub-group contained within group (a)-(d) and (i)-(ix) and each group formed as a result of combination of groups (a)-(d) and (i)-(ix).

(G) In another embodiment, this invention is directed to a compound of Formula (I), wherein Ar$^1$ and Ar$^2$ are phenyl optionally substituted with R$^g$, R$^h$ or R$^i$ where R$^g$ is alkyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, or acylamino and R$^h$ and R$^i$ are independently selected from alkyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, acylamino, aryl, or cycloalkyl where the aromatic or alicyclic ring in R$^g$, R$^h$ and R$^i$ is optionally substituted with R$^j$, R$^k$ or R$^l$ which are independently selected from alkyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, or acylamino (H) In another embodiment, this invention is directed to a compound of Formula (I), wherein Ar$^1$ and Ar$^2$ are phenyl optionally substituted with R$^g$, R$^h$ or R$^i$ where R$^g$ is alkyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, or acylamino and R$^h$ and R$^i$ are independently selected from alkyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, acylamino, aryl, heteroaryl, cycloalkyl, or heterocyclyl where the aromatic or alicyclic ring in R$^g$, R$^h$ and R$^i$ is optionally substituted with R$^j$, R$^k$ or R$^l$ which are independently selected from alkyl, halo, haloalkyl, haloalkoxy, alkylthio, cyano, alkoxy, amino, monosubstituted amino, disubstituted amino, sulfonyl, acyl, hydroxyalkyl, alkoxyalkyl, aminoalkyl, hydroxyalkoxy, alkoxyalkoxy, aminoalkoxy, aminosulfonyl, aminocarbonyl, or acylamino provided that R$^h$ and R$^i$ are not substituted or unsubstituted tetrazole.

(I) In another embodiment, this invention is directed to a compound of Formula (I), wherein Ar$^1$ is phenyl and Ar$^2$ is heteroaryl or heterocyclyl optionally substituted with R$^g$, R$^h$ or R$^i$ where R$^g$ is alkyl, halo, haloalkyl, haloalkoxy, alkylthio, cyano, alkoxy, amino, monosubstituted amino, disubstituted amino, sulfonyl, acyl, hydroxyalkyl, alkoxyalkyl, aminoalkyl, hydroxyalkoxy, alkoxyalkoxy, aminoalkoxy, aminosulfonyl, aminocarbonyl, or acylamino and R$^h$ and R$^i$ are independently selected from alkyl, halo, haloalkyl, haloalkoxy, alkylthio, cyano, alkoxy, amino, monosubstituted amino, disubstituted amino, sulfonyl, acyl, hydroxyalkyl, alkoxyalkyl, aminoalkyl, hydroxyalkoxy, alkoxyalkoxy, aminoalkoxy, aminosulfonyl, aminocarbonyl, acylamino, aryl, heteroaryl, cycloalkyl, or heterocyclyl where the aromatic or alicyclic ring in R$^g$, R$^h$ and R$^i$ is optionally substituted with R$^j$, R$^k$ or R$^l$ which are independently selected from alkyl, halo, haloalkyl, haloalkoxy, alkylthio, cyano, alkoxy, amino, monosubstituted amino, disubstituted amino, sulfonyl, acyl, hydroxyalkyl, alkoxyalkyl, aminoalkyl, hydroxyalkoxy, alkoxyalkoxy, aminoalkoxy, aminosulfonyl, aminocarbonyl, or acylamino provided that neither of R$^h$ and R$^i$ is substituted or unsubstituted tetrazole.

(J) In another embodiment, this invention is directed to a compound of Formula (I), Ar$^1$ and Ar$^2$ are independently aryl, heteroaryl, cycloalkyl, or heterocyclyl where each of the aforementioned ring is optionally substituted with R$^g$, R$^h$ or R$^i$ where R$^g$ is alkyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, or acylamino and R$^h$ and R$^i$ are independently selected from alkyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, acylamino, aryl, heteroaryl, cycloalkyl, or heterocyclyl where the aromatic or alicyclic ring in R$^g$, R$^h$ and R$^i$ is optionally substituted with R$^j$, R$^k$ or R$^l$ which are independently selected from alkyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, or acylamino; provided that: (i) when Ar$^1$ is phenyl substituted with one or more hydroxy or alkoxy, then Ar$^2$ is not phenyl or a bicyclic heteroaryl which is attached via the phenyl portion of the bicyclic ring wherein the phenyl or bicyclic heteroaryl ring is substituted with substituted or unsubstituted tetrazolyl; (ii) when Ar$^1$ is phenyl substituted with one or more hydroxy or alkoxy, then Ar$^2$ is not phenyl substituted with heterocyclic or heteroaryl ring wherein the heterocyclic or heteroaryl ring is substituted with carboxy, alkoxycarbonyl, or substituted or unsubstituted tetrazole ring; (iii) when Ar$^1$ is a five membered heteroaryl ring substituted with alkyl, substituted or unsubstituted heteroaryl or heterocyclyl, then Ar$^2$ is not five or six membered substituted or unsubstituted heteroaryl or heterocyclyl ring wherein the heteroaryl or heterocyclyl ring contains at least one nitrogen ring atom; and (iv) when Ar$^1$ is substituted or unsubstituted phenyl and Ar$^2$ is pyrimidin-4(3H)-one substituted or unsubstituted at N-3 nitrogen with R$^h$ and is attached to the —CR$^3$— carbon via the C-2 ring carbon, then it is not fused to a five membered heteroaryl ring.

Within embodiments (G)-(J) above, other groups of compounds of Formula (I) are those wherein R$^1$, R$^2$, R$^3$, Ar$^1$ and Ar$^2$ are as defined in the groups and subgroups contained within (A) to (F), (a)-(d), and (i)-(ix) and combinations thereof (K) In another embodiment, this invention is directed to a compound of Formula (I):

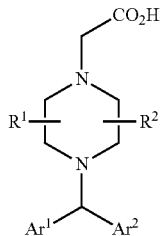

where:

R$^1$ and R$^2$ are independently hydrogen or alkyl; and

Ar$^1$ and Ar$^2$ are independently phenyl, each ring optionally substituted with R$^g$ or R$^h$ where R$^g$ and R$^h$ are independently alkyl, halo, haloalkyl, haloalkoxy, alkylthio, alkoxy, alkylcarbonyl, or alkoxycarbonyl. In one embodiment within this group, R$^1$ and R$^2$ are hydrogen. In another embodiment within this group, at least one of R$^1$ and R$^2$ is not hydrogen.

In one embodiment within this group, the compound of Formula (I) has one of the following structures:

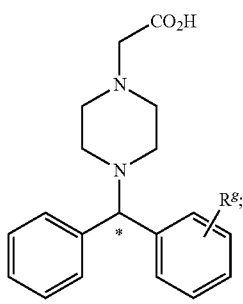 (a)

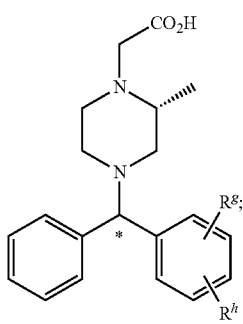 (b)

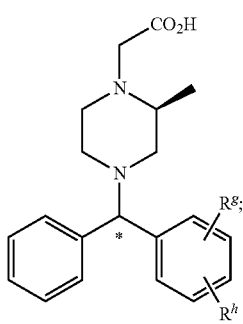 (c)

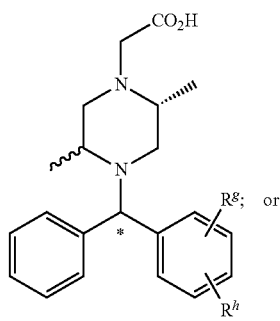 (d)

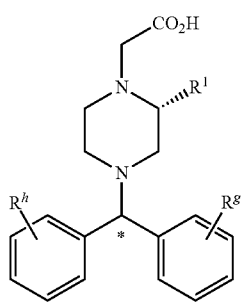 (e)

where R$^1$ is hydrogen or methyl and R$^g$ and R$^h$ are independently absent, alkyl, halo, haloalkyl, or haloalkoxy provided that in compound (a) R$^g$ is not absent. In another embodiment within this group, the compound of Formula (I) has one of the structures (a)-(e), where the R$^g$ group is attached to the 3-position of the phenyl ring and R$^g$ and R$^h$ are independently methyl, chloro, trifluoromethyl, or trifluoromethoxy. In another embodiment within this group, the compound of Formula (I) has one of the structures (a)-(e), where the R$^g$ group is attached to the 3-position of the phenyl ring and R$^g$ and R$^h$ are independently methyl, chloro, trifluoromethyl, or trifluoromethoxy and the stereochemistry at *C is (R). In yet another embodiment within this group, the compound of Formula (I) has one of the structures (a)-(e) where the R$^g$ group is attached to the 3-position of the phenyl ring. In another embodiment within this group, the compound of Formula (I) has one of the structures (a)-(e) where the R$^g$ group is attached to the 3-position of the phenyl ring and the stereochemistry at *C is (R).

(L) In another embodiment, this invention is directed to a compound of Formula (I):

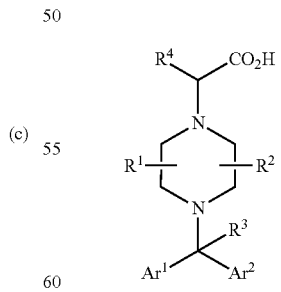

where:

R$^1$ and R$^2$ are independently hydrogen or alkyl;

R$^3$ is hydrogen, alkyl, fluoro, or fluoroalkyl; and

Ar$^1$ and Ar$^2$ are independently phenyl, each ring optionally substituted with R$^g$, R$^h$ or R$^i$ where R$^g$ is alkyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, or acylamino and $R^h$ and $R^i$ are independently selected from alkyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, acylamino, aryl, heteroaryl, cycloalkyl, or heterocyclyl where the aromatic or alicyclic ring in $R^g$, $R^h$ and $R^i$ is optionally substituted with $R^j$, $R^k$ or $R^l$ which are independently selected from alkyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, or acylamino provided that when $R^1$, $R^2$, $R^3$ and $R^4$ are hydrogen, $R^g$, $R^h$ or $R^i$ are not independently selected from alkyl, halo, haloalkyl, haloalkoxy, alkylthio, alkoxy, alkylcarbonyl, or alkoxycarbonyl. In one embodiment within this group, $R^3$ is hydrogen and $R^i$ is absent, $R^g$ is absent or halo, and $R^h$ is cyano, heteroaryl (except tetrazolyl) or phenyl each ring optionally substituted with $R^j$, $R^k$ or $R^l$. In another embodiment within this group, $R^3$ is hydrogen and $R^i$ is absent, $R^g$ is absent or halo, and $R^h$ is cyano, heteroaryl (except tetrazolyl) or phenyl each ring optionally substituted with alkyl.

In another embodiment within this group, the compound of Formula (I) has one of the following structures:

(a)

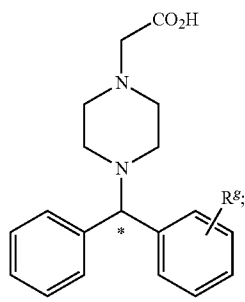

(b)

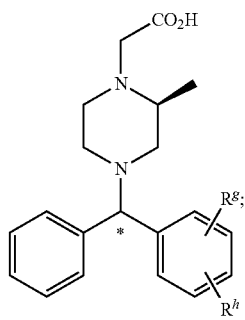

(c)

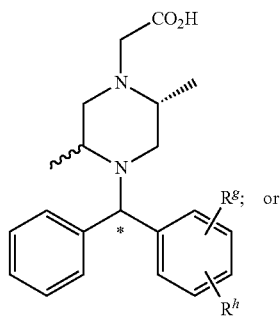

(d)

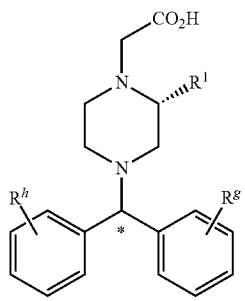

(e)

where $R^1$ is hydrogen or methyl, $R^g$ is cyano, heteroaryl or phenyl, each ring is optionally substituted with alkyl and $R^h$ is alkyl, halo, haloalkyl, or haloalkoxy.

In another embodiment within this group, the compound of Formula (I) has one of the structures (a)-(e), where the $R^g$ group is attached to the 3-position of the phenyl ring and $R^h$ is methyl, chloro, trifluoromethyl, or trifluoromethoxy.

In another embodiment within this group, the compound of Formula (I) has one of the structures (a)-(e), where the $R^g$ group is attached to the 3-position of the phenyl ring and the stereochemistry at *C is (R).

(M) In another embodiment, this invention is directed to a compound of Formula (I):
where:
n is 1;
$R^1$ and $R^2$ are independently selected from hydrogen, alkyl, haloalkyl, alkoxy, haloalkoxy, aryl, heteroaryl, cycloalkyl, or heterocyclyl wherein the aforementioned rings are optionally substituted with $R^a$, $R^b$, or $R^c$ independently selected from alkyl, halo, haloalkyl, alkoxy, haloalkoxy, hydroxy, cyano, monosubstituted amino, or disubstituted amino; or
$R^1$ and $R^2$, when attached to the same carbon atom, can combine to form cycloalkyl or monocyclic saturated heterocyclyl to give a spiro ring wherein the cycloalkyl or monocyclic saturated heterocyclyl can be optionally substituted with $R^d$, $R^e$, or $R^f$ independently selected from alkyl, alkoxy, fluoro, fluoroalkyl, fluoroalkoxy, hydroxy, monosubstituted amino, or disubstituted amino; or $R^1$ and $R^2$, when attached to carbon atoms 2 and 5 or 3 and 6 positions of the piperazine ring, can combine to form —$C_1$-$C_3$— alkylene chain wherein one of the carbon atoms in the alkylene chain is optionally replaced by a —NR—, —O—, —S(O)n1- (where R is hydrogen or alkyl and n1 is 0-2) and further wherein one or two hydrogen atoms in the alkylene chain can be optionally substituted with one or two alkyl; and $Ar^1$ and $Ar^2$ are independently aryl, heteroaryl, cycloalkyl, or heterocyclyl where each of the aforementioned ring is optionally substituted with $R^g$, $R^h$ or $R^i$ where $R^g$ is alkyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, or acylamino and $R^h$ and $R^i$ are independently selected from alkyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, acylamino, aryl, heteroaryl, cycloalkyl, or heterocyclyl where the aromatic or alicyclic ring in $R^g$, $R^h$ and $R^i$ is optionally substituted with $R^j$, $R^k$ or $R^l$ which are independently selected from alkyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, or acylamino provided that: the compound of Formula (I) is not 2-(4-benzhydrylpiperazin-1-yl)acetic acid or 2-(4-((4-chlorophenyl)(phenyl)methyl)piperazin-1-yl)acetic acid.

Within this embodiment, one group of compounds is that wherein $R^1$ and $R^2$ are independently selected from hydrogen, alkyl, haloalkyl, alkoxy, haloalkoxy, aryl, heteroaryl, cycloalkyl, or heterocyclyl wherein the aforementioned rings are optionally substituted with $R^a$, $R^b$, or $R^c$ independently selected from alkyl, halo, haloalkyl, alkoxy, haloalkoxy, hydroxy, cyano, monosubstituted amino, or disubstituted amino Within this embodiment, one group of compounds is that wherein when $Ar^1$ and $Ar^2$ are phenyl, the stereochemistry at the carbon atom at carrying the $Ar^1$ and $Ar^2$ group (i.e. —$CR^3Ar^1Ar^2$) is (R). Within this embodiment, another group of compounds is that wherein when $Ar^1$ and $Ar^2$ are independently phenyl or cycloalkyl provided that atleast one of $Ar^1$ and $Ar^2$ group is cycloalkyl, the stereochemistry at the carbon atom at carrying the $Ar^1$ and $Ar^2$ group (i.e. —$CR^3Ar^1Ar^2$) is (R). Within this embodiment, one group of compounds is that wherein when $Ar^1$ and $Ar^2$ are independently phenyl or heteroaryl, provided at least one of $Ar^1$ and $Ar^2$ group is phenyl, the stereochemistry at the carbon atom at carrying the $Ar^1$ and $Ar^2$ group (i.e. —$CR^3Ar^1Ar^2$) is (S).

Within this embodiment, yet another group of compounds is that wherein $R^1$ and $R^2$ are hydrogen.

Within this embodiment, yet another group of compounds is that wherein $R^1$ and $R^2$ are independently selected from hydrogen, alkyl, haloalkyl, alkoxy, or haloalkoxy provided that at least one of $R^1$ and $R^2$ is other than hydrogen.

Within this embodiment, yet another group of compounds is that wherein $R^1$ is hydrogen and $R^2$ is alkyl. Within this embodiment, one group of compounds is that wherein $R^2$ is methyl.

Within this embodiment, yet another group of compounds is that wherein $R^1$ and $R^2$ are attached to the same carbon atom and are combined to form cycloalkyl optionally substituted with $R^d$, $R^e$ or $R^f$ independently selected from alkyl, alkoxy, fluoro, fluoroalkyl, fluoroalkoxy, hydroxy, monosubstituted amino, or disubstituted amino Within this embodiment, yet another group of compounds is that wherein $R^1$ and $R^2$ are attached to the same carbon atom and are combined to form monocyclic saturated heterocyclyl which are optionally substituted with $R^d$, $R^e$ or $R^f$ independently selected from alkyl, alkoxy, fluoro, fluoroalkyl, fluoroalkoxy, hydroxy, monosubstituted amino, or disubstituted amino.

Within this embodiment, yet another group of compounds is that wherein $R^1$ and $R^2$ are attached to carbon atoms 2 and 5 or 3 and 6 positions of the piperazine ring, and are combined to form —$C_1$-$C_2$— alkylene chain wherein one or two hydrogen atoms in the alkylene chain can be optionally substituted with one or two alkyl.

Within this embodiment, yet another group of compounds is that wherein $R^3$ and $R^5$ are hydrogen, $R^1$, $R^2$, and $R^4$ are independently hydrogen or alkyl, and $Ar^1$ and $Ar^2$ are phenyl optionally substituted with $R^g$, $R^h$ or $R^i$ provided at least one of $R^1$, $R^2$, and $R^4$ is other than hydrogen.

Within this embodiment, yet another group of compounds is that wherein $R^3$ and $R^5$ are hydrogen, $R^1$, $R^2$, and $R^4$ are independently hydrogen or alkyl, $Ar^1$ is phenyl optionally substituted with $R^g$, $R^h$ or $R^i$ and $Ar^2$ is cycloalkyl provided at least one of $R^1$, $R^2$, and $R^4$ is other than hydrogen.

Within this embodiment, yet another group of compounds is that wherein $R^3$ and $R^5$ are hydrogen, $R^1$, $R^2$, and $R^4$ are independently hydrogen or alkyl, $Ar^1$ is phenyl and $Ar^2$ is heteroaryl, each ring optionally substituted with $R^g$, $R^h$ or $R^i$ provided at least one of $R^1$, $R^2$, and $R^4$ is other than hydrogen.

General Synthetic Scheme

Compounds of this invention can be made by the methods depicted in the reaction schemes shown below.

The starting materials and reagents used in preparing these compounds are either available from commercial suppliers such as Aldrich Chemical Co., (Milwaukee, Wis.), Bachem (Torrance, Calif.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), March's Advanced Organic Chemistry, (John Wiley and Sons, 4th Edition) and Larock's Comprehensive Organic Transformations (VCH Publishers Inc., 1989). These schemes are merely illustrative of some methods by which the compounds of this invention can be synthesized, and various modifications to these schemes can be made and will be suggested to one skilled in the art having referred to this disclosure. The starting materials and the intermediates, and the final products of the reaction may be isolated and purified if desired using conventional techniques, including but not limited to filtration, distillation, crystallization, chromatography and the like. Such materials may be characterized using conventional means, including physical constants and spectral data.

Unless specified to the contrary, the reactions described herein take place at atmospheric pressure over a temperature range from about −78° C. to about 150° C., more preferably from about 0° C. to about 125° C. and most preferably at about room (or ambient) temperature, e.g., about 20° C.

Compounds of Formula (I) where $Ar^1$, $Ar^2$, $R^1$, $R^2$, $R^3$, $R^4$ and $R^5$ are as defined in the Summary of the Invention can be prepared as illustrated and described in Scheme A below.

Scheme A

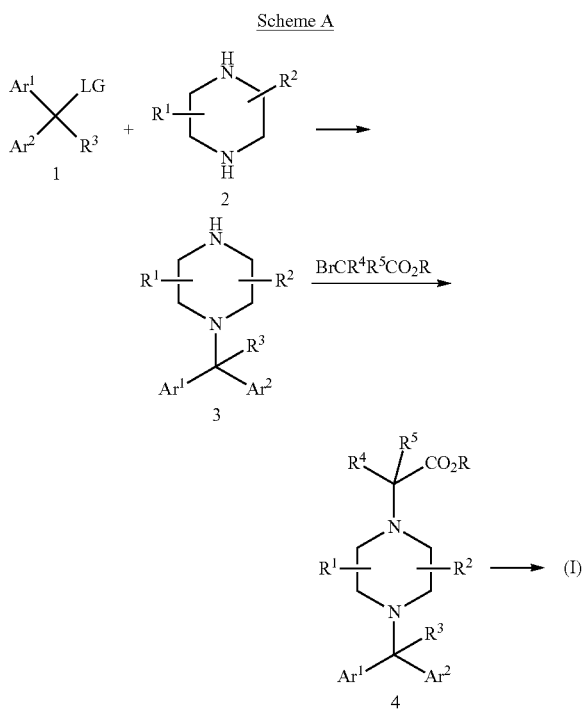

Treatment of a compound of formula 1 where LG is a suitable leaving group such as halo, tosylate, mesylate, triflate, and the like, and $Ar^1$, $Ar^2$, and $R^3$ are as defined in the Summary of the Invention with a piperazine of formula 2 where $R^1$ and $R^2$ are as defined in the Summary of the Invention, provides a compound of formula 3. The reaction is carried out in a suitable organic solvent such as acetonitrile, toluene, and the like (with or without a base such as trethylamine or disiopropylethylamine) and takes place upon heating at a suitable temperature between 70 to 150° C.

Compounds of formula 1 are either commercially available or can be readily prepared by methods well known in the art. For example, compounds of formula 1 where LG is halo can be prepared by reduction of a ketone compound of formula $Ar^1COAr^2$ with a suitable reducing agent such as sodium borohydride, and the like, in a suitable organic alcohol solvent such as methanol, ethanol, and the like to provide the corresponding alcohol of formula $Ar^1C(OH)Ar^2$ which upon treatment with a halogenating agent such as thionyl chloride, oxalyl chloride, triphenylphosphine/carbon tetrabromide, and the like provides the compound of formula 1 where LG is halo. Alternatively, $Ar^1C(OH)Ar^2$ can be treated with mesyl chloride, tosyl chloride, triflic anhydride under conditions well known in the art to provide a compound of formula 1 where LG is mesylate, tosylate, or triflate, respectively. Compounds of formula $Ar^1COAr^2$ are commercially available or they can be prepared by methods well known in the art. For example, acylating $Ar^1$ where $Ar^1$ is an aryl or heteroaryl ring with an $Ar^2COCl$ under Fridel-Crafts acylating reaction conditions.

Compounds of formula $Ar^1C(OH)Ar^2$ are either commercially available or they can also be prepared by treating an aldehyde of formula $Ar^1CHO$ with a Grignard reagent of formula $Ar^2MgX$ where X is halo under conditions well known in the art. Compounds of formula $Ar^1COAr^2$ and $Ar^1C$ (OH)$Ar^2$ such as (2-bromophenyl)(phenyl)methanone, 4-bromobenzophenone, 2-fluorobenzophenone, 2,4-difluorobenzophenone, (4-fluorophenyl)-(phenyl)methanone, 2-(trifluoromethyl)benzophenone, 3-(trifluoromethyl)-benzophenone, 4-(trifluoromethyl)-benzophenone, 3,4-dichlorobenzophenone, 4-chloro-benzophenone, 2-hydroxybenzophenone, 2,4-dihydroxybenzophenone, 3-hydroxybenzophenone, 5-chloro-2-hydroxy-4-methylbenzophenone, 4-hydroxybenzophenone, 2-hydroxy-5-methylbenzophenone, 3-benzoylbenzoic acid, 4-benzoylbenzoic acid, 4-benzoylbiphenyl, 4-morpholino-benzophenone, 4-amino-3-nitrobenzophenone, 3-nitro-benzophenone, 2-chloro-5-nitro-benzophenone, 4-nitro-benzophenone, 2-amino-5-nitro-benzophenone, 2-amino-benzophenone, 3,4-diamino-benzophenone, 2-amino-5-chloro-benzophenone, 4-aminobenzophenone, 4-(dimethylamino)-benzophenone, 2-hydroxy-4-methoxy-benzophenone, 4-methoxybenzophenone, 2-methylbenzophenone, 3-methylbenzophenone, (2,4-dimethylphenyl)(phenyl)methanone, 4-methylbenzophenone, 3-chloro-benzophenone, 3,4-difluorobenzophenone, 4-cyanobenzophenone, (3-aminophenyl)-(phenyl)methanone, 3,4-dihydro-2H-1,5-benzodioxepin-7-yl(phenyl)methanone, 3,4-dihydroxybenzophenone, 4-fluorobenzophenone, 2-benzoylbenzoic acid, 2-benzoylnaphthalene, 4-chloro-3-nitrobenzophenone, 3,4-dimethylbenzophenone, 2,5-difluoro-benzophenone, 1,4-dibenzoylbenzene, 4-ethylbenzophenone, 3,5-bis(trifluoromethyl)-benzophenone, 3-amino-benzophenone, 2-methoxybenzophenone, 1-naphthyl phenyl ketone, 2,3-difluoro-benzophenone, 3,5-difluorobenzophenone, 2-fluoro-5-(trifluoromethyl)benzophenone, 4-fluoro-3-(trifluoromethyl)benzophenone, 4-benzoyl-4'-bromobiphenyl, 6-benzoyl-2-naphthol, 2-amino-4-methylbenzophenone, 5-chloro-2-(methylamino)benzophenone, 2,5-dimethyl-benzophenone, methyl 2-benzoylbenzoate, 4-benzyloxybenzophenone, 5-chloro-2-hydroxybenzophenone, 2-(3-benzoylphenyl)propionitrile, 2-fluoro-3-(trifluoromethyl)-benzophenone, 4-(diethylamino)-benzophenone, 3-bromobenzophenone, 2-cyano-benzophenone, 4-ethoxy-2-hydroxybenzophenone, 2-chlorobenzophenone, (4-chlorophenyl)-(phenyl)methanol, (3-chlorophenyl)(phenyl)methanol, (4-bromophenyl)(phenyl)methanol, (3-trifluoromethyl-phenyl)(phenyl)methanol, (4-trifluoromethylphenyl)(phenyl)methanol, 4,4'-difluoro-benzhydrol, 4,4'-dichlorobenzhydrol, 2-methylbenzhydrol, 4-chlorobenzhydrol, 4-methylbenzhydrol, 4,4'-bis(dimethylamino)benzhydrol, 4,4'-dimethoxy-benzhydrol, 4,4'-dimethoxybenzhydrol, 2-(trifluoromethyl)benzhydrol, 3-(trifluoromethyl)-benzhydrol, 4-methoxybenzhydrol, 4-(trifluoromethyl) benzhydrol, 4,4'-dimethylbenzhydrol, and di[3,5-di(trifluoromethyl)phenyl]-methanol, bis(4-diethylaminophenyl)-methanol are commercially available from Lancaster Synthesis Ltd.; Fluka Chemie GmbH; Aldrich Chemical Company, Inc.; Alfa Aesar, A Johnson Matthey Company; Acros Organics USA; Maybridge; or VWR International.

Treatment of compound 3 with bromoacetate where R is alkyl, preferably methyl, ethyl, tert-butyl, and the like provides a compound of formula 4. The reaction is carried out in the presence of a base such as triethylamine, DIEA, and the like and in a suitable organic solvent such as acetonitrile, tetrahydrofuran, DMF, methylene chloride, and the like. Acidic or basic hydrolysis of the ester group in 4 then provides the compound of Formula (I).

Compounds of formula 4 can be further modified prior to converting it to a compound of Formula (I). For example, a compound of formula 4 where $Ar^1$ or $Ar^2$ is substituted with a halo group, can be reacted with alkynyl, aryl, or heteroarylboronic acids under Suzuki coupling reaction conditions to provide a corresponding compound of formula 4 where Ar¹ or Ar² is substituted with alkynyl, aryl, or heteroaryl ring respectively. The reaction is usually carried out in the presence of common palladium catalysts such as Pd(PPh$_3$)$_4$, Pd(PPh$_3$)$_2$Cl$_2$, Pd$_2$dba$_3$, Pd(dppf)Cl$_2$.CH$_2$Cl$_2$ and the like, and a weak base such as Na$_2$CO$_3$ and the like, in a mixture of solvents of water and a suitable organic solvent such as acetonitrile, p-dioxane, DMF, THF and the like. The reaction is usually heated up to 70-130° C. temperature range (oil bath or microwave irradiation). Acidic hydrolysis of the ester group in 4 then provides the compound of Formula (I).

Alternatively, the above transformation can be carried out under Stille coupling reaction conditions. Under Stille reaction conditions, the compound 4 where Ar¹ or Ar² is substituted with a halo group is treated with alkynyl, aryl, heteroaryltributyltin(or trimethyltin) derivatives to provide a compound of formula 4 where Ar¹ or Ar² is substituted with alkynyl, aryl, or heteroaryl ring respectively. The reaction is usually carried out in the presence of common palladium catalysts such as Pd(PPh$_3$)$_4$, Pd(PPh$_3$)$_2$Cl$_2$, Pd$_2$dba$_3$, Pd(dppf)Cl$_2$.CH$_2$Cl$_2$ and the like, and with or without additional ligands such as tBu$_3$P, Ph$_3$P, Ph$_3$As, and the like, in a suitable organic solvent such as toluene, acetonitrile, p-dioxane, DMF, THF and the like. The reaction temperature ranges from 20 to 150° C. (rt, oil bath or microwave irradiation). Acidic hydrolysis of the ester group in 4 then provides the compound of Formula (I). Alternatively, the above transformation can be carried out under Negishi or Sonogashira (where Ar¹ or Ar² is substituted with terminal alkyne) coupling reaction conditions.

Compounds of Formula (I) can be converted to other compounds of Formula (I). For example, compounds of Formula (I) where Ar¹ or Ar² is substituted with mono substituted or disubstituted amino as defined in the Summary of the Invention can be prepared from a corresponding compound of Formula (I) where Ar¹ or Ar² is substituted with nitro group by first reducing the nitro group to an amino group and then alkylating, arylating, sulfonylating or acylating the amino group under conditions well known in the art. The mono substituted amino can be converted to the disubstituted amino, if desired, by alkylating, arylating, sulfonylating, or acylating the monosubstituted amino. The reaction is typically carried out in the presence of a base such as potassium tert-butoxide, and the like, and a catalyst such as 18-crown-6 in a suitable solvent such as tetrahydrofuran, and the like. Compounds of Formula (I) where Ar¹ or Ar² is substituted with alkoxy, haloalkoxy, hydroxyalkoxy, or aminoalkoxy can be prepared by treating a corresponding compound of Formula (I) where Ar¹ or Ar² is substituted with hydroxy with alkyl halide, alkoxy halide, aminoalkyl halide or haloalkyl in the presence of a base.

It will be recognized by a person skilled in the art that the above transformations could also be carried out at earlier stages in the synthetic process based on feasibility of the transformations.

Alternatively, compounds of Formula (I) where Ar¹, Ar², R¹, R², R³, R⁴ and R⁵ are as defined in the Summary of the Invention can be prepared as illustrated and described in Scheme B below.

Scheme B

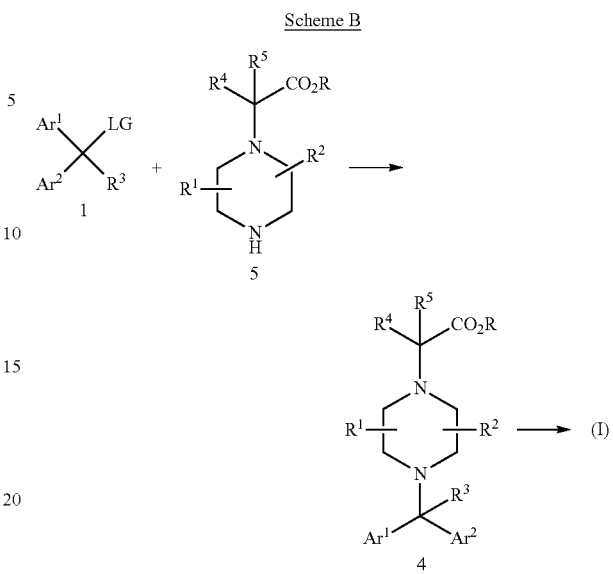

Alternatively, compounds of Formula (I) where Ar¹, Ar², R¹, R² and R³ are as defined in the Summary of the Invention can be prepared by reacting a compound of formula 1 with a compound of formula 5 provides a compound of formula 4 which is then converted to a compound of Formula (I) as described above. The reaction is carried out in the presence of a base such as triethylamine, diisopropylethylamine, and the like in a suitable organic solvent. Compounds of formula 5 can be prepared from commercially available piperazines as described above.

Utility

The NMDA receptor is central to a wide range of CNS processes, and plays a role in a variety of disease states in humans or other species. The action of GlyT1 transporters affects the local concentration of glycine around NMDA receptors. Selective GlyT1 inhibitors slow the removal of glycine from the synapse, causing the level of synaptic glycine to rise. This in turn increases the occupancy of the glycine binding site on the NMDA receptor, which increases activation of the NMDA receptor following glutamate release from the presynaptic terminal Because a certain amount of glycine is needed for the efficient functioning of NMDA receptors, any change to that local concentration can affect NMDA-mediated neurotransmission. Changes in NMDA-mediated neurotransmission have been implicated in certain neuropsychiatric disorders such as dementia, depression and psychoses, for example schizophrenia, and learning and memory disorders, for example attention deficit disorders and autism.

Accordingly, the compounds of the present invention have utility in treating a variety of neurological and psychiatric disorders associated with glutamatergic neurotransmission dysfunction, including one or more of the following conditions or diseases: schizophrenia or psychosis including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced or drug-induced (phencyclidine, ketamine and other dissociative anaesthetics, amphetamine and other psychostimulants and cocaine) psychosispsychotic disorder, psychosis associated with affective disorders, brief reactive psychosis, schizoaffective psychosis, "schizophrenia-spectrum" disorders such as schizoid or schizotypal personality disorders, or illness associated with psychosis (such as major depression, manic depressive (bipolar) disorder, Alzheimer's disease and post-traumatic stress syndrome), including both the positive and the negative symptoms of schizophrenia and other psychoses; cognitive disorders including dementia (associated with Alzheimer's disease, ischemia, multi-infarct dementia, trauma, vascular problems or stroke, Parkinson's disease, Huntington's disease, Pick's disease, Creutzfeldt-Jacob disease, perinatal hypoxia, other general medical conditions or substance abuse); delirium, amnestic disorders or age related cognitive decline; anxiety disorders including acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition; substance-related disorders and addictive behaviors (including substance-induced delirium, persisting dementia, persisting amnestic disorder, psychotic disorder or anxiety disorder; tolerance, dependence or withdrawal from substances including alcohol, amphetamines, cannabis, cocaine, hallucinogens, inhalants, nicotine, opioids, phencyclidine, sedatives, hypnotics or anxiolytics); bipolar disorders, mood disorders including depressive disorders; depression including unipolar depression, seasonal depression and post-partum depression, premenstrual syndrome (PMS) and premenstrual dysphoric, disorder (PDD), mood disorders due to a general medical condition, and substance-induced mood disorder; learning disorders, pervasive developmental disorder including autistic disorder, attention disorders including attention-deficit hyperactivity disorder (ADHD) and conduct disorder; NMDA receptor-related disorders such as autism, depression, benign forgetfulness, childhood learning disorders and closed head injury; movement disorders, including akinesias and akinetic-rigid syndromes (including Parkinson's disease, drug-induced parkinsonism, postencephalitic parkinsonism, progressive I supranuclear palsy, multiple system atrophy, corticobasal degeneration, parkinsonism-ALS dementia complex and basal ganglia calcification), medication-induced parkinsonism (such as neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Gilles de la Tourette's syndrome, epilepsy, muscular spasms and disorders associated with muscular spasticity or weakness including tremors; dyskinesias [including tremor (such as rest tremor, postural tremor and; intention tremor), chorea (such as Sydenham's chorea, Huntington's disease, benign hereditary chorea, neuroacanthocytosis, symptomatic chorea, drug-induced chorea and hemiballism), myoclonus (including generalized myoclonus and focal myoclonus), tics (including simple tics, complex tics and symptomatic tic s), and dystonia (including generalised dystonia such as iodiopathic dystonia, drug-induced dystonia, symptomatic dystonia and paroxymal dystonia, and focal dystonia such as blepharospasm, oromandibular dystonia, spasmodic dysphonia, spasmodic torticollis, axial dystonia, dystonic writer's cramp and hemiplegic dystonia); urinary incontinence; neuronal damage including ocular damage, retinopathy or macular degeneration of the eye, tinnitus, hearing impairment and loss, and brain edema; emesis; and sleep disorders including insomnia and narcolepsy.

Of the disorders above, the treatment of schizophrenia, bipolar disorder, depression including unipolar depression, seasonal depression and post-partum depression, premenstrual syndrome (PMS) and premenstrual dysphoric disorder (PDD), learning disorders, pervasive developmental disorder including autistic disorder, attention disorders including Attention-Deficit/Hyperactivity Disorder, autistic disorders including Tourette's disorder, anxiety disorders including phobia and post traumatic stress disorder, cognitive disorders associated with dementia, AIDS dementia, Alzheimer's, Parkinson's, Huntington's disease, spasticity, myoclonus, muscle spasm, tinnitus and hearing impairment and loss are of particular importance.

In a specific embodiment, the present invention provides a method for treating cognitive disorders, comprising: administering to a patient in need thereof an effective amount of a compound of the present invention. Particular cognitive disorders are dementia, delirium, amnestic disorders and age related cognitive decline. At present, the text revision of the fourth edition of the Diagnostic and Statistical Manual of Mental Disorders (DSM-IV-TR) (2000, American Psychiatric Association, Washington D.C.) provides a diagnostic tool that includes cognitive disorders including dementia, delirium, amnestic disorders and age-related cognitive decline. As used herein, the term "cognitive disorders" includes treatment of those mental disorders as described in DSM-IV-TR. The skilled artisan will recognize that there are alternative nomenclatures, nosologies and classification systems for mental disorders, and that these systems evolve with medical and scientific progress. Thus the term "cognitive disorders" is intended to include like disorders that are described in other diagnostic sources.

In another specific embodiment, the present invention provides a method for treating anxiety disorders, comprising: administering to a patient in need thereof an effective amount of a compound of the present invention. Particular anxiety disorders are generalized anxiety disorder, obsessive-compulsive disorder and panic attack. At present, the text revision of the fourth edition of the Diagnostic and Statistical Manual of Mental Disorders (DSM-IV-TR) (2000, American Psychiatric Association, Washington D.C.) provides a diagnostic tool that includes anxiety disorders are generalized anxiety disorder, obsessive-compulsive disorder and panic attack. As used herein, the term "anxiety disorders" includes treatment of those mental disorders as described in DSM-IV-TR. The skilled artisan will recognize that there are alternative nomenclatures, nosologies and classification systems for mental disorders, and that these systems evolve with medical and scientific progress. Thus the term 'anxiety disorders" is intended to include like disorders that are described in other diagnostic sources.

In another specific embodiment, the present invention provides a method for treating schizophrenia or psychosis comprising: administering to a patient in need thereof an effective amount of a compound of the present invention. Particular schizophrenia or psychosis pathologies are paranoid, disorganized, catatonic or undifferentiated schizophrenia and substance-induced psychotic disorder. At present, the text revision of the fourth edition of the Diagnostic and Statistical Manual of Mental Disorders (DSM-IV-TR) (2000, American Psychiatric Association, Washington D.C.) provides a diagnostic tool that includes paranoid, disorganized, catatonic or undifferentiated schizophrenia and substance-induced psychotic disorder. As used herein, the term "schizophrenia or psychosis" includes treatment of those mental disorders as described in DSM-IV-TR. The skilled artisan will recognize that there are alternative nomenclatures, nosologies and classification systems for mental disorders, and that these systems evolve with medical and scientific progress. Thus the term "schizophrenia or psychosis" is intended to include like disorders that are described in other diagnostic sources.

In another specific embodiment, the present invention provides a method for treating substance-related disorders and addictive behaviors, comprising: administering to a patient in need thereof an effective amount of a compound of the present invention. Particular substance-related disorders and addictive behaviors are persisting dementia, persisting amnestic disorder, psychotic disorder or anxiety disorder induced by substance abuse, and tolerance of, dependence on or withdrawal, from substances of abuse. At present, the text revision of the fourth edition of the Diagnostic; Statistical Manual of Mental Disorders (DSM-IV-TR) (2000, American Psychiatric Association, Washington D.C.) provides a diagnostic tool that includes persisting dementia, persisting amnestic disorder, psychotic disorder or anxiety disorder induced by substance abuse; and tolerance of, dependence on or withdrawal from substances of abuse. As used herein, the term "substance-related disorders and addictive behaviors" includes treatment of those mental disorders as described in DSM-IV TR. The skilled artisan will recognize that there are alternative nomenclatures, nosologies and classification systems for mental disorders, and that these systems evolve with medical arid scientific progress. Thus the term "substance-related disorders and addictive behaviors" is intended to include like disorders that are described in other diagnostic sources.

Testing

The GlyT1 inhibitory activity of the compounds of the present invention can be tested using the in vitro and in vivo assays described in working Example 1 below.

Administration and Pharmaceutical Composition

In general, the compounds of this invention will be administered in a therapeutically effective amount by any of the accepted modes of administration for agents that serve similar utilities. Therapeutically effective amounts of compounds of Formula (I) may range from about 0.01 to about 500 mg per kg patient body weight per day, which can be administered in single or multiple doses. Preferably, the dosage level will be about 0.1 to about 250 mg/kg per day; more preferably about 0.5 to about 100 mg/kg per day. A suitable dosage level may be about 0.01 to about 250 mg/kg per day, about 0.05 to about 100 mg/kg per day, or about 0.1 to about 50 mg/kg per day. Within this range the dosage can be about 0.05 to about 0.5, about 0.5 to about 5 or about 5 to about 50 mg/kg per day. For oral administration, the compositions are preferably provided in the form of tablets containing about 1.0 to about 1000 milligrams of the active ingredient, particularly about 1.0, 5.0, 10, 15, 20, 25, 50, 75, 100, 150, 200, 250, 300, 400, 500, 600, 750, 800, 900, and 1000 milligrams of the active ingredient. The actual amount of the compound of this invention, i.e., the active ingredient, will depend upon numerous factors such as the severity of the disease to be treated, the age and relative health of the subject, the potency of the compound utilized, the route and form of administration, and other factors.

In general, compounds of this invention will be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen, which can be adjusted according to the degree of affliction. Compositions can take the form of tablets, pills, capsules, semisolids, powders, sustained release formulations, solutions, suspensions, elixirs, aerosols, or any other appropriate compositions.

The choice of formulation depends on various factors such as the mode of drug administration (e.g., for oral administration, formulations in the form of tablets, pills or capsules are preferred) and the bioavailability of the drug substance. Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of in general, a compound of formula (I) in combination with at least one pharmaceutically acceptable excipient. Acceptable excipients are non-toxic, aid administration, and do not adversely affect the therapeutic benefit of the compound of formula (I). Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of this invention in aerosol form. Inert gases suitable for this purpose are nitrogen, carbon dioxide, etc.

Other suitable pharmaceutical excipients and their formulations are described in Remington's Pharmaceutical Sciences, edited by E. W. Martin (Mack Publishing Company, 18th ed., 1990).

The level of the compound in a formulation can vary within the full range employed by those skilled in the art. Typically, the formulation will contain, on a weight percent (wt %) basis, from about 0.01-99.99 wt % of a compound of formula (I) based on the total formulation, with the balance being one or more suitable pharmaceutical excipients. Preferably, the compound is present at a level of about 1-80 wt %.

The compounds of the present invention may be used in combination with one or more other drugs in the treatment of diseases or conditions for which compounds of the present invention or the other drugs may have utility, where the combination of the drugs together are safer or more effective than either drug alone. Such other drug(s) may be administered, by a route and in an amount commonly used therefor, contemporaneously or sequentially with a compound of the present invention. When a compound of the present invention is used contemporaneously with one or more other drugs, a pharmaceutical composition in unit dosage form containing such other drugs and the compound of the present invention is preferred. However, the combination therapy may also include therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly.

Accordingly, the pharmaceutical compositions of the present invention also include those that contain one or more other active ingredients, in addition to a compound of the present invention.

The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention also include those that also contain one or more other active ingredients, in addition to a compound of the present invention. The weight ratio of the compound of the present invention to the second active ingredient may be varied and will depend upon the effective dose of each ingredient. Generally, an effective dose of each will be used.

In one embodiment, the compound of the present invention may be administered in combination with anti-Alzheimer's agents, beta-secretase inhibitors, gamma-secretase inhibitors, HMG-CoA reductase inhibitors, NSAID's including ibuprofen, vitamin E, and anti-amyloid antibodies. In another embodiment, the compound of the present invention may be administered in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, PDE10 antagonists, and the like, such as: adinazolam, allobarbital, alonimid, alprazolam, amisulpride, amitriptyline, amobarbital, amoxapine, aripiprazole, bentazepam, benzoctamine, brotizolam, bupropion, busprione, butabarbital, butalbital, capuride, carbocloral, chloral betaine, chloral hydrate, clomipramine, clonazepam, cloperidone, clorazepate, chlordiazepoxide, clorethate, chlorpromazine, clozapine, cyprazepam, desipramine, dexclamol, diazepam, dichloralphenazone, divalproex, diphenhydramine, doxepin, estazolam, ethchlorvynol, etomidate, fenobam, flunitrazepam, flupentixol, fluphenazine, flurazepam, fluvoxamine, fluoxetine, fosazepam, glutethimide, halazepam, haloperidol, hydroxyzine, imipramine, lithium, lorazopam, lormetazepam, maprotiline, mecloqualone, melatonin, mephobarbital, meprobamate, methaqualone, midaflur, midazolam, nefazodone, nisobamate, nitrazopam, nortriptyline, olanzapine, oxazepam, paraldehyde, paroxetine, pentobarbital, perlapine, perphenazine, phenelzine, phenobarbital, prazepam, promethazine, propofol, protriptyline, quazepam, quetiapine, reclazepam, risperidone, roletamide, secobarbital, sertraline, suproclone, temazopam, thioridazine, thiothixene, tracazolate, kanylcypromaine, trazodone, triazolam, trepipam, tricetamide, triclofos, trifluoperazine, trimetozine, trimipramine, uldazepam, venlafaxine, zaleplon, ziprasidone, zolazepam, zolpidem, and salts thereof, and combinations thereof In another embodiment, the compound of the present invention may be administered in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexol) hydrochloride, COMT inhibitors such as entacapone, MOA-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and prarnipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate. Lisuride and pramipexol are commonly used in a non-salt form.

In another embodiment, the compound of the present invention may be administered in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the subject compound may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form. Thus, the compound of the present invention may be administered in combination with acetophenazine, alentemol, aripiprazole, amisulpride, benzhexol, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, quetiapine, risperidone, sulpiride, tetrabenazine, trihexyphenidyl, thioridazine, thiothixene, trifluoperazine or ziprasidone.

In another embodiment, the compound of the present invention may be administered in combination with an antidepressant or anti-anxiety agent, including norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, adrenoreceptor antagonists, neurokinin-1 receptor antagonists, atypical antidepressants, benzodiazopines, 5-HTA agonists or antagonists, especially 5-HTA partial agonists, and corticotropin releasing factor (CRF) antagonists. Specific agents include: amitriptyline, clomipramine, doxepin, imipramine and trimipramine; amoxapine, desipramine, maprotiline, nortriptyline and protriptyline; fluoxetine, fluvoxamine, paroxetine and sertraline; isocarboxazid, phenelzine, tranylcypromine and selegiline; moclobemide, venlafaxine; duloxetine; aprepitant; bupropion, lithium, nefazodone, trazodone and viloxazine; alprazolam, chlordiazepoxide, clonazepam, chlorazepate, diazopam, halazepam, lorazepam, oxazopam and prazepam; buspirone, flesinoxan, gepirone and ipsapirone, and pharmaceutically acceptable salts thereof

EXAMPLES

The following preparations of compounds of Formula (I) and intermediates (References) are given to enable those skilled in the art to more clearly understand and to practice the present invention. They should not be considered as limiting the scope of the invention, but merely as being illustrative and representative thereof

Synthetic Examples

Reference A

Synthesis of 1-(chloro(phenyl)methyl)-3-(trifluoromethyl)benzene

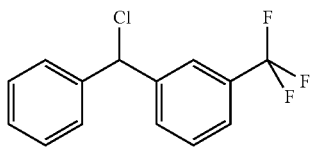 [SMILES: FC(F)(F)c1cccc(C(Cl)c2ccccc2)c1]

To a solution of 3-(trifluoromethyl)benzhydrol (5 mL, 20 mmol) in CH$_2$Cl$_2$ (10 mL) was added dropwise thionyl chloride (3 mL, 41 mmol) at rt. The reaction was stirred at 50° C. for 18 h, concentrated under vacuum, azeotroped with toluene and dried under vacuum to give the title compound (4.9 g, 89% yield) as oil, which was used in the next step without further purification. MS (ESI, pos. ion) m/z: 235.0 (M-HCl).

Using the methodology described above, 1-(chloro(phenyl)methyl)-4-(trifluoromethyl)-benzene was prepared.

Reference B

Synthesis of (3-bromophenyl)(phenyl)methanol

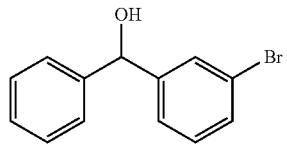 [SMILES: OC(c1ccccc1)c1cccc(Br)c1]

To a solution of 3-bromobenzophenone (1.00 g, 4 mmol) in MeOH (15 mL) was added sodium borohydride (0.3 mL, 8 mmol) portionwise at rt and the suspension was stirred at rt for 1-24 h. The reaction was diluted slowly with water and extracted with CH$_2$Cl$_2$. The organic layer was washed successively with water, brine, dried over Na$_2$SO$_4$, and concentrated to give the title compound as oil (0.8 g, 79%), which was used in the next reaction without further purification. MS (ESI, pos. ion) m/z: 247.1 (M-OH).

Using the methodology described above, (2-bromophenyl)(phenyl)methanol, (4-bromophenyl)(phenyl)methanol, and phenyl(3-(trifluoromethyl)phenyl)methanol were prepared.

Alternative Synthesis

To a solution of 3-bromobenzaldehyde (15.6 g, 84 mmol) in THF (60 mL) was added 3.0M phenylmagnesium bromide solution in diethyl ether (18 mL, 101 mmol) dropwise at −78° C. from a dropping funnel and the reaction was stirred at −78° C. or rt. After stirring for 4 h at −78° C. or rt, the reaction mixture was diluted with saturated NH$_4$Cl solution and extracted with CH$_2$Cl$_2$. The organic layers were combined, washed with saturated NaCl solution, then dried over Na$_2$SO$_4$, and concentrated. The crude product was purified by ISC

Reference C

Synthesis of 1-(phenyl(3-(trifluoromethyl)phenyl)methyl)piperazine

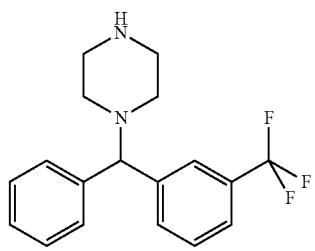 [SMILES: FC(F)(F)c1cccc(C(c2ccccc2)N2CCNCC2)c1]

To a solution of phenyl(3-(trifluoromethyl)phenyl)methanol (10.0 g, 39.6 mmol) in CH$_2$Cl$_2$ (20 mL) was added thionyl chloride (5.78 mL, 79.3 mmol) dropwise at rt. After the addition, the reaction was warmed to 40° C. for 18 h. The solvent was evaporated in vacuo and the residue was dried under vacuum pump for 1 h. The residue was dissolved in CH$_3$CN and added to a solution of piperazine (13.7 g, 159 mmol) in CH$_3$CN and heated to 100° C. for 12 h. The solvent was removed in vacuo, the residue dissolved in CH$_2$Cl$_2$ (150 mL) and washed with 1N NaOH (150 mL). The organic layer was dried with K$_2$CO$_3$ or Na$_2$SO$_4$, filtered, and concentrated. The crude product 1-(phenyl(3-(trifluoromethyl)phenyl)-methyl)piperazine (10.8 g, 85.0% yield) an oil was used without further purification or can be purified by ISCO flash chromatography using 0-15% 2N NH3 methanol solution in CH$_2$Cl$_2$. MS (ESI, pos. ion) m/z: 321.1 (M+1).

Using a method similar to the synthesis of 1-(phenyl(3-(trifluoromethyl)-phenyl)-methyl)-piperazine, 1-((2-bromophenyl)(phenyl)methyl)piperazine and 1-((3-bromophenyl)(phenyl)-methyl)piperazine were prepared.

Reference D

Synthesis of (3R)-3-methyl-1-(phenyl(3-(trifluoromethyl)phenyl)-methyl)piperazine

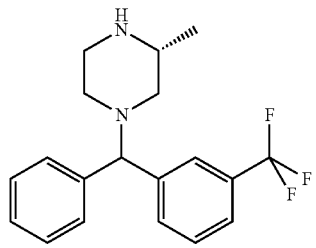 [SMILES: C[C@@H]1CN(C(c2ccccc2)c2cccc(C(F)(F)F)c2)CCN1]

To a solution of (R)-(−)-2-methylpiperazine (2.2 g, 22 mmol) in CH$_3$CN (20 mL) was added 1-(chloro(phenyl)methyl)-3-(trifluoromethyl)benzene (2.0 g, 7.4 mmol) and heated to 100° C. for 12 h and concentrated under vacuum. The residue was dissolved in CH$_2$Cl$_2$ (150 mL) and washed with 1N NaOH (150 mL). The organic layer was dried with K$_2$CO$_3$ or Na$_2$SO$_4$, filtered, and concentrated. The crude product was purified by ISCO using 0-20% 2N NH$_3$/MeOH solution in CH$_2$Cl$_2$ to give the title compound (2.00 g, 81% yield) as oil. MS (ESI, pos. ion) m/z: 335.1 (M+1).

Using a method similar to the synthesis of (3R)-3-methyl-1-(phenyl(3-(trifluoro-methyl)phenyl)methyl)piperazine, (3R)-1-((3-bromophenyl)(phenyl)methyl)-3-methyl-piperazine and 1-(phenyl(4-(trifluoromethyl)phenyl)methyl)piperazine were prepared.

Reference E

Synthesis of tert-butyl 2-(4-(phenyl(3-(trifluoromethyl)phenyl)-methyl)piperazin-1-yl)acetate

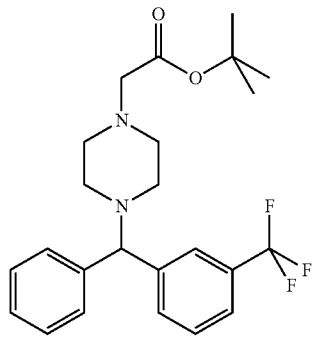 [SMILES: CC(C)(C)OC(=O)CN1CCN(C(c2ccccc2)c2cccc(C(F)(F)F)c2)CC1]

To a solution of 1-(phenyl(3-(trifluoromethyl)phenyl)methyl)piperazine (10.0 g, 31 mmol) in acetonitrile (60 mL) was added tert-butyl bromoacetate (6.1 mL, 31 mmol) dropwise from a syringe. The reaction mixture was stirred at rt for 5 min. and triethylamine (11 mL, 78 mmol) was added. Water was added after 18 h followed by CH$_2$Cl$_2$. The layers were separated, the aqueous layer was extracted with CH$_2$Cl$_2$ and the combined organic layers were washed with brine, dried over Na$_2$SO$_4$, and concentrated. The crude product was purified by ISCO using 0-80% EtOAc in hexanes to give the title compound (9.1 g, 67% yield) as brown oil that solidified on standing. MS (ESI, pos. ion) m/z: 435.2 (M+1).

Alternate Synthesis:

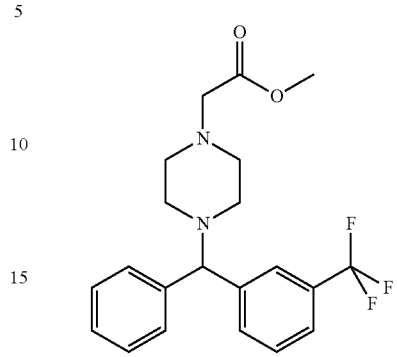

To a solution of 1-(phenyl(3-(trifluoromethyl)phenyl)methyl)piperazine (1.70 g, 5.3 mmol) in acetonitirle (20 mL) was added methyl 2-bromoacetate (0.49 mL, 5.3 mmol) dropwise at rt. The reaction was stirred for 30 min and triethylamine (2.2 mL, 16 mmol) added. After stirring for 18 hours at rt the reaction was diluted with water and extracted with CH$_2$Cl$_2$. The organic layers were combined and washed with saturated NaCl solution, then dried over Na$_2$SO$_4$, and concentrated. The crude product was purified by ISCO using 0-40% ethyl acetate or 0-2% ethyl acetate in CH$_2$Cl$_2$ to give the title compound (1.0 g, 48% yield). MS (ESI, pos. ion) m/z: 393.2 (M+1).

Using a method similar to the synthesis of tert-butyl 2-(4-(phenyl(3-(trifluoromethyl)-phenyl)methyl)piperazin-1-yl) acetate, the following compounds were prepared:

tert-butyl 2-(4-((3,5-dichlorophenyl)(phenyl)methyl)piperazin-1-yl)acetate;

tert-butyl 2-(4-((4-chlorophenyl)(phenyl)methyl)piperazin-1-yl)acetate;

tert-butyl 2-(4-((2-bromophenyl)(phenyl)methyl)piperazin-1-yl)acetate;

tert-butyl 2-((R)-2-methyl-4-(phenyl(3-(trifluoromethyl)phenyl)methyl)piperazin-1-yl)acetate;

tert-butyl 2-((R)-4-((3-bromophenyl)(phenyl)methyl)-2-methylpiperazin-1-yl)acetate;

tert-butyl 2-(4-(phenyl(4-(trifluoromethyl)phenyl)methyl)piperazin-1-yl)acetate; and tert-butyl 2-(4-benzhydrylpiperazin-1-yl)acetate.

REFERENCE F

Synthesis of tert-butyl 2-(4-((3-bromophenyl)(phenyl)methyl)piperazin-1-yl)acetate

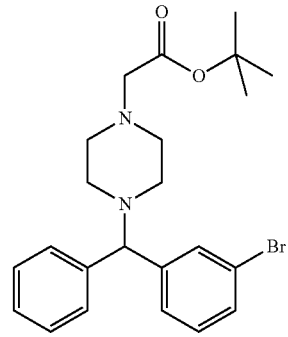

Method 1

To a solution of (3-bromophenyl)(phenyl)methanol (0.64 g, 2 mmol) in dichloroethane (5 mL) was added thionyl chloride (0.4 mL, 5 mmol) and the reaction was stirred for 18 h, concentrated and added to tert-butyl piperazin-1-yl-acetate dihydrochloride (0.7 g, 2 mmol) and DIEA (2 mL, 12 mmol) in aceonitrile (10 mL). After stirring for 18 hours at 100° C., the reaction was diluted with water and extracted with $CH_2Cl_2$. The organic layers were combined, washed with saturated NaCl solution, then dried over $Na_2SO_4$, and concentrated. The crude product was purified by ISCO using 0-50% EtOAc in haxanes to give the title product (0.3 g, 28% yield). MS (ESI, pos. ion) m/z: 447.2.2 (M+2).

Proceeding as described above, tert-butyl 2-(4-((4-bromophenyl)(phenyl)methyl)-piperazin-1-yl)acetate was prepared.

Method 2

Using the method described for tert-butyl 2-(4-(phenyl(3-(trifluoromethyl)-phenyl)-methyl)-piperazin-1-yl)acetate, the title compound was synthesized with 1-((3-bromophenyl)(phenyl)-methyl)piperazine (6.8 g, 21 mmol) and tert-butyl bromoacetate (3.3 mL, 21 mmol).

Reference G

Synthesis of (R) and (S)-methyl 2-(4-(phenyl(3-(trifluoromethyl)phenyl)-methyl)piperazin-1-yl)-acetate

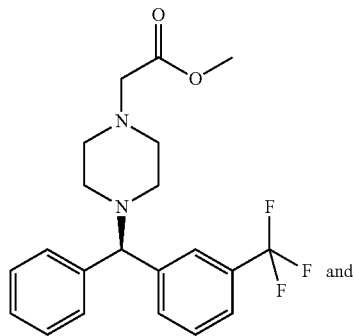

and

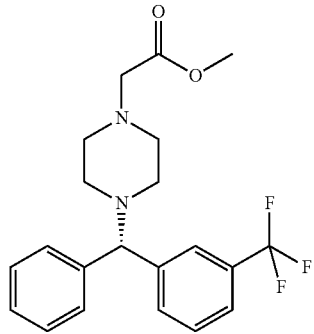 [SMILES: COC(=O)CN1CCN(C(c2ccccc2)c2cccc(C(F)(F)F)c2)CC1]

To a solution of 1-(phenyl(3-(trifluoromethyl)phenyl)methyl)piperazine (2.0 g, 6 mmol) in acetonitrile (20 mL) was added methyl bromoacetate (0.59 mL, 6 mmol) dropwise at rt. The reaction was stirred for 30 min. and triethylamine (3.6 mL, 26 mmol) was added. After stirring for 18 h at rt, the reaction mixture was diluted with water and extracted with $CH_2Cl_2$. The organic layers were combined, washed with saturated NaCl solution, then dried over $Na_2SO_4$, and concentrated. The crude product was purified by ISCO using 0-40% ethyl acetate or 0-2% ethyl acetate in $CH_2Cl_2$ to give a mixture of enantiomers (2.0 g, 80%). The enantiomers were separated by chiral chromatography as described below and two peaks were collected with ~100% ee.

Instrumentation and Conditions for Analytical SFC:

The Analytical SFC was a Berger SFC unit with an FCM 1200 flow control module, a dual pump control module and a TCM 2100 thermal column module, a column selection valve and a solvent control valve. The SFC was equipped with an Agilent 1100 photodiode array detector with a high pressure flow cell. The auto sampler unit was a HTC PAL (Leap Technologies). A Waters ZQ bench top single quadrupole mass spectrometer with atmospheric pressure chemical ionization (APCI) source was coupled to the analytical SFC system. The software used in the analyses was Berger MassWare v 4.01 and MassLynx v 4.0 SP 1. The analytical packed column used was Chiralcel OJ-H (Chrial Technologies, 4.6 mm×150 mm, 5 μm). Mobile phase consisted of 95% carbon dioxide and 5% methanol. Total flow rate was 4.0 ml/min, oven temperature was 40° C.

Sample Prep for Preparative SFC 600 mg of a mixture of (R) and (5)-methyl 2-(4-(phenyl(3-(trifluoromethyl)phenyl)-methyl)piperazin-1-yl)-acetate obtained above, was taken up in 5 ml of methanol and 5 ml of dimethoxyethyleneglycol(DME) and then added 40 ml of methanol, filtered through 0.45 um PTFE syringe filters before injection.

Instrumentation and Conditions for Prep SFC:

The preparative SFC was a Berger MultiGram II. The components were the Separator Control Module (SCM)-2500, Electronics Control Module (ECM)-2500, Carbon dioxide Solvent Delivery Module, Direct Expansion probe Chiller, UV Variable Wavelength Detector, and Cavro XL 3000 Modular Digital Pump (injector). Equipment was from Mettler-Toledo Autochem (Newark, Del.). The software in the purification was Berger SFC PronTo v1.5.305.15. The preparative packed column used were two Chiralcel OJH (Chiral Technologies, 21 mm×250 mm, 5 μm) linearly coupled together. Mobile phase consisted of liquid carbon dioxide (A) and methanol (B). The method was isocratic with a ratio of 92:8 of A: B. Total flow rate was 60 ml/min. Oven and column temperatures were about 40° C. The above sample was injected every 224 seconds during the isocratic run. The first peak 0.8 g is the (5) isomer and the second peak 0.9 g is the (R) isomer. MS (ESI, pos. ion) m/z: 393.1 (M+1).

Example 1

Synthesis of (S)-2-(4-benzhydryl-2-methylpiperazin-1-yl)acetic acid dihydrochloride

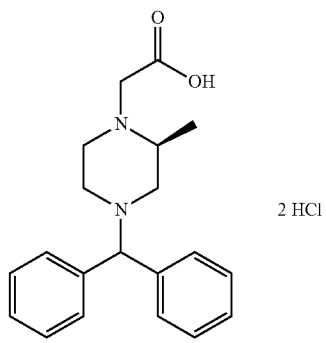 [SMILES: C[C@H]1CN(C(c2ccccc2)c2ccccc2)CCN1CC(=O)O ; "2 HCl"]

2 HCl

Step 1

A mixture of chlorodiphenylmethane (404 mg, 1.993 mmol) and (S)-(+)-2-methyl-piperazine (599 mg, 5980 μmol) in 2.5 mL of MeCN was heated at 140° C. under microwave irradiation for 30 min. The solvent was evaporated and the solid residue was submitted to column chromatography (SiO$_2$, EtOAc to EtOAc/2M NH$_3$ in MeOH=100:20) to give a mixture of two regioisomers (S)-1-benzhydryl-3-methylpiperazine and (S)-1-benzhydryl-2-methylpiperazine as a white solid. The mixture of the two products was directly used in the next step.

Step 2

To a solution of a mixture of (S)-1-benzhydryl-2-methylpiperazine and (S)-1-benzhydryl-3-methylpiperazine (490 mg, 1.839 mmol) in 25 mL of MeCN was added tert-butyl bromoacetate (356 μl, 2.207 mmol), followed by slow addition of triethylamine (384 μl, 2759 μmol). The reaction mixture was stirred at rt overnight. The solution was evaporated to dryness and the residual was submitted to flash chromatography (SiO$_2$, DCM to DCM/EtOAc=100:3 to 100:5 to 100:10) to give (S)-tert-butyl 2-(4-benzhydryl-3-methylpiperazin-1-yl)acetate as a colorless oil and (S)-tert-butyl 2-(4-benzhydryl-2-methylpiperazin-1-yl)acetate as a colorless oil.

Step 3

A solution of (S)-tert-butyl 2-(4-benzhydryl-2-methylpiperazin-1-yl)acetate (340 mg, 894 μmol) in 3 mL of 1,4-dioxane and 1 mL of concentrated HCl solution (37%) was stirred at rt overnight. The solvent was evaporated to dryness and the residue was crashed out of ether to give (S)-2-(4-benzhydryl-2-methylpiperazin-1-yl)acetic acid dihydrochloride as a white solid. MS (ESI, pos. ion) m/z: 325 (M+1).

The following compounds were prepared by proceeding as described in Example 1 above.

(S)-2-(4-benzhydryl-3-methylpiperazin-1-yl)acetic acid dihydrochloride; MS (ESI, pos. ion) m/z: 325 (M+1);

(R)-2-(4-benzhydryl-3-methylpiperazin-1-yl)acetic acid dihydrochloride; MS (ESI, pos. ion) m/z: 325 (M+1);

(R)-2-(4-benzhydryl-2-methylpiperazin-1-yl)acetic acid dihydrochloride; MS (ESI, pos. ion) m/z: 325 (M+1);

(S)-2-((R)-4-(bis(4-chlorophenyl)methyl)-3-methylpiperazin-1-yl)propanoic acid;

(R)-2-((R)-4-(bis(4-chlorophenyl)methyl)-2-methylpiperazin-1-yl)propanoic acid;

(S)-2-((R)-4-(bis(4-chlorophenyl)methyl)-2-methylpiperazin-1-yl)propanoic acid;

2-((2R,6S)-4-(bis(4-chlorophenyl)methyl)-2,6-dimethylpiperazin-1-yl)acetic acid;

2-(4-(bis(4-chlorophenyl)methyl)-2,2-dimethylpiperazin-1-yl)acetic acid; and a mixture of 2-((2R,5S)-4-benzhydryl-2,5-dimethylpiperazin-1-yl)acetic acid dihydrochloride and 2-((2S,5R)-4-benzhydryl-2,5-dimethylpiperazin-1-yl)acetic acid dihydrochloride MS (ESI, pos. ion) m/z: 339 (M+1).

Example 2

Synthesis of 2-(4-(phenyl(3-(trifluoromethyl)phenyl)methyl)piperazin-1-yl)acetic acid

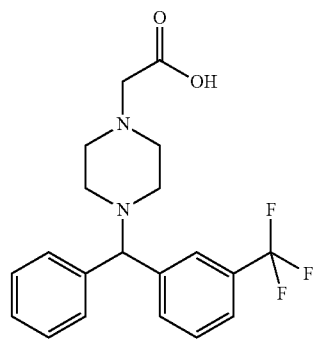 [SMILES: O=C(O)CN1CCN(C(c2ccccc2)c2cccc(C(F)(F)F)c2)CC1]

Method A

A solution of tert-butyl 2-(4-(phenyl(3-(trifluoromethyl)phenyl)methyl)-piperazin-1-yl)acetate (9.3 g, 21 mmol) in TFA (25 mL, 337 mmol) was stirred at 60° C. for 6 h. The reaction mixture was concentrated and the crude product purified by SCX column eluting with MeOH then 2N NH$_3$ in MeOH solution to give the title compound as a racemate (4.8 g, 59%). MS (ESI, pos. ion) m/z: 379.1 (M+1).

Method B

A solution of methyl 2-(4-(phenyl(3-(trifluoromethyl)phenyl)methyl)piperazin-1-yl)acetate (0.86 g, 2 mmol) and 5N sodium hydroxide (0.1 mL, 4 mmol) in MeOH (20 mL) was heated to 70° C. for 1 h. After removal of solvent under reduced pressure, the residue was diluted with water, acidified to pH 4 with 1N HCl, and then extracted with CH$_2$Cl$_2$. The organic layer was washed with brine, dried over Na$_2$SO$_4$, and concentrated. The crude product was purified by ISCO eluting with 0-15% MeOH in dichloromethane to give the title compound (0.7 g, 84% yield). MS (ESI, pos. ion) m/z: 379.1 (M+1).

Using synthesis similar to the synthesis of 2-(4-(phenyl(3-(trifluoromethyl)-phenyl)-methyl)piperazin-1-yl)acetic acid in Method A, 2-(4-((3-bromophenyl)(phenyl)methyl)piperazin-1-yl)acetic acid MS (ESI, pos. ion) m/z: 389.1 (M+);

2-(4-((4-bromophenyl)(phenyl)methyl)piperazin-1-yl)acetic acid MS (ESI, pos. ion) m/z: 389.1 (M+);

2-(4-((3,5-dichlorophenyl)(phenyl)methyl)piperazin-1-yl)acetic acid MS (ESI, pos. ion) m/z: 379.0 (M+1); and 2-(4-benzhydrylpiperazin-1-yl)acetic acid MS (ESI, pos. ion) m/z: 311.1 (M+1) were prepared.

Using synthesis similar to the synthesis of 2-(4-(phenyl(3-(trifluoromethyl)-phenyl)-methyl)piperazin-1-yl)acetic acid in Method B, (R)-2-(4-(phenyl(3-(trifluoromethyl)-phenyl)methyl)piperazin-1-yl)acetic acid MS (ESI, pos. ion) m/z: 379.1 (M+1 and (S)-2-(4-(phenyl(3-(trifluoromethyl)phenyl)methyl)piperazin-1-yl)acetic acid MS (ESI, pos. ion) m/z: 379.1 (M+1) were prepared.

Example 3

Synthesis of 2-(4-((3-bromophenyl)(phenyl)methyl)piperazin-1-yl)acetic acid

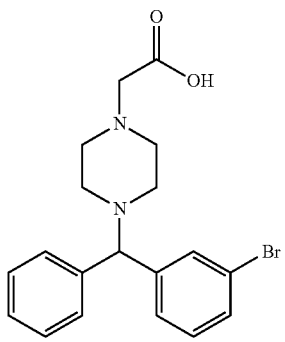 [SMILES: O=C(O)CN1CCN(C(c2ccccc2)c2cccc(Br)c2)CC1]

To a solution of tert-butyl 2-(4-((3-bromophenyl)(phenyl)methyl)piperazin-1-yl)acetate (2.0 g, 4 mmol) in dioxane (10 mL) was added 4N HCl solution in 1,4-dioxane (30 mL, 823 mmol) followed by concentrated HCl (2.0 mL, 55 mmol). The reaction was stirred at 50° C. for 6 h and concentrated under vacuum. The crude product was purified by SCX column eluting with methanol then 2N NH$_3$ in MeOH solution to give the title compound as a racemate (1.62 g, 93%). MS (ESI, pos. ion) m/z: 389.1 (M+).

Example 4

Synthesis of 2-(4-((4-chlorophenyl)(phenyl)methyl)piperazin-1-yl)acetic acid dihydrochloride

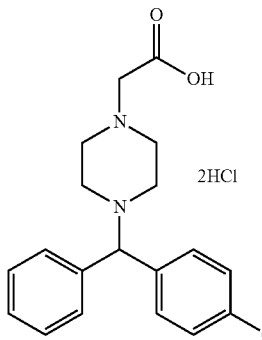

To a solution of tert-butyl 2-(4-((4-chlorophenyl)(phenyl)methyl)piperazin-1-yl)acetate (1.0 g, 2 mmol) in dioxane (10 mL) was added 4N HCl solution in 1,4-dioxane (20 mL, 549 mmol) followed by concentrated HCl (1.0 mL, 27 mmol). The reaction was stirred at 50° C. for 6 h and concentrated under vacuum. The crude product was triturated with EtOAc or diethyl ether, filtered, and dried to give the title compound (0.8 g, 77% yield). MS (ESI, pos. ion) m/z: 345.1 (M+1-2HCl).

Using a method similar to the synthesis of 2-(4-((4-chlorophenyl)(phenyl)-methyl)-piperazin-1-yl)acetic acid dihydrochloride the following compounds:

2-((R)-4-((3-bromophenyl)(phenyl)methyl)-2-methylpiperazin-1-yl)acetic acid dihydrochloride MS (ESI, pos. ion) m/z: 403.1 (M+)-2HCl;

2-((R)-2-methyl-4-(phenyl(3-(trifluoromethyl)phenyl)methyl)piperazin-1-yl)-acetic acid dihydrochloride MS (ESI, pos. ion) m/z: 393.1 (M+1)-2HCl;

2-(4-((2-bromophenyl)(phenyl)methyl)piperazin-1-yl)acetic acid dihydrochloride MS (ESI, pos. ion) m/z: 390.1 (M+1)-2HCl; and 2-(4-(phenyl(4-(trifluoromethyl)phenyl)methyl)piperazin-1-yl)acetic acid dihydrochloride MS (ESI, pos. ion) m/z: 379.1 (M+1)-2HCl; were prepared.

Example 5

Synthesis of 2-(4-(bis(3-(trifluoromethyl)phenyl)methyl)piperazin-1-yl)acetic acid dihydrochloride

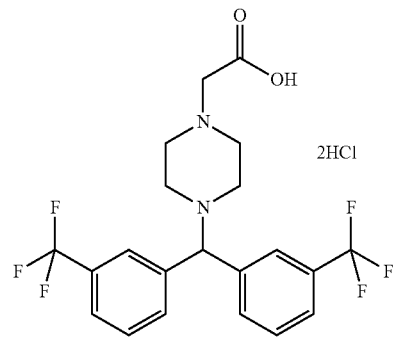 [SMILES: O=C(O)CN1CCN(C(c2cccc(C(F)(F)F)c2)c2cccc(C(F)(F)F)c2)CC1 ; "2HCl"]

Step 1

To a solution of 3,3'-bis(trifluoromethyl)benzophenone (11.4 g, 36 mmol) in MeOH (50 mL) was added sodium borohydride (1.9 ml, 53 mmol) portionwise at rt. The suspension was stirred at rt for 24 h. The reaction was diluted slowly with water and extracted with CH$_2$Cl$_2$. The organic was washed successively with water, brine, dried over Na$_2$SO$_4$, and concentrated to give bis(3-(trifluoromethyl)phenyl)methanol (10.8 g, 94% yield). The crude oil was used in the next reaction without further purification.

Step 2

To a solution of bis(3-(trifluoromethyl)phenyl)methanol (1.1 g, 3.4 mmol) in CH$_2$Cl$_2$ (10 mL) was added dropwise thionyl chloride (0.50 ml, 6.9 mmol) at rt. The reaction was stirred at 50° C. for 4 h, concentrated under vacuum, azeotroped with toluene, and dried under vacuum to give crude chlorobis(3-(trifluoromethyl)phenyl)methane. The crude chlorobis(3-(trifluoromethyl)-phenyl)methane was added to a solution of piperazine (0.81 ml, 10 mmol) in acetonitrile (10 mL), heated to 100° C. for 18 h and concentrated under vacuum. The residue was dissolved in CH$_2$Cl$_2$ (150 mL) and washed with 1N NaOH (150 mL). The organic layer was dried with K$_2$CO$_3$, filtered, and concentrated to give 1-(bis(3-(trifluoromethyl)-phenyl)methyl)piperazine. The crude 1-(bis(3-(trifluoromethyl)phenyl)-methyl)piperazine was dissolved in acetonitrile (10 mL) and tert-butyl bromoacetate (0.55 mL, 3.4 mmol) and triethylamine (0.96 ml, 6.9 mmol) was added. The solution was stirred for 4 h, diluted with water, and extracted with CH$_2$Cl$_2$. The organic layer was washed with saturated NaCl solution, then dried over Na$_2$SO$_4$, and concentrated. The crude product was purified by ISCO using 0-50% EtOAc in haxanes to give tert-butyl 2-(4-(bis(3-(trifluoromethyl)-phenyl)methyl)piperazin-1-yl)acetate (0.86 g, 50% yield). MS (ESI, pos. ion) m/z: 503.1 (M+1), which was then converted to the title compound by proceeding as described in Example 4 above.

Example 6

Synthesis of 2-(4-((3-biphenyl)(phenyl)methyl)piperazin-1-yl)acetic acid dihydrochloride

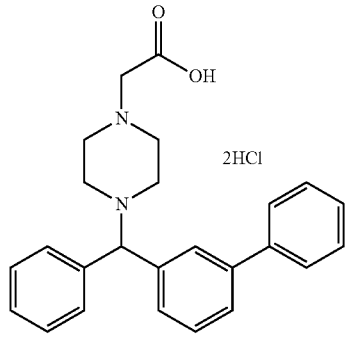 [SMILES: O=C(O)CN1CCN(C(c2ccccc2)c2cccc(-c3ccccc3)c2)CC1 ; "2HCl"]

A mixture of tert-butyl 2-(4-((3-bromophenyl)(phenyl)methyl)piperazin-1-yl)acetate (0.31 g, 0.70 mmol), phenylboronic acid (0.085 g, 0.70 mmol), sodium carbonate monohydrate (0.077 ml, 1.4 mmol), and tetrakis(triphenylphosphine)palladium (0) (0.80 g, 0.70 mmol) in dioxane (4 mL) and water (2 mL) was heated at 120° C. under microwave irradiation for 20 min. The reaction was diluted with water and extracted with CH$_2$Cl$_2$. The organic layer was washed with saturated NaCl solution, then dried over Na$_2$SO$_4$ and concentrated. The crude product was purified by ISCO using 0-50% EtOAc in hexanes to give tert-butyl 2-(4-((3-biphenyl)(phenyl)methyl)-piperazin-1-yl)acetate (0.28 g, 91% yield). MS (ESI, pos. ion) m/z: 443.2 (M+1), which was then converted to the title compound by proceeding as described in Example 4 above.

Proceeding as described in Example 6 above, but substituting tert-butyl 2-(4-((3-bromophenyl)(phenyl)methyl)piperazin-1-yl)acetate with tert-butyl 2-((R)-2-methyl-4-((R)-(3-bromophenyl)(phenyl)methyl)piperazin-1-yl)acetate and phenylboronic acid with thien-2-ylboronic acid provided 2-tert-butyl ((R)-2-methyl-4-((R)-phenyl(3-(thiophen-2-yl)phenyl)methyl)piperazin-1-yl)acetate which was converted to 2-((R)-2-methyl-4-((R)-phenyl(3-(thiophen-2-yl)phenyl)methyl)-piperazin-1-yl)acetic acid as described in Example 4 above.

Proceeding as described in Example 6 above, but substituting tert-butyl 2-(4-((3-bromophenyl)(phenyl)methyl)piperazin-1-yl)acetate with 2-((R)-2-methyl-4-((R)-(4-bromophenyl)(phenyl)methyl)piperazin-1-yl)acetate and treating it with phenylboronic acid, 2-methylphenylboronic acid, 3-methylphenylboronic acid and 4-methylphenylboronic acid provided tert-butyl ((R)-2-methyl-4-((R)-(4-biphenyl)(phenyl)methyl)-piperazin-1-yl)acetate, tert-butyl ((R)-2-methyl-4-((R)-(4-(2-methylphenyl)phenyl)(phenyl)methyl)-piperazin-1-yl)acetate, tert butyl ((R)-2-methyl-4-((R)-(4-(3-methylphenyl)phenyl)-(phenyl)methyl)-piperazin-1-yl)acetate, and tert-butyl ((R)-2-methyl-4-((R)-(4-(4-methylphenyl)-(phenyl)methyl)-piperazin-1-yl) acetate respectively, which were converted to [(R)-4-((R)-biphenyl-4-yl-phenyl-methyl)-2-methyl-piperazin-1-yl]-acetic acid; [(R)-2-methyl-4-[(R)-(2'-methyl-biphenyl-4-yl)-phenyl-methyl]-piperazin-1-yl]-acetic acid; [(R)-2-methyl-4-[(R)-(3'-methyl-biphenyl-4-yl)-phenyl-methyl]-piperazin-1-yl]-acetic acid; and [(R)-2-methyl-4-[(R)-(4'-methyl-biphenyl-4-yl)-phenyl-methyl]-piperazin-1-yl]-acetic acid, respectively, as described in Example 4 above.

Example 7

Synthesis of 2-((R)-4-(cyclopropyl(3-(trifluoromethyl)phenyl)methyl)-2-methylpiperazin-1-yl)acetic acid

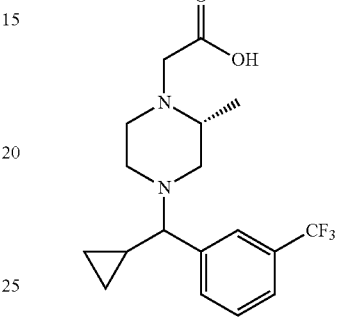

Step 1

To 3-(trifluoromethyl)benzaldehyde (3.48 g, 20 mmol) (azeotroped with benzene) at 0° C. was added cyclopropylmagnesium bromide (0.5 M in THF, 24 mmol) dropwise and the resulting solution was stirred at 0° C. for 1 h. The reaction mixture was quenched with aq. NH$_4$Cl, extracted with ether, washed with water, dried over Na$_2$SO$_4$, filtered and evaporated to dryness. Column chromatography (SiO$_2$, hexane to DCM/hexane=1:1 to pure DCM) afforded (3-bromophenyl)(cyclopropyl)methanol as a yellow oil.

Step 2

To neat cyclopropyl(3-(trifluoromethyl)phenyl)methanol (3.00 g, 13.9 mmol) at rt was slowly added thionyl chloride (1.52 ml, 20.8 mmol) and the resulting solution was stirred at room temperature for 1 h. The excess reagent was removed by azeotroping with toluene and crude 1-(chloro-(cyclopropyl)methyl)-3-(trifluoromethyl)benzene was further dried under high vacuum and used directly in the next step.

Step 3

A mixture of 1-(chloro(cyclopropyl)methyl)-3-(trifluoromethyl)benzene (2.5 g, 11 mmol) and (R)-2-methylpiperazine (3.2 g, 32 mmol) in 30 mL of MeCN was heated at 90° C. overnight. The solvent was evaporated and the solid residue was submitted to column chromatography (SiO$_2$, EtOAc to EtOAc/2M NH$_3$ in MeOH=100:20) to give crude (2R)-1-(cyclopropyl(3-(trifluoromethyl)phenyl)methyl)-2-methylpiperazine (3.15 g) which was directly used in next step.

Step 4

To a solution of crude (2R)-1-(cyclopropyl(3-(trifluoromethyl)phenyl)methyl)-2-methylpiperazine (3.15 g, 105.6 mmol) in 25 mL of MeCN was added tert-butyl bromoacetate (2.046 ml, 12.67 mmol), followed by slow addition of triethylamine (2.203 ml, 15.837 mmol). The reaction mixture was stirred at rt overnight. The solution was evaporated to dryness and the residue was submitted to flash chromatography (SiO$_2$, hexane to hexane/EtOAc=100:5 to 100:10 to 100:30) to give tert-butyl 2-((R)-4-(cyclopropyl(3-(trifluoromethyl)phenyl)methyl)-2-methylpiperazin-1-yl)acetate as a colorless oil.

Step 5

To tert-butyl 2-((R)-4-(cyclopropyl(3-(trifluoromethyl)phenyl)methyl)-2-methylpiperazin-1-yl)acetate (350 mg, 0.849 mmol) in 150 mL flask was added 3 mL of 37% HCl and the resulting solution was stirred at 50° C. for 3 h. After HPLC-MS showed complete conversion, the solvent was evaporated to dryness under high vacuum to give 2-((R)-4-(cyclopropyl(3-(trifluoromethyl)phenyl)methyl)-2-methylpiperazin-1-yl)acetic acid dihydrochloride (290 mg, 79.6% yield) as a white solid. MS (ESI, pos. ion) m/z: 357 (M+1).

Proceeding as described in Example 7 above, but substituting cyclopropylmagnesium bromide with thiophen-2-ylmagnesium bromide provided 2-((R)-2-methyl-4-(thiophen-2-yl(3-(trifluoromethyl)phenyl)methyl)piperazin-1-yl)acetic acid MS (ESI, pos. ion) m/z: 399 (M+1).

2-((R)-2-Methyl-4-(thiophen-2-yl(3-(trifluoromethyl)phenyl)methyl)piperazin-1-yl)acetic acid was then separated into 2-((R)-2-methyl-4-((R)-thiophen-2-yl-(3-(trifluoromethyl)phenyl)-methyl)piperazin-1-yl)acetic acid and 2-((R)-2-methyl-4-((S)-thiophen-2-yl(3-(trifluoromethyl)phenyl)methyl)piperazin-1-yl)acetic acid diastereomers.

Example 8

Synthesis of 2-(4-(bis(4-chlorophenyl)methyl)-2-oxopiperazin-1-yl)acetic acid

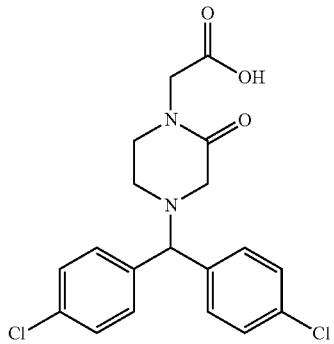 [SMILES: O=C(O)CN1CCN(C(c2ccc(Cl)cc2)c2ccc(Cl)cc2)CC1=O]

Step 1

To a solution of chlorobis(4-chlorophenyl)methane (407 mg, 1.5 mmol) in MeCN was added piperazin-2-one (601 mg, 6.0 mmol) followed by triethylamine (626 μl, 4.5 mmol) and the resulting mixture was refluxed overnight. After cooling to rt, the solvent was evaporated to dryness and the residue was submitted to column chromatography (SiO₂, DCM to DCM/MeOH=100:5) to give 4-(bis(4-chlorophenyl)methyl)piperazin-2-one (420 mg) as a white solid.

Step 2

To a solution of 4-(bis(4-chlorophenyl)methyl)piperazin-2-one (180 mg, 537 μmol) in 10 mL of dry THF was added methyl 2-bromoacetate (60 μl, 644 μmol), followed by sodium hydride, 60% dispersion in mineral oil (16 μl, 644 μmol). After stirring rt overnight, the solvent was evaporated to dryness and was directly submitted to column chromatography (SiO₂, hexane to hexane/EtOAc=100:5 to 100:10 to 100:20 to 100:30) to give methyl 2-(4-(bis(4-chlorophenyl)methyl)-2-oxopiperazin-1-yl)acetate (160 mg) as a white solid.

Step 3

To a solution of methyl 2-(4-(bis(4-chlorophenyl)methyl)-2-oxopiperazin-1-yl)acetate (160 mg, 393 μmol) in THF/MeOH/H₂O=5:5:1 (5.5 mL) was added lithium hydroxide monohydrate (49.5 mg, 1.179 mmol) and the resulting solution was stirred overnight. The solvent was evaporated, diluted with water, adjusted to pH=5 with 10% HCl, extracted with DCM, dried over Na₂SO₄, filtered and evaporated to dryness under high vacuum. The residue was loaded onto flash column (SiO₂, DCM to DCM/MeOH=100:5 to 100:10 to 100:15 to 100:20) to give 2-(4-(bis(4-chlorophenyl)methyl)-2-oxopiperazin-1-yl)acetic acid (136 mg) as a white solid.

Example 9

Synthesis of 2-((R)-2-methyl-4-((R)-phenyl(4-(2-phenylethynyl)phenyl)-methyl)piperazin-1-yl)acetic acid

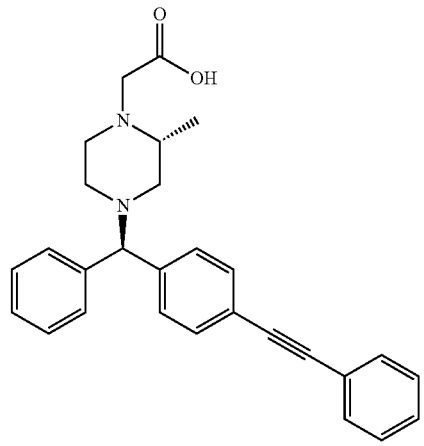 [SMILES: C[C@@H]1CN([C@H](c2ccccc2)c2ccc(C#Cc3ccccc3)cc2)CCN1CC(=O)O]

Step 1

A mixture of tert-butyl 2-((R)-4-((S)-(4-bromophenyl)(phenyl)methyl)-2-methyl-piperazin-1-yl)acetate (459 mg, 0.1 mmol, its preparation follows the general procedures of Reference G), 1-phenylethyne (0.137 ml, 1.249 mmol), tetrabutylammonium fluoride trihydrate (946 mg, 2.997 mmol) and dichlorobis(triphenylphosphine)palladium(ii) (21.0 mg, 0.030 mmol) was heated at 80° C. under N₂ atmosphere for 1 h. The residue was subjected to flash chromatography (SiO₂, hexane to hexane/EtOAc=100:10 to 100:15 to 100:20) to give tert-butyl 2-((R)-2-methyl-4-((S)-phenyl(4-(2-phenylethynyl)phenyl)methyl)-piperazin-1-yl)acetate (460 mg) as a yellow oil.

Step 2

To a solution of tert-butyl 2-((R)-2-methyl-4-((S)-phenyl(4-(2-phenylethynyl)phenyl)-methyl)piperazin-1-yl)acetate (320 mg, 0.666 mmol) in THF/MeOH/H₂O=5:5:1 (5.5 mL) was added lithium hydroxide monohydrate (279 mg, 6.658 mmol) and the resulting solution was stirred overnight. The solvent was evaporated to dryness under high vacuum and the residue was diluted with water, adjusted pH=5, extracted with DCM, dried over Na₂SO₄, filtered and evaporated to dryness. The residue was loaded onto flash column (SiO², DCM to DCM/MeOH=100:5 to 100:10 to 100:15 to 100:20) to give 2-((R)-2-methyl-4-((S)-phenyl(4-(2-phenylethynyl)phenyl)methyl)piperazin-1-yl)acetic acid (240 mg) as a white solid.

Proceeding as described above the following compounds were synthesized:
2-((R)-2-methyl-4-((R)-phenyl(3-(2-pyridin-3-ylethynyl)phenyl)methyl)-piperazin-1-yl)acetic acid; and
2-((R)-2-methyl-4-((R)-phenyl(3-(2-pyridin-4-ylethynyl)phenyl)methyl)-piperazin-1-yl)acetic acid.

Biological Examples

Example 1

Glycine Transporter 1 (GlyT1) Uptake Assay

In Vitro:

This cell-based assay measures the ability of test compounds to inhibit the uptake of glycine by the glycine transporter type 1. Human placental choriocarcinoma (JAR) cells endogenously expressing human glycine transporter type 1 (Gly-T1) were used for this assay. For uptake assays, JAR cells were cultured in 96-well cytostar T scintillating microplates (Amersham Biosciences) in RPMI 1640 medium containing 10% fetal bovine serum in the presence of penicillin (100 μg/ml) and streptomycin (100 μg/ml). Cells were plated at a density of $4 \times 10^4$ cells/well and grown at 37° C. in a humidified atmosphere of 5% $CO_2$ for 24 h.

Culture medium was removed from Cytostar plate and JAR cells were incubated with 30 μl of Uptake buffer (120 mM NaCl, 2 mM KCl, 1 mM $CaCl_2$, 1 mM $MgCl_2$, 10 mM Hepes, 5 mM alanine, pH 7.5) with or without compound for 5 min. Then 30 μl of [$^{14}$C] glycine (101 mCi/mmol, obtained from PerkinElmer) diluted in Uptake buffer was added to each well to give a final concentration of 5 μM. After incubation at room temperature for the desired time usually 1-2 h, sealed 96-well Cytostar plates were counted on a TopCount (Packard). Non-specific uptake of [$^{14}$C] glycine was determined in the presence of 10 μM cold ALX-5407 (Sigma).

$IC_{50}$ curves were generated from the raw data collected from the TopCount and fitted with a four-parameter logistic equation using in-house data analysis tool, ActivityBase. The specific compounds of this invention had an $IC_{50}$ value of less than about 10 micromolar.

In approximate $IC_{50}$ value of a representative number of compounds of Formula (I) in this assay is provided in the Table 9 below.

TABLE 9

| Cpd # | $IC_{50}$ (nM) | Cpd # | $IC_{50}$ (nM) | Cpd # | $IC_{50}$ (nM) |
|---|---|---|---|---|---|
| 1 | 79.1 | 30 | 0.934 | 49 | 7.2 |
| 18 | 37.6 | 34 | 17.8 | 55A | 1.5 |
| 20 | 1.51 | 38 | 0.98 | 75 | 4.32 |
| 21 | 217 | 39 | 2.7 | 77 | 41.1 |
| 24 | 3.94 | 48 | 2.14 | 78 | 4.8 |
| 79 | 1190 | 82 | 2200 | 88 | 134 |

In Vivo Assay:

Male Sprague-Dawley rats (250-300 grams) were treated with GlyT1 inhibitor in Table 1, compound 3, in 2% hydroxypropyl-methycelllulose and 1% tween 80 in water at doses ranging between 1 and 100 mg/kg by oral gavage. Two hours after acute compound administration, CSF was collected and subsequently analyzed for glycine content using HPLC coupled to a fluorescent detector (ESA inc, Chelmsford Mass.). Basal levels of glycine in rat CSF were 0.5 ng/microliter of CSF or lower.

Formulation Examples

The following are representative pharmaceutical formulations containing a compound of Formula (I).

Tablet Formulation

The following ingredients are mixed intimately and pressed into single scored tablets.

| Ingredient | Quantity per tablet mg |
|---|---|
| compound of this invention | 400 |
| cornstarch | 50 |
| croscarmellose sodium | 25 |
| lactose | 120 |
| magnesium stearate | 5 |

Capsule Formulation

The following ingredients are mixed intimately and loaded into a hard-shell gelatin capsule.

| Ingredient | Quantity per capsule mg |
|---|---|
| compound of this invention | 200 |
| lactose spray dried | 148 |
| magnesium stearate | 2 |

Injectable Formulation

Compound of the invention (e.g., compound 1) in 2% HPMC, 1% Tween 80 in DI water, pH 2.2 with MSA, q.s. to at least 20 mg/mL.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

What is claimed is:

1. A method of treating Schizophrenia or cognitive disorder associated with Schizophrenia in a patient which method comprises administering to the patient a pharmaceutical composition comprising a therapeutically effective amount of a compound of Formula (I):

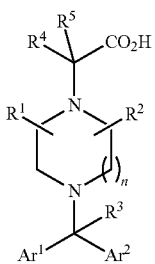

(I)

wherein:

n is an integer from 1 to 3;

$R^1$ and $R^2$ are independently hydrogen, alkyl, haloalkyl, alkoxy, haloalkoxy, aryl, heteroaryl, cycloalkyl, or heterocyclyl wherein the aforementioned rings are optionally substituted with $R^a$, $R^b$, or $R^c$ independently alkyl, halo, haloalkyl, alkoxy, haloalkoxy, hydroxy, cyano, monosubstituted amino, or disubstituted amino; or $R^1$ and $R^2$, when attached to the same carbon atom, can combine to form cycloalkyl or monocyclic saturated heterocyclyl to give a spiro ring wherein the cycloalkyl or monocyclic saturated heterocyclyl can be optionally substituted with $R^d$, $R^e$, or $R^f$ independently alkyl, alkoxy, fluoro, fluoroalkyl, fluoroalkoxy, hydroxy, monosubstituted amino, or disubstituted amino; or $R^1$ and $R^2$, when attached to carbon atoms 2 and 5 or 3 and 6 positions of the piperazine ring, can combine to form —$C_1$-$C_3$— alkylene chain wherein one of the carbon atoms in the alkylene chain is optionally replaced by a —NR—, —O—, —S(O)n1- (wherein R is hydrogen or alkyl and n1 is 0-2) and further wherein one or two hydrogen atoms in the alkylene chain can be optionally substituted with one or two alkyl;

$R^3$, $R^4$ and $R^5$ are independently hydrogen, alkyl, fluoro, or fluoroalkyl; and $Ar^1$ and $Ar^2$ are independently aryl, heteroaryl, cycloalkyl, or heterocyclyl wherein each of the aforementioned ring is optionally substituted with $R^g$, $R^h$ or $R^i$ wherein $R^g$ is alkyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, or acylamino and $R^h$ and $R^i$ are independently alkyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, acylamino, aryl, heteroaryl, cycloalkyl, or heterocyclyl wherein the aromatic or alicyclic ring in $R^g$, $R^h$ and $R^i$ is optionally substituted with $R^j$, $R^k$ or $R^l$ which are independently alkyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, or acylamino;

or a pharmaceutically acceptable salt thereof;

provided that: the compound of Formula (I) is not 2-(4-benzhydrylpiperazin-1-yl)acetic acid or 2-(4-((4-chlorophenyl)(phenyl)methyl)piperazin-1-yl)acetic acid;

and a pharmaceutically acceptable excipient.

2. The method of claim 1 wherein:

n is 1;

$R^1$ and $R^2$ are independently hydrogen, alkyl, haloalkyl, alkoxy, haloalkoxy, aryl, heteroaryl, cycloalkyl, or heterocyclyl wherein the aforementioned rings are optionally substituted with $R^a$, $R^b$, or $R^c$ independently alkyl, halo, haloalkyl, alkoxy, haloalkoxy, hydroxy, cyano, monosubstituted amino, or disubstituted amino; or $R^1$ and $R^2$, when attached to the same carbon atom, can combine to form cycloalkyl or monocyclic saturated heterocyclyl to give a spiro ring wherein the cycloalkyl or monocyclic saturated heterocyclyl can be optionally substituted with $R^d$, $R^e$, or $R^f$ independently alkyl, alkoxy, fluoro, fluoroalkyl, fluoroalkoxy, hydroxy, monosubstituted amino, or disubstituted amino; or $R^1$ and $R^2$, when attached to carbon atoms 2 and 5 or 3 and 6 positions of the piperazine ring, can combine to form —$C_1$-$C_3$— alkylene chain wherein one of the carbon atoms in the alkylene chain is optionally replaced by a —NR—, —O—, —S(O)n1- (wherein R is hydrogen or alkyl and n1 is 0-2) and further wherein one or two hydrogen atoms in the alkylene chain can be optionally substituted with one or two alkyl; and $Ar^1$ and $Ar^2$ are independently aryl, heteroaryl, cycloalkyl, or heterocyclyl wherein each of the aforementioned ring is optionally substituted with $R^g$, $R^h$ or $R^i$ wherein $R^g$ is alkyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, or acylamino and $R^h$ and $R^i$ are independently alkyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, acylamino, aryl, heteroaryl, cycloalkyl, or heterocyclyl wherein the aromatic or alicyclic ring in $R^g$, $R^h$ and $R^i$ is optionally substituted with $R^j$, $R^k$ or $R^l$ which are independently alkyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, or acylamino provided that: the compound of Formula (I) is not 2-(4-benzhydrylpiperazin-1-yl)acetic acid or 2-(4-((4-chlorophenyl)(phenyl)methyl)piperazin-1-yl)acetic acid.

3. The method of claim 1 wherein $R^1$ and $R^2$ are hydrogen.

4. The method of claim 1 wherein $R^1$ is hydrogen and $R^2$ is alkyl.

5. The method of claim 1 wherein $R^1$ and $R^2$ are attached to the same carbon atom and are combined to form cycloalkyl optionally substituted with $R^d$, $R^e$ or $R^f$ which is independently selected from alkyl, alkoxy, fluoro, fluoroalkyl, fluoroalkoxy, hydroxy, monosubstituted amino, or disubstituted amino.

6. The method of claim 1 wherein $R^1$ and $R^2$ are attached to the same carbon atom and are combined to form monocyclic saturated heterocyclyl which are optionally substituted with $R^d$, $R^e$ or $R^f$ which is independently selected from alkyl, alkoxy, fluoro, fluoroalkyl, fluoroalkoxy, hydroxy, monosubstituted amino, or disubstituted amino.

7. The method of claim 1 wherein $R^1$ and $R^2$ are attached to carbon atoms 2 and 5 or 3 and 6 positions of the piperazine ring, and are combined to form —$C_1$-$C_2$-alkylene chain wherein one or two hydrogen atoms in the alkylene chain can be optionally substituted with one or two alkyl.

8. The method of claim 1 wherein $R^1$, $R^2$, $R^3$, $R^4$ and $R^5$ are hydrogen and $Ar^1$ and $Ar^2$ are phenyl, each optionally substituted with $R^g$, $R^h$ or $R^i$.

9. The method of claim 1 wherein $R^1$, $R^3$, $R^4$, and $R^5$ are hydrogen, $R^2$ is alkyl, and $Ar^1$ and $Ar^2$ are phenyl, each optionally substituted with $R^g$, $R^h$ or $R^i$.

10. The method of claim 1 wherein $R^1$, $R^2$, $R^3$, $R^4$ and $R^5$ are hydrogen, $Ar^1$ is phenyl optionally substituted with $R^g$, $R^h$ or $R^i$ and $Ar^2$ is cycloalkyl.

11. The method of claim 1 wherein $R^1$, $R^3$, $R^4$, and $R^5$ are hydrogen, $R^2$ is alkyl, $Ar^1$ is phenyl optionally substituted with $R^g$, $R^h$ or $R^i$ and $Ar^2$ is cycloalkyl.

12. The method of claim 1 wherein $R^1$, $R^2$, $R^3$, $R^4$ and $R^5$ are hydrogen, $Ar^1$ is phenyl and $Ar^2$ is heteroaryl, each ring optionally substituted with $R^g$, $R^h$ or $R^i$.

13. The method of claim 1 wherein $R^1$, $R^3$, $R^4$, and $R^5$ are hydrogen, $R^2$ is alkyl, $Ar^1$ is phenyl and $Ar^2$ is heteroaryl, each ring optionally substituted with $R^g$, $R^h$ or $R^i$.

14. The method of claim 1 wherein $R^1$, $R^3$, $R^4$ and $R^5$ are hydrogen, $R^2$ is hydrogen or methyl and $Ar^1$ and $Ar^2$ are independently phenyl, each ring optionally substituted with $R^g$ or $R^h$ wherein $R^g$ and $R^h$ are independently methyl, fluoro, trifluoromethyl, trifluoromethoxy or 2,2,2-trifluoroethoxy.

15. The method of claim 1 wherein the compound has the structure:

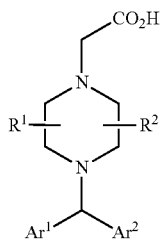

where:

$R^1$ and $R^2$ are independently hydrogen or alkyl; and $Ar^1$ and $Ar^2$ are independently phenyl, each ring optionally substituted with $R^g$ or $R^h$ wherein $R^g$ and $R^h$ are independently alkyl, halo, haloalkyl, haloalkoxy, alkylthio, alkoxy, alkylcarbonyl, or alkoxycarbonyl.

16. The method of claim 1 wherein the compound has the structure:

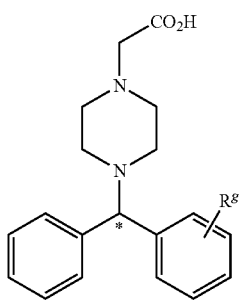

(a)

$R^g$ is alkyl, halo, haloalkyl, or haloalkoxy and is attached to the 3-position of the phenyl ring and the stereochemistry at *C is (R).

17. The method of claim 1 wherein the compound has the structure:

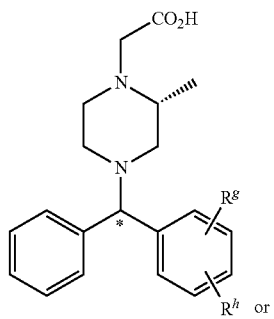

(b)

or

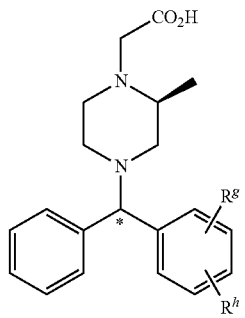

(c)

wherein $R^g$ and $R^h$ are independently absent, alkyl, halo, haloalkyl, or haloalkoxy and the stereochemistry at *C is (R).

18. The method of claim 1 wherein the compound is selected from a group consisting of:

(R)-2-(4-(phenyl(3-(trifluoromethyl)phenyl)methyl)piperazin-1-yl)acetic acid;

2-(4-((3-bromophenyl)(phenyl)methyl)piperazin-1-yl)acetic acid;

2-(4-(phenyl(3-(trifluoromethyl)phenyl)methyl)piperazin-1-yl)acetic acid;

2-(4-((3,5-dichlorophenyl)(phenyl)methyl)piperazin-1-yl)acetic acid;

(S)-2-(4-(phenyl(3-(trifluoromethyl)phenyl)methyl)piperazin-1-yl)acetic acid;

2-(4-((4-bromophenyl)(phenyl)methyl)piperazin-1-yl)acetic acid;

2-(4-benzhydrylpiperazin-1-yl)acetic acid;

2-(4-((4-chlorophenyl)(phenyl)methyl)piperazin-1-yl)acetic acid;

2-(4-(phenyl(4-(trifluoromethyl)phenyl)methyl)piperazin-1-yl)acetic acid;

2-(4-((2-bromophenyl)(phenyl)methyl)piperazin-1-yl)acetic acid;

2-(4-((3-biphenyl)(phenyl)methyl)piperazin-1-yl)acetic acid;

(S)-2-(4-((4-bromophenyl)(phenyl)methyl)piperazin-1-yl)acetic acid;

(R)-2-(4-((4-bromophenyl)(phenyl)methyl)piperazin-1-yl)acetic acid;

(S)-2-(4-((3-bromophenyl)(phenyl)methyl)piperazin-1-yl)acetic acid;

(R)-2-(4-((3-bromophenyl)(phenyl)methyl)piperazin-1-yl)acetic acid;

2-((R)-2-methyl-4-(phenyl(3-(trifluoromethyl)phenyl)methyl)piperazin-1-yl)acetic acid;

2-((R)-4-((3-bromophenyl)(phenyl)methyl)-2-methylpiperazin-1-yl)acetic acid;

(R)-2-(4-benzhydryl-2-methylpiperazin-1-yl)acetic acid;
2-((R)-4-((R)-(3-iodophenyl)(phenyl)methyl)-2-methylpiperazin-1-yl)acetic acid;
2-((R)-4-((R)-(3-bromophenyl)(phenyl)methyl)-2-methylpiperazin-1-yl)acetic acid;
2-((R)-4-((S)-(3-bromophenyl)(phenyl)methyl)-2-methylpiperazin-1-yl)acetic acid;
2-((R)-2-methyl-4-(biphenyl-3-yl-phenyl-methyl)-piperazin-1-yl)-acetic acid;
2-((R)-2-methyl-4-((S)-phenyl(3-(trifluoromethyl)phenyl)methyl)piperazin-1-yl)acetic acid;
2-((R)-2-methyl-4-((R)-phenyl(3-(trifluoromethyl)phenyl)methyl)piperazin-1-yl)acetic acid;
2-((R)-4-((4-chlorophenyl)(phenyl)methyl)-2-methylpiperazin-1-yl)acetic acid;
2-((R)-2-methyl-4-(biphenyl-4-yl-phenyl-methyl)-piperazin-1-yl)-acetic acid;
2-((R)-4-((4-bromophenyl)(phenyl)methyl)-2-methylpiperazin-1-yl)acetic acid;
2-((R)-4-((4-cyanophenyl)(phenyl)methyl)-2-methylpiperazin-1-yl)acetic acid;
2-((R)-4-((3-chlorophenyl)(phenyl)methyl)-2-methylpiperazin-1-yl)acetic acid;
[(R)-4-((R)-biphenyl-3-yl-phenyl-methyl)-2-methyl-piperazin-1-yl]-acetic acid;
2-((R)-2-methyl-4-((3-(methylthio)phenyl)(phenyl)methyl)piperazin-1-yl)acetic acid;
2-((R)-4-((S)-(2-bromophenyl)(phenyl)methyl)-2-methylpiperazin-1-yl)acetic acid;
2-((R)-4-((R)-(2-bromophenyl)(phenyl)methyl)-2-methylpiperazin-1-yl)acetic acid;
2-((R)-2-methyl-4-((R)-phenyl(m-tolyl)methyl)piperazin-1-yl)acetic acid;
2-((R)-4-((R)-(3-isopropylphenyl)(phenyl)methyl)-2-methylpiperazin-1-yl)acetic acid;
2-((R)-4-((4-fluorophenyl)(phenyl)methyl)-2-methylpiperazin-1-yl)acetic acid;
2-((R)-4-((3-fluorophenyl)(phenyl)methyl)-2-methylpiperazin-1-yl)acetic acid;
2-((R)-2-methyl-4-((R)-phenyl(3-(thiophen-2-yl)phenyl)methyl)piperazin-1-yl)acetic acid;
2-((R)-2-methyl-4-((R)-(3-(methylthio)phenyl)(phenyl)methyl)piperazin-1-yl)acetic acid;
2-((R)-2-methyl-4-((S)-(3-(methylthio)phenyl)(phenyl)methyl)piperazin-1-yl)acetic acid;
2-((R)-2-methyl-4-((R)-(4-(methylthio)phenyl)(phenyl)methyl)piperazin-1-yl)acetic acid;
2-((R)-4-((S)-(2-fluorophenyl)(phenyl)methyl)-2-methylpiperazin-1-yl)acetic acid;
2-((R)-4-((R)-(2-fluorophenyl)(phenyl)methyl)-2-methylpiperazin-1-yl)acetic acid;
2-((R)-2-methyl-4-((S)-phenyl(3-(trifluoromethoxy)phenyl)methyl)piperazin-1-yl)acetic acid;
2-((R)-2-methyl-4-((R)-phenyl(3-(trifluoromethoxy)phenyl)methyl)piperazin-1-yl)acetic acid;
[(R)-4-((R)-biphenyl-4-yl-phenyl-methyl)-2-methyl-piperazin-1-yl]-acetic acid;
{(R)-2-methyl-4-[(R)-(2'-methyl-biphenyl-4-yl)-phenyl-methyl]-piperazin-1-yl}-acetic acid;
{(R)-2-methyl-4-[(R)-(3'-methyl-biphenyl-4-yl)-phenyl-methyl]-piperazin-1-yl}-acetic acid;
{(R)-2-methyl-4-[(R)-(4'-methyl-biphenyl-4-yl)-phenyl-methyl]-piperazin-1-yl}-acetic acid;
2-((R)-4-((S)-(2,4-difluorophenyl)(phenyl)methyl)-2-methylpiperazin-1-yl)acetic acid;
2-((R)-4-((R)-(2,4-difluorophenyl)(phenyl)methyl)-2-methylpiperazin-1-yl)acetic acid;
2-((R)-4-((S)-(4-fluorophenyl)(phenyl)methyl)-2-methylpiperazin-1-yl)acetic acid;
2-((R)-4-((R)-(4-fluorophenyl)(phenyl)methyl)-2-methylpiperazin-1-yl)acetic acid;
2-((R)-4-((S)-(3-fluorophenyl)(phenyl)methyl)-2-methylpiperazin-1-yl)acetic acid;
2-((R)-4-((R)-(3-fluorophenyl)(phenyl)methyl)-2-methylpiperazin-1-yl)acetic acid;
(S)-2-(4-benzhydryl-2-methylpiperazin-1-yl)acetic acid;
2-((S)-2-methyl-4-(phenyl(3-(trifluoromethyl)phenyl)methyl)piperazin-1-yl)acetic acid;
(S)-2-(4-benzhydryl-3-methylpiperazin-1-yl)acetic acid;
(R)-2-(4-benzhydryl-3-methylpiperazin-1-yl)acetic acid;
2-((2,5-trans)-4-benzhydryl-2,5-dimethylpiperazin-1-yl)acetic acid;
2-((2,5-cis)-4-benzhydryl-2,5-dimethylpiperazin-1-yl)acetic acid;
2-((R)-3-methyl-4-(phenyl(4-diphenyl)methyl)piperazin-1-yl)acetic acid;
(R)-2-(4-(bis(3-chlorophenyl)methyl)-2-methylpiperazin-1-yl)acetic acid;
(R)-2-(4-(bis(3-fluorophenyl)methyl)-2-methylpiperazin-1-yl)acetic acid;
2-(4-((3-(trifluoromethyl)phenyl)(4-(trifluoromethyl)phenyl)methyl)piperazin-1-yl)acetic acid;
2-(4-((4-fluorophenyl)(3-(diphenyl)methyl))-(R)-2-methylpiperazin-1-yl)acetic acid
(R)-2-(4-(bis(4-chlorophenyl)methyl)-2-methylpiperazin-1-yl)acetic acid;
2-((R)-4-((3-bromophenyl)(4-fluorophenyl)methyl)-2-methylpiperazin-1-yl)acetic acid;
(R)-2-(4-(bis(4-fluorophenyl)methyl)-3-methylpiperazin-1-yl)acetic acid;
(R)-2-(4-(bis(4-fluorophenyl)methyl)-2-methylpiperazin-1-yl)acetic acid;
(R)-2-(4-(bis(3-(trifluoromethyl)phenyl)methyl)-2-methylpiperazin-1-yl)acetic acid;
2-(4-(bis(3-(trifluoromethyl)phenyl)methyl)piperazin-1-yl)acetic acid;
2-((R)-2-methyl-4-(thiophen-2-yl(3-(trifluoromethyl)phenyl)methyl)piperazin-1-yl)acetic acid;
2-((R)-2-methyl-4-((R)-thiophen-2-yl(3-(trifluoromethyl)phenyl)methyl)piperazin-1-yl)acetic acid;
2-((R)-2-methyl-4-((S)-thiophen-2-yl(3-(trifluoromethyl)phenyl)methyl)piperazin-1-yl)acetic acid;
2-((R)-4-(cyclopropyl(3-(trifluoromethyl)phenyl)methyl)-2-methylpiperazin-1-yl)acetic acid;
(R)-2-(4-(bis(4-chlorophenyl)methyl)-2-methylpiperazin-1-yl)acetic acid;
(S)-2-((R)-4-(bis(4-chlorophenyl)methyl)-3-methylpiperazin-1-yl)propanoic acid;
(S)-2-((R)-4-(bis(4-chlorophenyl)methyl)-2-methylpiperazin-1-yl)propanoic acid;
(R)-2-((R)-4-(bis(4-chlorophenyl)methyl)-2-methylpiperazin-1-yl)propanoic acid;
2-((2R,6S)-4-(bis(4-chlorophenyl)methyl)-2,6-dimethylpiperazin-1-yl)acetic acid;
2-(4-(bis(4-chlorophenyl)methyl)-2,2-dimethylpiperazin-1-yl)acetic acid;
2-(4-(bis(4-chlorophenyl)methyl)piperazin-1-yl)propanoic acid;
(R)-2-(4-(bis(4-chlorophenyl)methyl)-2-isopropylpiperazin-1-yl)acetic acid;
2-(4-(bis(4-chlorophenyl)methyl)piperazin-1-yl)acetic acid; and
2-(4-(phenyl(3-(trifluoromethyl)phenyl)methyl)-1,4-diazepan-1-yl)-acetic acid;
or a pharmaceutically acceptable salt thereof.

19. The method of claim 1 wherein the compound is (R)-2-(4-(phenyl(3-(trifluoromethyl)phenyl)methyl)piperazin-1-yl)acetic acid; or a pharmaceutically acceptable salt thereof.

20. The method of claim 1 wherein the compound is 2-((R)-4-(cyclopropyl(3-(trifluoromethyl)phenyl)methyl)-2-methylpiperazin-1-yl)acetic acid; or a pharmaceutically acceptable salt thereof.

21. The method of claim 1 wherein the compound is 2-((R)-2-methyl-4-((R)-phenyl(3-(trifluoromethyl)phenyl)methyl)piperazin-1-yl)acetic acid; or a pharmaceutically acceptable salt thereof.

22. The method of claim 1 wherein the compound of formula (I) is administered in combination with an agent which is sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, or PDE10 antagonists.

23. The method of claim 22 wherein said agent is adinazolam, allobarbital, alonimid, alprazolam, amisulpride, amitriptyline, amobarbital, amoxapine, aripiprazole, bentazepam, benzoctamine, brotizolam, bupropion, busprione, butabarbital, butalbital, capuride, carbocloral, chloral betaine, chloral hydrate, clomipramine, clonazepam, cloperidone, clorazepate, chlordiazepoxide, clorethate, chlorpromazine, clozapine, cyprazepam, desipramine, dexclamol, diazepam, dichloralphenazone, divalproex, diphenhydramine, doxepin, estazolam, ethchlorvynol, etomidate, fenobam, flunitrazepam, flupentixol, fluphenazine, flurazepam, fluvoxamine, fluoxetine, fosazepam, glutethimide, halazepam, haloperidol, hydroxyzine, imipramine, lithium, lorazopam, lormetazepam, maprotiline, mecloqualone, melatonin, mephobarbital, meprobamate, methaqualone, midaflur, midazolam, nefazodone, nisobamate, nitrazopam, nortriptyline, olanzapine, oxazepam, paraldehyde, paroxetine, pentobarbital, perlapine, perphenazine, phenelzine, phenobarbital, prazepam, promethazine, propofol, protriptyline, quazepam, quetiapine, reclazepam, risperidone, roletamide, secobarbital, sertraline, suproclone, temazopam, thioridazine, thiothixene, tracazolate, kanylcypromaine, trazodone, triazolam, trepipam, tricetamide, triclofos, trifluoperazine, trimetozine, trimipramine, uldazepam, venlafaxine, zaleplon, ziprasidone, zolazepam, zolpidem, or combinations thereof.

24. The method of claim 1 wherein the compound of formula (I) is administered in combination with an agent which is an anti-depressant or anti-anxiety agent, selective serotonin reuptake inhibitors, monoamine oxidase inhibitors, reversible inhibitors of monoamine oxidase, serotonin and noradrenaline reuptake inhibitors, corticotropin releasing factor antagonists, adrenoreceptor antagonists, neurokinin-1 receptor antagonists, atypical anti-depressants, benzodiazopines, 5-HTA agonists, 5-HTA antagonists, or corticotropin releasing factor antagonists.

25. The method of claim 24 wherein said agent is amitriptyline, clomipramine, doxepin, imipramine, trimipramine, amoxapine, desipramine, maprotiline, nortriptyline, protriptyline, fluoxetine, fluvoxamine, paroxetine, sertraline, isocarboxazid, phenelzine, tranylcypromine, selegiline, moclobemide, venlafaxine, duloxetine, aprepitant, bupropion, lithium, nefazodone, trazodone, viloxazine, alprazolam, chlordiazepoxide, clonazopam, chlorazepate, diazopam, halazepam, lorazepam, oxazopam, prazepam, buspirone, flesinoxan, gepirone, ipsapirone, or combinations thereof.

* * * * *